United States Patent [19]
Young et al.

[11] Patent Number: 5,885,831
[45] Date of Patent: Mar. 23, 1999

[54] NUCLEAR LOCALIZATION FACTOR ASSOCIATED WITH CIRCADIAN RHYTHMS

[75] Inventors: Michael W. Young, Upper Saddle River, N.J.; Amita Sehgal, Haverford, Pa.; Leslie B. Vosshall, New York, N.Y.; Jeffrey L. Price, Morgantown, W. Va.; Michael P. Myers, Washington Township, N.J.

[73] Assignees: The Rockefeller University, New York, N.Y.; The Trustees of the University of Pennsylvania, Philadelphia, Pa.

[21] Appl. No.: 619,198

[22] Filed: Mar. 21, 1996

Related U.S. Application Data

[63] Continuation-in-part of Ser. No. 552,354, Nov. 2, 1995, abandoned, which is a continuation-in-part of Ser. No. 442,214, May 16, 1995, abandoned, which is a continuation-in-part of Ser. No. 408,518, Mar. 20, 1995, abandoned.

[51] Int. Cl.$^6$ ..................................................... C12N 5/10
[52] U.S. Cl. .................... 435/336; 435/252.33; 530/350; 530/388.24; 536/24.31
[58] Field of Search .............................. 435/336, 252.33; 530/350, 388.24; 536/24.31

*Primary Examiner*—James Ketter
*Attorney, Agent, or Firm*—Klauber & Jackson

[57] ABSTRACT

The invention includes a nucleic acid encoding a nuclear localization protein which binds to, stabilizes and translocates to the nucleus a protein involved in circadian rhythms. Also included are the protein encoded by the nucleic acid, antibodies to the protein, and compositions and kits for the diagnosis and treatment of disorders related to the sleep-wake cycle.

25 Claims, 33 Drawing Sheets

Wild type tim

FIG.5A
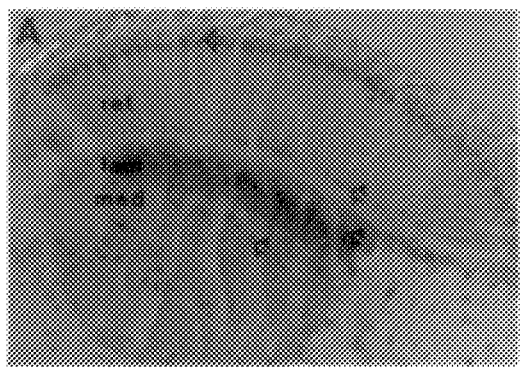
FIG.5D
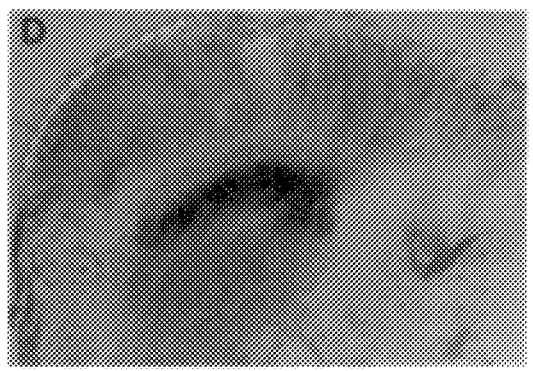
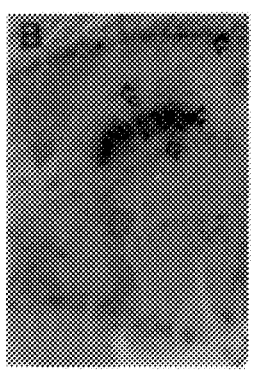 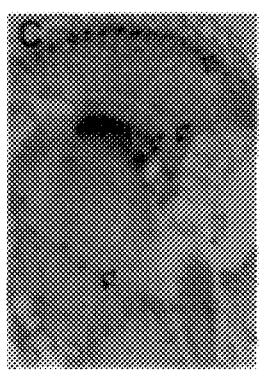 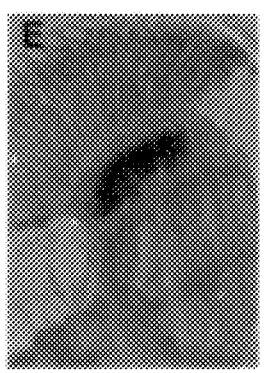 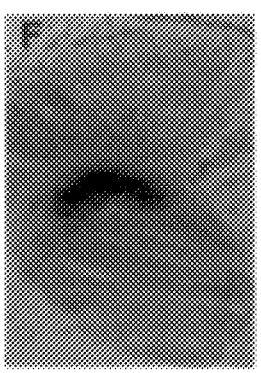
FIG.5B  FIG.5C  FIG.5E  FIG.5F
FIG.5G
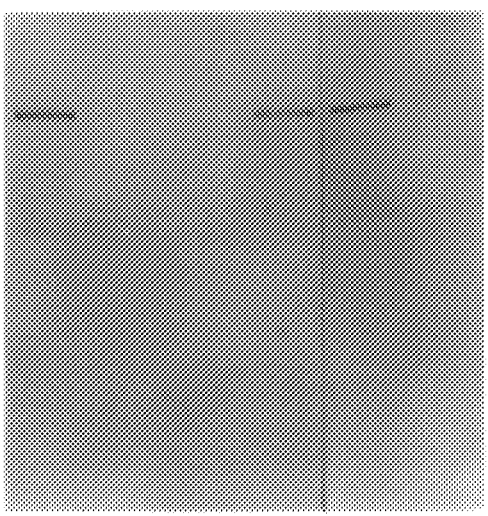

FIG.11A

```
  1     AATTTCATCAGTGCATATATAACAGCACTGAAACTATAAACACGATCTATTCTGCAAAGAAAC
 61     CCAAAAAGTGCTCAGAGAAAAGCTCAATTGCTTAGAAACACAGTAAACATAAACATCAGCTTTAATTGTT
121     GATTGCAATTCGGCTAAAACTAAAAACTAAAAACAGTAAGTCTGCGATAGAAAAATT
181     TAAATAATTGTTACAGATACCGCGCAAATGGCTAAGAAGTACCTCAATGTTCGCAGTCGA
                                                                              .
241     CAATGAGCAGAGTTAGGCAGCTCCACAATCACATCTGGAATAATCAGAACTTTGATAAAG
  1      M  S  R  V  R  Q  L  H  N  H  I  W  N  N  Q  N  F  D  K  V
                                                                              .
301     TGAAATCGGTTATGGACTGGTTACTAGCAACTCCCGCAGTTGTACAGCCGCGTTCTCCTCCT
 21      K  S  V  M  D  W  L  L  A  T  P  Q  L  Y  S  A  F  S  S  L
                                                                              .
361     TGGGTTGCTTGGAGGGCGATACCTATGTGGTCAACCCGAATGCATTGGCCACTTCTGGAGG
 41      G  C  L  E  G  D  T  Y  V  V  N  P  N  A  L  A  I  L  E  E
                                                                              .
421     AGATCAACTACAAGCTCACCTATGAGGACCAAACACTGCGCCACCTTTCGACGGGCCATTG
 61      I  N  Y  K  L  T  Y  E  D  Q  T  L  R  T  F  R  R  A  I  G
                                                                              .
481     GATTTGGCCAGAATGTGAGGTCAGACCTGATACCGCTTCTTGGAGAATGCCAAGGATGATG
 81      F  G  Q  N  V  R  S  D  L  I  P  L  L  E  N  A  K  D  D  A
                                                                              .
541     CGGTCCTGGAGTCGGTCGATATCCGGTCATCGTCAATCTGACGGTGCCGGTGGAGTGCCTCT
101      V  L  E  S  V  I  R  I  L  V  N  L  T  V  P  V  E  C  L  F
                                                                              .
601     TCTCCGTGACGTGATGTACCGGACGGATGTGGGTCGCCACCATCTTCGAGCTGAATA
121      S  V  D  V  M  Y  R  T  D  V  G  R  H  T  I  F  E  L  N  K
                                                                              .
661     AGCTGCTGTACACCAGCAAGGAAGCATTTACCGAGGCCAGGAGCACCAAGAGCGTGGTGG
141      L  L  Y  T  S  K  E  A  F  T  E  A  R  S  T  K  S  V  V  E
                                                                              .
721     AGTACATGAAACACATACTGGAGTCGGACCCCTAAGCTGTCGCCGCACAAATGCGATCAAA
161      Y  M  K  H  I  L  E  S  D  P  K  L  S  P  H  K  C  D  Q  I
                                                                              .
781     TCAACAACTGTCTGCTGCTGCGAGAAATATCCTGCACATTCCAGAGACGCATGCCCATT
181      N  N  C  L  L  L  R  N  I  L  H  I  P  E  T  H  A  H  C
```

FIG.11B

```
 841  GCGTGATGCCCCATGATGATGCAGTCGATGCCGCATCTCCATGCAGAGAACACGATCTTGT
 201   V  M  P  M  M  M  Q  S  M  P  H  G  I  S  M  Q  N  T  I  L  W

901  GGAATCTCTTCATCCAGAGCATCGACAAGTTACTCCTGTATCTGATGACCTGTCCGCAGA
 221   N  L  F  I  Q  S  I  D  K  L  L  L  Y  L  M  T  C  P  Q  R

961  GAGCCTTCTGGGGAGTGACCATGGTGCAACTGATTGCTTTGATCTACAAGGATCAGCATG
 241   A  F  W  G  V  T  M  V  Q  L  I  A  L  I  Y  K  D  Q  H  G

1021  GCAGTGGCGATTCCAGCCCCATGCTGACCTCTGATCCCACCTCCGATTCCTCGGACAACG
 261   S  G  D  S  S  P  M  L  T  S  D  P  T  S  D  S  S  D  N  G

1081  GCAGCAATGGCCGTGGCATGGGGGGTGTGGCATGCGGGAAGAACAGCGGCCACTTTGCAGG
 281   S  N  G  R  G  M  G  G  M  R  E  G  T  A  A  T  L  Q  E

1141  AGGTCAGCCGCAAGGGTCAGGAGTATCAGAACGCCATGGCCAGAGTGCCAGCGGATAAGC
 301   V  S  R  K  G  Q  E  Y  Q  N  A  M  A  R  V  P  A  D  K  P

1201  CCGATGGCTCCGAAGAGGCCAGCGATATGACGGGGAACAGCGAGCAGCCTGGATCGC
 321   D  G  S  E  E  A  S  D  M  T  G  N  D  S  E  Q  P  G  S  P

1261  CGGAGCAATCGCAGCCCGCGGGAGAGTCCATGGATGATGGAGATTACGAGGACCAGAGAC
 341   E  Q  S  Q  P  A  G  E  S  M  D  D  D  G  D  Y  E  D  Q  R  H

1321  ACAGGCAACTGAACGAGCATGGCGAAGAGGATGAAGATGAGGACGAAGTGGAGGAGGAAG
 361   R  Q  L  N  E  H  G  E  E  D  E  D  E  D  V  E  E  E  E  E

1381  AGTACCTACAATTGGGCCCTGCAGCCCTCGGAGCCCTTAACTTAACAACCAGCTGACA
 381   Y  L  Q  L  G  P  A  S  E  P  L  N  L  T  Q  Q  P  A  D  K

1441  AGGTCAACAACACTACCAACCCAACGTCCAGTGGCTGCGCAAGGCCTGCCTGGGCAATGAGC
 401   V  N  N  T  T  N  P  T  S  S  A  P  Q  G  C  L  G  N  E  P

1501  CATTCAAGCCACCACCTCCTCTGCCACTCCAGAGCTCAGAGCCTTCGGCACACGCTCAAATGC
 421   F  K  P  P  P  P  L  P  V  R  A  S  T  S  A  H  A  Q  M  Q
```

FIG.11C

```
1561  AGAAGTTCAACGAATCGTCCTACGCGTCCCACGTATCTGCGGTCAAATTGGGCCAAAAGT.
 441   K  F  N  E  S  S  Y  A  S  H  V  S  A  V  K  L  G  Q  K  S .

1621  CCCCACATGCCGGCCAGCTCCAGCTCGGACCAAGGGCAAGTGTTGTCCACAGAAGCGGAAT.
 461   P  H  A  G  Q  L  Q  L  T  K  G  K  C  C  P  Q  K  R  E  C .

1681  GCCCCTCCTGCAGTCGGAGCTATCGGGATTGCGGTTATGCGGTTATGGCAGGTGAAAATCAGG.
 481   P  S  S  Q  S  E  L  S  D  C  G  Y  G  T  Q  V  E  N  Q  E .

1741  AATCCATTTCCACCTCCAGCAACGACGATGATGGGCCGCAGGGGCCGCAGCCAGA.
 501   S  I  S  T  S  S  N  D  D  D  G  P  Q  G  K  P  Q  H  Q  K .

1801  AGCCTCCGTGTAACACGGAAGCCACGGAATAAACCACGGACGATTATGTCGCCAATGGACA.
 521   P  P  C  N  T  K  P  R  N  K  P  R  T  I  M  S  P  M  D  K .

1861  AAAAGGAGCTTAGACGCAAAAAAACTGGTCAAGCGCAGCAAAAAGCAGCCTCATCAACATGA.
 541   K  E  L  R  R  K  K  L  V  K  R  S  S  K  S  S  L  I  N  M  K .

1921  AGGGTCTGGTACAGCACACACCCCCACCGATGACATCTCCAATCTGCTGAAGGAATTCA.
 561   G  L  V  Q  H  T  P  T  D  D  D  I  S  N  L  L  K  E  F  T .

1981  CCGTGGATTTCCTCCTCCTCAAGGGTTACAGCTATCTGGTGGAGGAACTGCACATGCAACTGC.
 581   V  D  F  L  L  K  G  Y  S  Y  L  V  E  E  L  H  M  Q  L  L .

2041  TTTCCAATGCGAAGGTGCCCATTGACACCTCCCACTTCTTTTTGGCTGGTAACCTACTTCC.
 601   S  N  A  K  V  P  I  D  T  S  H  F  F  W  L  V  T  Y  F  L .

2101  TGAAGTTTGCCGCCCAACTGGAGCTGGATATGGAGCATATTGACACTATTCTCACCTACG.
 621   K  F  A  A  Q  L  E  L  D  M  E  H  I  D  T  I  L  T  Y  D .

2161  ATGTTTTGAGCTACTTGACTTATGAGGGTGTGTCCCTATGTGAGCAACTGGAACTGAATG.
 641   V  L  S  Y  L  T  Y  E  G  V  S  L  C  E  Q  L  E  L  N  A .

2221  CCCGACAGGAGGGCAGTGACCTGAAGCCCTATCTAAGGCGAATGCACTTGGTGGTGACGG.
 661   R  Q  E  G  S  D  L  K  P  Y  L  R  R  M  H  L  V  V  T  A .
```

FIG.11D

```
2281       CCATCCGGGAGTTCCTCCAGGCCATTGATACGTACAACAAAGTGACTCATCTGAACGAGG
681         I  R  E  F  L  Q  A  I  D  T  Y  N  K  V  T  H  L  N  E  D

2341       ACGACAAAGCCCATTTGAGGCAGCTTCAGCTGCAGATTAGCGAAAT TCCGATCTGAGGT
701         D  K  A  H  L  R  Q  L  Q  I  S  E  M  S  D  L  R  C
                                       tim01 deletion  [ I  -  -  -

2401       GCCTTTTTGTGCTTCTGCTGAGGCGTTTCAATCCCAGCATTCATTCCAAGC AGTATCTTC
721         L  F  V  L  L  L  R  R  F  N  P  S  I  H  S  K  Q  Y  L  Q
            -  -  -  -  -  -  -  -  -  -  -  -  -  -  -  -    S  I  F

2461       AGGATCTGGTGGTTACCAATCACATCCTCCTACTCATTCTGGACAGTTCGGCCAAACTTG
741         R  I  W  L  P  I  T  S  S  Y  S  F  W  T  V  R  P  N  L
            -  D  L  V  V  T  N  H  I  L  L  L  D  S  S  A  K  L  G

2521       GTGGATGTCAAACCATTCGCCTGTCGGAGCACATAACAGTTTGCCACGCTGGAGGTGA
761         G  C  Q  T  I  R  L  S  E  H  I  T  Q  F  A  T  L  E  V  M
            -  -  -  -  -  -  -  -  -  -  -  -  -  -  -  -  -  -  T ]
            V  D  V  K  P  F  A  C  R  S  T ]
```

FIG.11E

```
2581  TGCACTACTATGGCATTCTGTTGGAGGACTTCAACAACGGAGAGTTTGTCAATGACT .
 781   C  T  T  M  G  I  L  L  E  D  F  N  N  G  E  F  V  N  D  C
         H  Y  Y

2641  GCATCTTCACCATGATGCATCACATCGGTGTGGGCCAGATCTGGGCCAGATTGGGGGTTCTATTTC .
 801   I  F  T  M  M  H  H  I  G  G  D  L  G  Q  I  G  V  L  F  Q

2701  AACCAATTATTTTGAAAAACCTATTCAAGAATTTGGGAAGCGGACTATGAACTGTGCGATG .
 821   P  I  I  L  K  T  Y  S  R  I  W  E  A  D  Y  E  L  C  D  D

2761  ACTGGTCTGATCTTATCGAGTATGTGATTCACAAGTTCATGAATACTCCTCCGAAGTCGC .
 841   W  S  D  L  I  E  Y  V  I  H  K  F  M  N  T  P  P  K  S  P

2821  CACTCACCATTCCTACAACTTCCTTGACGGAAATGACCAAGGAACACAGGAGCATA .
 861   L  T  I  P  T  T  S  L  T  E  M  T  K  E  H  N  Q  E  H  T

2881  CCGTTTGCTCTTGGTCGCAGGAGGAAATGGACACACTTTATTGGTATTATGTGCAGAGCA .
 881   V  C  S  Q  E  E  M  D  T  L  Y  W  Y  Y  V  Q  S  K

2941  AGAAGAACAACGATATTGTGGGAAAGATAGTTAAGCTCTTCAGCAACAACGGCAACAAGC .
 901   K  N  N  D  I  V  G  K  I  V  K  L  F  S  N  N  G  N  K  L

3001  TGAAAACCAGGATTTCTATTATCCAACAACTTTTGCAACAAGACATTATCACCCTGTTGG .
 921   K  T  R  I  S  I  I  Q  Q  L  Q  Q  D  I  I  T  L  L  E

3061  AATACGATGACCTGATGAAGTTCGAGGATGCAGAGTATCAGAGAACTTTGCTGACAACTC .
 941   Y  D  D  L  M  K  F  E  D  A  E  Y  Q  R  T  L  L  T  T  P

3121  CCACTTCCGCAACAACAGAGTCTGGAGGTAAGGAGTGCGCCTACGGCAAACCCT .
 961   T  S  A  T  T  E  S  G  I  E  I  K  E  C  A  Y  G  K  P  S

3181  CAGATGATGTTCAGATCCTGCTGGACCTGATCATTAAGGAAAACAAGGCGCAGCATTTGT .
 981   D  D  V  Q  I  L  L  D  L  I  I  K  E  N  K  A  Q  H  L  L

3241  TATGGCTGCAAAGGATCCTCATTGAGTGCTTCGTTAAACTGACCCTGCGGGAGTGGTC .
1001   W  L  Q  R  I  L  I  E  C  F  V  K  L  T  L  R  S  G  L
```

FIG.11F

```
3301  TCAAGGTTCCGGAAGGCGATCACATCATGGAGCCGGTGGCCTACCACTGCATCTGCAAGC
1021   K  V  P  E  G  D  H  I  M  E  P  V  A  Y  H  C  I  C  K  Q

3361  AGAAGTCCATTCCGGTGGTGCAGTGGAACAACGAGCAATTCCACTACGATGCTGTACCAGC
1041   K  S  I  P  V  V  Q  W  N  N  E  Q  S  T  M  L  Y  Q  P

3421  CTTTTGTTCTCCTGCTCCACAAGCTGGGCATTCAGCTGCCGGCGGACGCGGGCTCGATCT
1061   F  V  L  L  H  K  L  G  I  Q  L  P  A  D  A  G  S  I  F

3481  TCGCCAGAATTCCGGACTACTGGACACCGGAGACAATGTACGGACTCGCCAAAAAGCTGG
1081   A  R  I  P  D  Y  W  T  P  E  T  M  Y  G  L  A  K  K  L  G

3541  GACCGCTGGACAAACGTGAGTTAAAGTCAACCACAGAAAAAACCCATTTGTCATTC
1101   P  L  D  K  R  E  L  K  S  T  T  E  K  N  P  F  V  I  P
            [L]

3601  CACAAAGGTGATGTATATACCGTTATCAACAATTTTTGCTCTCTCTGTGTGAAATTTT
1121   Q  R

3661  GATCATGGGAATCTCGCCCCGAAATCCAAATCCGTGCTTCCATTCCATTCCCATTCT

3721  CATTGTGTGTCCGTCGGTGTATCTCGATATGCTGTGTGCCTCTCTCTTCTCCTCCTTCT

3781  GGGCTCTTATAGTCAACCTCAAGTTCGACGCCAGTGAACTGGAGGATGCGACGGTCGA
1106   N  L  K  F  D  A  S  E  L  E  D  A  T  A  S  S

3841  GTCCGTCGCGTTACCACCACGGAGAGCTGCCTCAGCTGCTTCGGTAAGCAGCCTGG
1122   P  S  R  Y  H  H  T  G  P  R  N  S  L  S  S  V  S  S  L  D

3901  ACGTGGATCTCGGCGATACCGAGGAGCTGGCCCTTATACCCGAGGTGGATGCGGCCGTGG
1142   V  D  L  G  D  T  E  E  L  A  L  I  P  E  V  D  A  A  V  E

3961  AGAAGGCACACGCCATGGCCATCCACGCCCAGCAGGAGATTTTCGCGGTTCCCAAGA
1162   K  A  H  A  M  A  S  T  P  S  P  S  E  I  F  A  V  P  K  T
```

FIG.11G

```
3961  AGAAGGCACACGCCATGGCATCCACGCCCATCGCCCAGCGAGATTTTCGCGGTTCCCAAGA
1162   K  A  H  A  M  A  S  T  P  S  P  S  E  I  F  A  V  P  K  T

4021  CGAAGCACTGCAACTGCATCGATCATCAGATACACCAGATCCCACGCCTCCAGTGCCCAACT
1182   K  H  C  N  S  I  I  R  Y  T  P  D  P  P  P  V  P  N  W

4081  GGCTGCAGTTGGTCATGCGCAGCAAATGCAATCATCGCACAGGTTCCGTCTGGTGATCCCA
1202   L  Q  L  V  M  R  S  K  C  N  H  R  T  G  P  S  G  D  P  S

4141  GCGATTGCGTTGGCTCCTCCGTCGACAACCGTGGACGATGAGGGATTTGGCAAGTCCATCA
1222   D  C  V  G  S  S  T  T  V  D  D  E  G  F  G  K  S  I  S

4201  GTGCAGCCACTTCGCAGGCGGCGAGCACCTCCATGAGCACGGTTAATCCCACAACCACTT
1242   A  A  T  S  Q  A  A  S  T  S  M  S  T  V  N  P  T  T  L

4261  TGAGCCTGAACATGCTAAACACCTTCATGGGAAGCCACAACGAGAACAGCAGTTCTG
1262   S  L  N  M  L  N  T  F  M  G  S  H  N  E  N  S  S  S  G

4321  GTTGCGGGGGCACCGTCTCCTCCCTGTCCATGGTGGCTCTGATGAGCACCGGCGCGGCAG
1282   C  G  G  T  V  S  S  L  S  M  V  A  L  M  S  T  G  A  A  G

4381  GCGGAGGAGGTAACACTTCCGGGCTGGAAATGGATGTGGACGCCTCCATGAAGTCCTCGT
1302   G  G  G  N  T  S  G  L  E  M  D  V  D  A  S  M  K  S  S  F

4441  TCCGAGCGGCTGGAGGTAAACGGATCGCACTTCTCCGGGCCAACAACTTGGACCAGGAGT
1322   E  R  L  E  V  N  G  S  H  F  S  R  A  N  N  L  D  Q  E  Y

4501  ACAGTGCCATGGTGGCATCTGTGTACGAAAAGGAGAAGGAATTAAACAGCGACAATGTCT
1342   S  A  M  V  A  S  V  Y  E  K  E  K  E  L  N  S  D  N  V  S

4561  CTTTGGCCTCGGACCTGACCAGAATGTATGTGAGCGATGAGGACGATCGACTTGAGCGAA
1362   L  A  S  D  L  T  R  M  Y  V  S  D  E  D  D  R  L  E  R  T

4621  CCGAGATCCGGGTGCCCCACTATCACTGAGGATCCAATTCCAATCGATCCTAACCGATCC
1382   E  I  R  V  P  H  Y  H
```

FIG.11H

```
4681  GATCCGATATCCGAGTTTTGAGTGAGGCCCACCCAGCTGGAAAGAATTGTACCTTAATCA
4741  ATCAAATCAAGTAACGTTTAATATCACCCGGCACAAGGATTGTACATTTTATGACCTCTA
4801  AATGCAAAAGTATACCTGATTAATTAGCTACGCATAACGTAAATTACGCGGATAAACAAA
4861  AAAGTCCAAGCAGAAAAGTGAAGAAAAGTGCATTATTTGGTTAATGAATGTGAGGCTCTG
4921  CAGACTGTTTGCCTATGCTAGCCCACTAGATACTCTTAAGTTAACCTTAGTTTCCAATCG
4981  TATTCGGTATACCTACCTACCACATACACACATGTAAATGGGCAGTTCCTGGTT
5041  CAAATAGTGCAAATATACACACATAAATCTATTTACACGTTTAAGAAAGAAGAGCGACCG
5101  GTGTCCATCCACCAAAAACCATCTGTATGTATATCCTTAGTCATAAGTTATGCTTAGCAG
5161  TAATAAAGCTTTCCCTGTAGCCAAAAAAAA
```

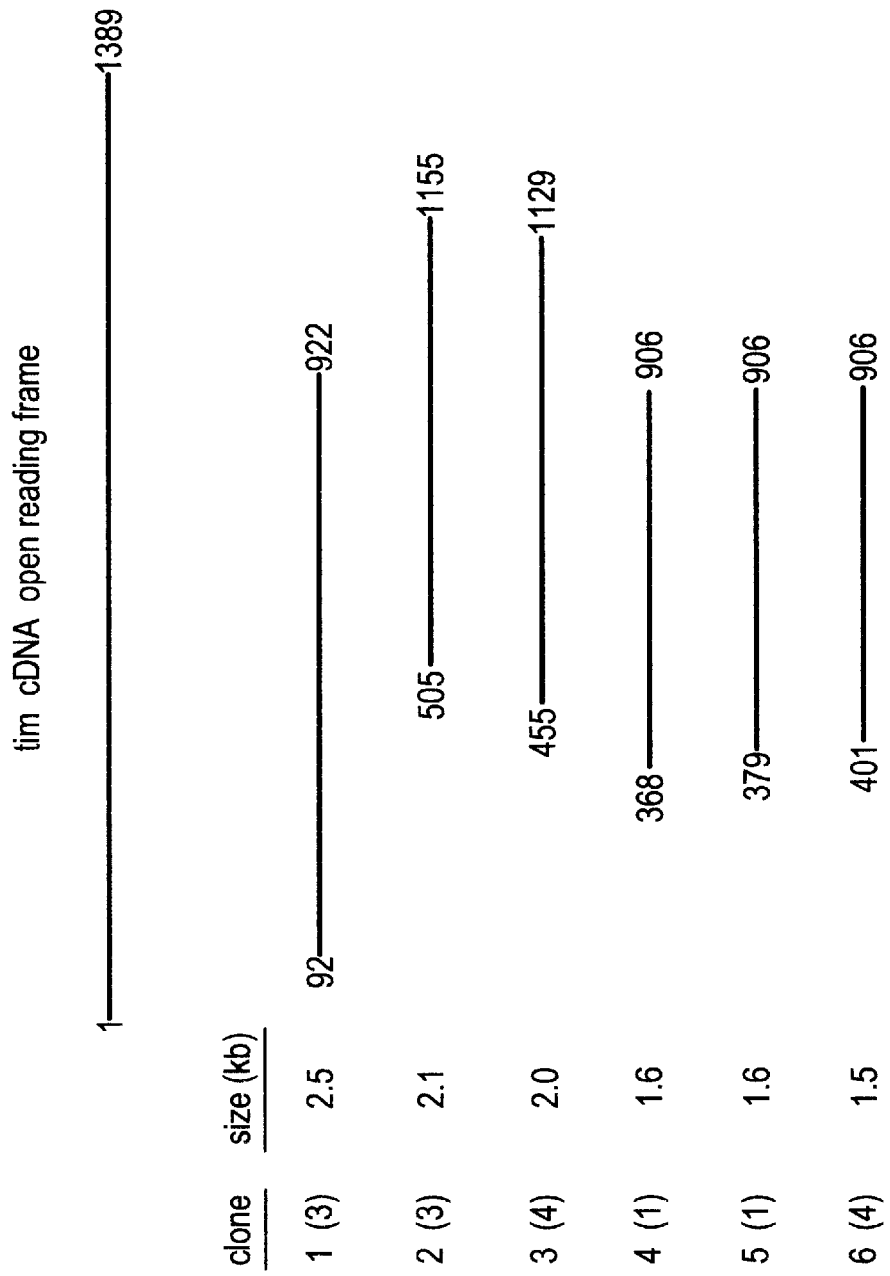

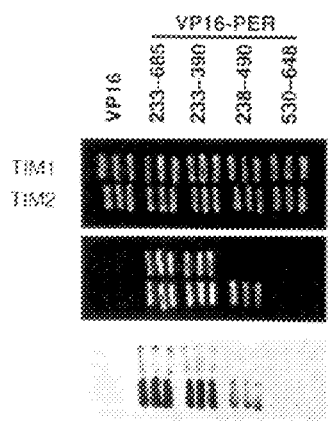
FIG.16A  FIG.16B  FIG.16C  FIG.16D

FIG. 20A
FIG. 20B
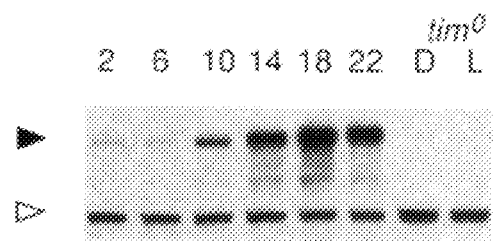
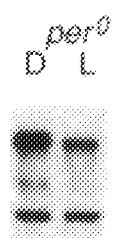
FIG. 20C
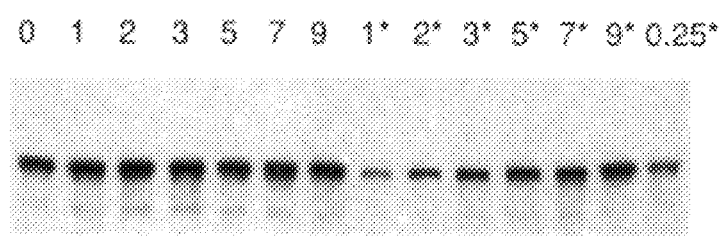
FIG. 20D
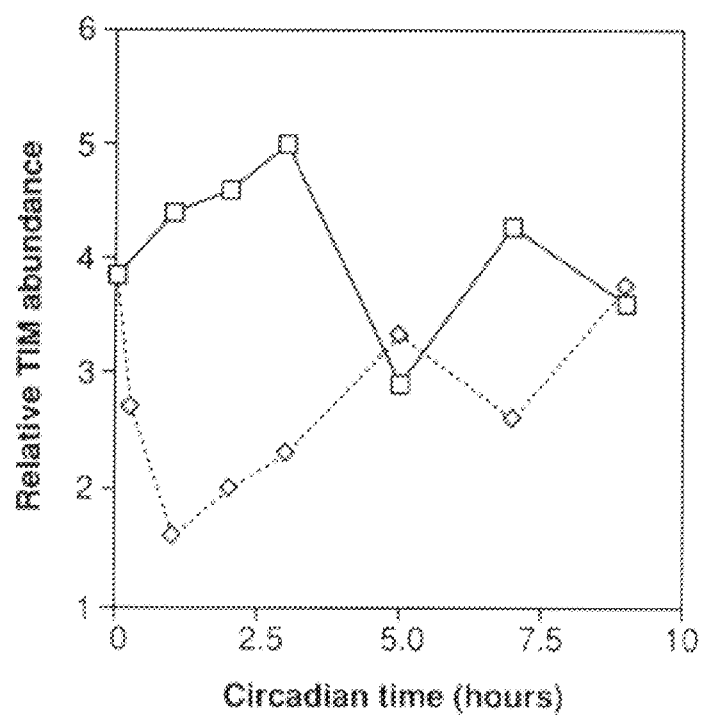

FIG.22A FIG.22B FIG.22C FIG.22D
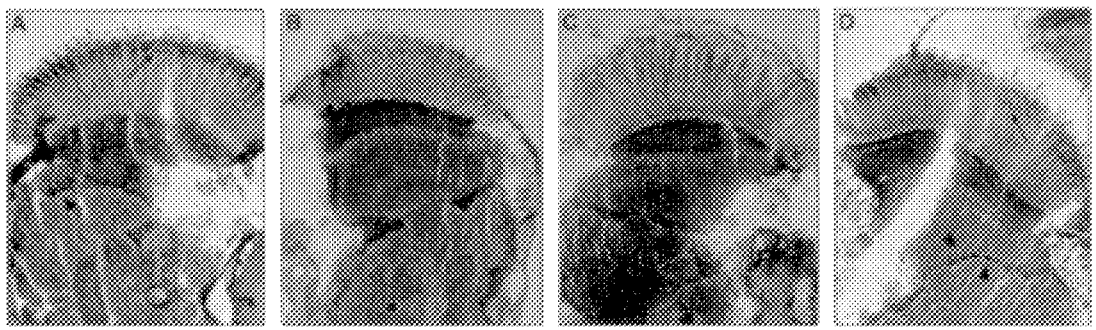
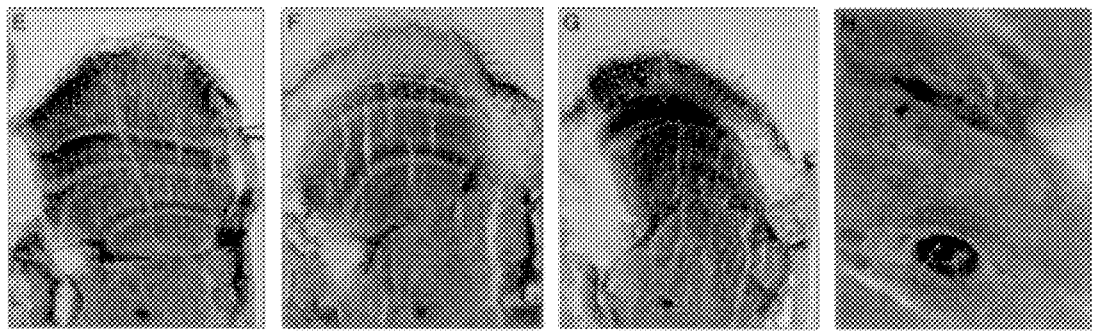
FIG.22E FIG.22F FIG.22G FIG.22H

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 5198 base pairs
        ( B ) TYPE: nucleic acid
        ( C ) STRANDEDNESS: double
        ( D ) TOPOLOGY: linear ( i i ) MOLECULE TYPE: cDNA
        ( A ) DESCRIPTION: tim cDNA sequence wherein R at position 1575

( i i i ) HYPOTHETICAL: NO ( i v ) ANTI-SENSE: NO ( v i ) ORIGINAL SOURCE:
        ( A ) ORGANISM: Drosophila melanogaster ( x i ) SEQUENCE DESCRIPTION: SEQ ID NO:1:

```
TTTCATCAGT  GCATATAACA  GCACTGAAAC  TATAACACGA  TCTATTCTGC  AAAGAAACCC       60

AAAAAGTGCT  CAGAAAAGCT  CAATTGCTTA  GAAACATAAA  CAATCAGCTT  TAATTGTTGA      120

TTGCAATTCG  GCTAAAACTA  AAACTAAAAC  AGTAAAATTG  TCTGCGATAG  AAAAAATTTA      180

AATAATTGTT  ACAGATACCG  CGCAAATGGC  TAAGAAGTAC  CTCAATGTTC  GCAGTCGACA      240

ATGAGCAGAG  TTAGGCAGCT  CCACAATCAC  ATCTGGAATA  ATCAGAACTT  TGATAAAGTG      300

AAATCGGTTA  TGGACTGGTT  ACTAGCAACT  CCGCAGTTGT  ACAGCGCGTT  CTCCTCCTTG      360

GGTTGCTTGG  AGGGCGATAC  CTATGTGGTC  AACCCGAATG  CATTGGCCAT  TCTGGAGGAG      420

ATCAACTACA  AGCTCACCTA  TGAGGACCAA  ACACTGCGCA  CCTTTCGACG  GGCCATTGGA      480

TTTGGCCAGA  ATGTGAGGTC  AGACCTGATA  CCGCTGCTGG  AGAATGCCAA  GGATGATGCG      540

GTCCTGGAGT  CGGTCATCCG  GATACTCGTC  AATCTGACGG  TGCCGGTGGA  GTGCCTCTTC      600
```

```
TCCGTGGACG TGATGTACCG CACGGATGTG GGTCGCCACA CCATCTTCGA GCTGAATAAG    660
CTGCTGTACA CCAGCAAGGA AGCATTTACC GAGGCCAGGA GCACCAAGAG CGTGGTGGAG    720
TACATGAAAC ACATACTGGA GTCGGACCCT AAGCTGTCGC CGCACAAATG CGATCAAATC    780
AACAACTGTC TGCTGCTGCT GAGAAATATC CTGCACATTC CAGAGACGCA TGCCCATTGC    840
GTGATGCCCA TGATGCAGTC GATGCCGCAT GGCATCTCCA TGCAGAACAC GATCTTGTGG    900
AATCTCTTCA TCCAGAGCAT CGACAAGTTA CTCCTGTATC TGATGACCTG TCCGCAGAGA    960
GCCTTCTGGG GAGTGACCAT GGTGCAACTG ATTGCTTTGA TCTACAAGGA TCAGCATGGC   1020
AGTGGCGATT CCAGCCCCAT GCTGACCTCT GATCCCACCT CCGATTCCTC GGACAACGGC   1080
AGCAATGGCC GTGGCATGGG CGGTGGCATG CGGGAAGGAA CAGCGGCCAC TTTGCAGGAG   1140
GTCAGCCGCA AGGGTCAGGA GTATCAGAAC GCCATGGCCA GAGTGCCAGC GGATAAGCCC   1200
GATGGCTCCG AAGAGGCCAG CGATATGACG GGAACGACA GCGAGCAGCC TGGATCGCCG   1260
GAGCAATCGC AGCCCGCCGG CGAGTCCATG GATGATGGAG ATTACGAGGA CCAGAGACAC   1320
AGGCAACTGA ACGAGCATGG CGAAGAGGAT GAAGATGAGG ACGAAGTGGA GGAGGAAGAG   1380
TACCTACAAT TGGGCCCAGC CTCGGAGCCC CTTAACTTAA CACAACAACC AGCTGACAAG   1440
GTCAACAACA CTACCAACCC AACGTCCAGT GCGCCACAAG GCTGCCTGGG CAATGAGCCA   1500
TTCAAGCCAC CACCTCCTCT GCCAGTCAGA GCCTCCACCT CGGCACACGC TCAAATGCAG   1560
AAGTTCAACG AATCRTCCTA CGCGTCCAC GTATCTGCGG TCAAATTGGG CCAAAAGTCC   1620
CCACATGCCG GCCAGCTCCA GCTGACCAAG GGCAAGTGTT GTCCACAGAA GCGGGAATGC   1680
CCCTCCTCGC AGTCGGAGCT ATCGGATTGC GGTTATGGCA CCCAGGTGGA AAATCAGGAA   1740
TCCATTTCCA CCTCCAGCAA CGACGATGAT GGGCCGCAGG GCAAGCCGCA GCACCAGAAG   1800
CCTCCGTGTA ACACGAAGCC ACGGAATAAA CCACGGACGA TTATGTCGCC AATGGACAAA   1860
AAGGAGCTTA GACGCAAAAA ACTGGTCAAG CGCAGCAAAA GCAGCCTCAT CAACATGAAG   1920
GGTCTGGTAC AGCACACCCC CACCGATGAT GACATCTCCA ATCTGCTGAA GGAATTCACC   1980
GTGGATTTCC TCCTCAAGGG TTACAGCTAT CTGGTGGAGG AACTGCACAT GCAACTGCTT   2040
TCCAATGCGA AGGTGCCCAT TGACACATCG CACTTCTTTT GGCTGGTAAC CTACTTCCTG   2100
AAGTTTGCCG CCCAACTGGA GCTGGATATG GAGCACATCG ACACTATTCT CACCTACGAT   2160
GTTTTGAGCT ACTTGACCTA TGAGGGTGTG TCCCTATGTG AGCAACTGGA ACTGAATGCC   2220
CGACAGGAGG GCAGTGACCT GAAGCCCTAT CTAAGGCGAA TGCACTTGGT GGTGACGGCC   2280
ATCCGGGAGT TCCTCCAGGC CATTGATACG TACAACAAAG TGACTCATCT GAACGAGGAC   2340
GACAAAGCCC ATTTGAGGCA GCTTCAGCTG CAGATTAGCG AAATGTCCGA TCTGAGGTGC   2400
CTTTTTGTGC TTCTGCTGAG GCGTTTCAAT CCCAGCATTC ATTCCAAGCA GTATCTTCAG   2460
GATCTGGTGG TTACCAATCA CATCCTCCTA CTCATTCTGG ACAGTTCGGC CAAACTTGGT   2520
GGATGTCAAA CCATTCGCCT GTCGGAGCAC ATAACACAGT TTGCCACGCT GGAGGTGATG   2580
CACTACTATG GCATTCTGTT GGAGGACTTC AACAACAACG GAGAGTTTGT CAATGACTGC   2640
ATCTTCACCA TGATGCATCA CATCGGTGGC GATCTGGGCC AGATTGGGGT TCTATTTCAA   2700
CCAATTATTT TGAAAACCTA TTCAAGAATT TGGGAAGCGG ACTATGAACT GTGCGATGAC   2760
TGGTCTGATC TTATCGAGTA TGTGATTCAC AAGTTCATGA ATACTCCTCC GAAGTCGCCA   2820
CTCACCATTC CTACAACTTC CTTGACGGAA ATGACCAAGG AACACAACCA GGAGCATACC   2880
GTTTGCTCTT GGTCGCAGGA GGAAATGGAC ACACTTTATT GGTATTATGT GCAGAGCAAG   2940
AAGAACAACG ATATTGTGGG AAAGATAGTT AAGCTCTTCA GCAACAACGG CAACAAGCTG   3000
```

```
AAAACCAGGA  TTTCTATTAT  CCAACAACTT  TTGCAACAAG  ACATTATCAC  CCTGTTGGAA   3060
TACGATGACC  TGATGAAGTT  CGAGGATGCG  GAGTATCAGA  GAACTTTGCT  GACAACTCCC   3120
ACTTCCGCAA  CAACAGAGTC  TGGAATTGAG  ATTAAGGAGT  GCGCCTACGG  CAAACCCTCA   3180
GATGATGTTC  AGATCCTGCT  GGACCTGATC  ATTAAGGAAA  ACAAGGCGCA  GCATTTGTTA   3240
TGGCTGCAAA  GGATCCTCAT  TGAGTGCTGC  TTCGTTAAAC  TGACCCTGCG  GAGTGGTCTC   3300
AAGGTTCCGG  AAGGCGATCA  CATCATGGAG  CCGGTGGCCT  ACCACTGCAT  CTGCAAGCAG   3360
AAGTCCATTC  CGGTGGTGCA  GTGGAACAAC  GAGCAATCCA  CTACGATGCT  GTACCAGCCT   3420
TTTGTTCTCC  TGCTCCACAA  GCTGGGCATT  CAGCTGCCGG  CGGACGCGGG  CTCGATCTTC   3480
GCCAGAATTC  CGGACTACTG  GACACCGGAG  ACAATGTACG  GACTCGCCAA  AAAGCTGGGA   3540
CCGCTGGACA  AACGTGAGTT  AAAGTCAACC  ACAGAAAAAA  ACAACCCATT  TGTCATTCCA   3600
CAAAGGTGAT  GTATATACCG  TTATCAACAA  TTTTTGCTCT  CTCTCTGTGT  GAAATTTTGA   3660
TCATGGGAAT  CTCGCCCGAA  ACCGAATCCA  AATCCGTGCT  TCCATCCATT  CCCATTCTCA   3720
TTGTGTGTCC  GTCGGTGTAT  CTCGATATGC  TGTGTGCCTC  TCTCCTTCTC  CTCCTTCTGG   3780
GCTCTTATAG  TCAACCTCAA  GTTCGACGCC  AGTGAACTGG  AGGATGCGAC  GGCGTCGAGT   3840
CCGTCGCGTT  ACCACCACAC  CGGACCCCGC  AACTCGCTCA  GCTCGGTAAG  CAGCCTGGAC   3900
GTGGATCTCG  GCGATACCGA  GGAGCTGGCC  CTTATACCCG  AGGTGGATGC  GGCCGTGGAG   3960
AAGGCACACG  CCATGGCATC  CACGCCATCG  CCCAGCGAGA  TTTTCGCGGT  TCCCAAGACG   4020
AAGCACTGCA  ACTCGATCAT  CAGATACACA  CCAGATCCCA  CGCCTCCAGT  GCCCAACTGG   4080
CTGCAGTTGG  TCATGCGCAG  CAAATGCAAT  CATCGCACAG  GTCCGTCTGG  TGATCCCAGC   4140
GATTGCGTTG  GCTCCTCGTC  GACAACCGTG  GACGATGAGG  GATTTGGCAA  GTCCATCAGT   4200
GCAGCCACTT  CGCAGGCGGC  GAGCACCTCC  ATGAGCACGG  TTAATCCCAC  AACCACTTTG   4260
AGCCTGAACA  TGCTAAACAC  CTTCATGGGA  AGCCACAACG  AGAACAGCAG  CAGTTCTGGT   4320
TGCGGGGGCA  CCGTCTCCTC  CCTGTCCATG  GTGGCTCTGA  TGAGCACCGG  CGCGGCAGGC   4380
GGAGGAGGTA  ACACCTCCGG  GCTGGAAATG  GATGTGGACG  CCTCCATGAA  GTCCTCGTTC   4440
GAGCGGCTGG  AGGTAAACGG  ATCGCACTTC  TCGCGGGCCA  ACAACTTGGA  CCAGGAGTAC   4500
AGTGCCATGG  TGGCATCTGT  GTACGAAAAG  GAGAAGGAAT  TAAACAGCGA  CAATGTCTCT   4560
TTGGCCTCGG  ACCTGACCAG  AATGTATGTG  AGCGATGAGG  ACGATCGACT  TGAGCGAACC   4620
GAGATCCGGG  TGCCCCACTA  TCACTGAGGA  TCCAATTCCA  ATCGATCCTA  ACCGATCCGA   4680
TCCGATATCC  GAGTTTTGAG  TGAGGCCCAC  CCAGCTGGAA  AGAATTGTAC  CTTAATCAAT   4740
CAAATCAAGT  AACGTTTAAT  ATCACCCGGC  ACAAGGATTG  TACATTTTAT  GACCTCTAAA   4800
TGCAAAAGTA  TACCTGATTA  ATTAGCTACG  CATAACGTAA  ATTACGCGGA  TAAACAAAAA   4860
AAGTCCAAGC  AGAAAGTGAA  GAAAAGTGCA  TTATTTGGTT  AATGAATGTG  AGGCTCTGCA   4920
GACTGTTTGC  CTATGCTAGC  CCACTAGATA  CTCTTAAGTT  AACCTTAGTT  TCCAATCGTA   4980
TTCGGTATAC  CTACCTACCA  CATACACACA  CATACATGTA  AATGGGCAGT  TCCTGGTTCA   5040
AATAGTGCAA  ATATACACAC  ATAAATCTAT  TTACACGTTT  AAGAAAGAAG  AGCGACCGGT   5100
GTCCATCCAC  CAAAAACCAT  CTGTATGTAT  ATCCTTAGTC  ATAAGTTATG  CTTAGCAGTA   5160
ATAAAGCTTT  CCCTGTAGCC  AAAAAAAAAA  GGGGGCCC                             5198
```

( 2 ) INFORMATION FOR SEQ ID NO:2:

( i ) SEQUENCE CHARACTERISTICS:
        ( A ) LENGTH: 3369 base pairs ( B ) TYPE: nucleic acid
( C ) STRANDEDNESS: double
( D ) TOPOLOGY: linear ( i i ) MOLECULE TYPE: cDNA
( A ) DESCRIPTION: tim cDNA sequence wherein R at position 1335

( i i i ) HYPOTHETICAL: NO ( i v ) ANTI-SENSE: NO ( v i ) ORIGINAL SOURCE:
( A ) ORGANISM: Drosophila melanogaster ( i x ) FEATURE:
( A ) NAME/KEY: CDS
( B ) LOCATION: 1..3369

( x i ) SEQUENCE DESCRIPTION: SEQ ID NO:2:

| ATG | AGC | AGA | GTT | AGG | CAG | CTC | CAC | AAT | CAC | ATC | TGG | AAT | AAT | CAG | AAC | 48 |
| Met | Ser | Arg | Val | Arg | Gln | Leu | His | Asn | His | Ile | Trp | Asn | Asn | Gln | Asn | |
| 1 | | | | 5 | | | | | 10 | | | | | 15 | | |

| TTT | GAT | AAA | GTG | AAA | TCG | GTT | ATG | GAC | TGG | TTA | CTA | GCA | ACT | CCG | CAG | 96 |
| Phe | Asp | Lys | Val | Lys | Ser | Val | Met | Asp | Trp | Leu | Leu | Ala | Thr | Pro | Gln | |
| | | | 20 | | | | | 25 | | | | | 30 | | | |

| TTG | TAC | AGC | GCG | TTC | TCC | TCC | TTG | GGT | TGC | TTG | GAG | GGC | GAT | ACC | TAT | 144 |
| Leu | Tyr | Ser | Ala | Phe | Ser | Ser | Leu | Gly | Cys | Leu | Glu | Gly | Asp | Thr | Tyr | |
| | | 35 | | | | | 40 | | | | | 45 | | | | |

| GTG | GTC | AAC | CCG | AAT | GCA | TTG | GCC | ATT | CTG | GAG | GAG | ATC | AAC | TAC | AAG | 192 |
| Val | Val | Asn | Pro | Asn | Ala | Leu | Ala | Ile | Leu | Glu | Glu | Ile | Asn | Tyr | Lys | |
| | 50 | | | | | 55 | | | | | 60 | | | | | |

| CTC | ACC | TAT | GAG | GAC | CAA | ACA | CTG | CGC | ACC | TTT | CGA | CGG | GCC | ATT | GGA | 240 |
| Leu | Thr | Tyr | Glu | Asp | Gln | Thr | Leu | Arg | Thr | Phe | Arg | Arg | Ala | Ile | Gly | |
| 65 | | | | | 70 | | | | | 75 | | | | | 80 | |

| TTT | GGC | CAG | AAT | GTG | AGG | TCA | GAC | CTG | ATA | CCG | CTG | CTG | GAG | AAT | GCC | 288 |
| Phe | Gly | Gln | Asn | Val | Arg | Ser | Asp | Leu | Ile | Pro | Leu | Leu | Glu | Asn | Ala | |
| | | | | 85 | | | | | 90 | | | | | 95 | | |

| AAG | GAT | GAT | GCG | GTC | CTG | GAG | TCG | GTC | ATC | CGG | ATA | CTC | GTC | AAT | CTG | 336 |
| Lys | Asp | Asp | Ala | Val | Leu | Glu | Ser | Val | Ile | Arg | Ile | Leu | Val | Asn | Leu | |
| | | | 100 | | | | | 105 | | | | | 110 | | | |

| ACG | GTG | CCG | GTG | GAG | TGC | CTC | TTC | TCC | GTG | GAC | GTG | ATG | TAC | CGC | ACG | 384 |
| Thr | Val | Pro | Val | Glu | Cys | Leu | Phe | Ser | Val | Asp | Val | Met | Tyr | Arg | Thr | |
| | | 115 | | | | | 120 | | | | | 125 | | | | |

| GAT | GTG | GGT | CGC | CAC | ACC | ATC | TTC | GAG | CTG | AAT | AAG | CTG | CTG | TAC | ACC | 432 |
| Asp | Val | Gly | Arg | His | Thr | Ile | Phe | Glu | Leu | Asn | Lys | Leu | Leu | Tyr | Thr | |
| | 130 | | | | | 135 | | | | | 140 | | | | | |

| AGC | AAG | GAA | GCA | TTT | ACC | GAG | GCC | AGG | AGC | ACC | AAG | AGC | GTG | GTG | GAG | 480 |
| Ser | Lys | Glu | Ala | Phe | Thr | Glu | Ala | Arg | Ser | Thr | Lys | Ser | Val | Val | Glu | |
| 145 | | | | | 150 | | | | | 155 | | | | | 160 | |

| TAC | ATG | AAA | CAC | ATA | CTG | GAG | TCG | GAC | CCT | AAG | CTG | TCG | CCG | CAC | AAA | 528 |
| Tyr | Met | Lys | His | Ile | Leu | Glu | Ser | Asp | Pro | Lys | Leu | Ser | Pro | His | Lys | |
| | | | | 165 | | | | | 170 | | | | | 175 | | |

| TGC | GAT | CAA | ATC | AAC | AAC | TGT | CTG | CTG | CTG | CTG | AGA | AAT | ATC | CTG | CAC | 576 |
| Cys | Asp | Gln | Ile | Asn | Asn | Cys | Leu | Leu | Leu | Leu | Arg | Asn | Ile | Leu | His | |
| | | | 180 | | | | | 185 | | | | | 190 | | | |

| ATT | CCA | GAG | ACG | CAT | GCC | CAT | TGC | GTG | ATG | CCC | ATG | ATG | CAG | TCG | ATG | 624 |
| Ile | Pro | Glu | Thr | His | Ala | His | Cys | Val | Met | Pro | Met | Met | Gln | Ser | Met | |
| | | 195 | | | | | 200 | | | | | 205 | | | | |

| CCG | CAT | GGC | ATC | TCC | ATG | CAG | AAC | ACG | ATC | TTG | TGG | AAT | CTC | TTC | ATC | 672 |
| Pro | His | Gly | Ile | Ser | Met | Gln | Asn | Thr | Ile | Leu | Trp | Asn | Leu | Phe | Ile | |
| | 210 | | | | | 215 | | | | | 220 | | | | | |

| CAG | AGC | ATC | GAC | AAG | TTA | CTC | CTG | TAT | CTG | ATG | ACC | TGT | CCG | CAG | AGA | 720 |
| Gln | Ser | Ile | Asp | Lys | Leu | Leu | Leu | Tyr | Leu | Met | Thr | Cys | Pro | Gln | Arg | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| GCC | TTC | TGG | GGA | GTG | ACC | ATG | GTG | CAA | CTG | ATT | GCT | TTG | ATC | TAC | AAG | 768 |
| Ala | Phe | Trp | Gly | Val 245 | Thr | Met | Val | Gln 250 | Leu | Ile | Ala | Leu | Ile 255 | Tyr | Lys | |
| GAT | CAG | CAT | GGC | AGT | GGC | GAT | TCC | AGC | CCC | ATG | CTG | ACC | TCT | GAT | CCC | 816 |
| Asp | Gln | His | Gly 260 | Ser | Gly | Asp | Ser | Ser 265 | Pro | Met | Leu | Thr | Ser 270 | Asp | Pro | |
| ACC | TCC | GAT | TCC | TCG | GAC | AAC | GGC | AGC | AAT | GGC | CGT | GGC | ATG | GGC | GGT | 864 |
| Thr | Ser | Asp 275 | Ser | Ser | Asp | Asn | Gly 280 | Ser | Asn | Gly | Arg | Gly 285 | Met | Gly | Gly | |
| GGC | ATG | CGG | GAA | GGA | ACA | GCG | GCC | ACT | TTG | CAG | GAG | GTC | AGC | CGC | AAG | 912 |
| Gly | Met 290 | Arg | Glu | Gly | Thr 295 | Ala | Ala | Thr | Leu | Gln 300 | Glu | Val | Ser | Arg | Lys | |
| GGT | CAG | GAG | TAT | CAG | AAC | GCC | ATG | GCC | AGA | GTG | CCA | GCG | GAT | AAG | CCC | 960 |
| Gly 305 | Gln | Glu | Tyr | Gln | Asn 310 | Ala | Met | Ala | Arg | Val 315 | Pro | Ala | Asp | Lys | Pro 320 | |
| GAT | GGC | TCC | GAA | GAG | GCC | AGC | GAT | ATG | ACG | GGG | AAC | GAC | AGC | GAG | CAG | 1008 |
| Asp | Gly | Ser | Glu | Glu 325 | Ala | Ser | Asp | Met | Thr 330 | Gly | Asn | Asp | Ser | Glu 335 | Gln | |
| CCT | GGA | TCG | CCG | GAG | CAA | TCG | CAG | CCC | GCC | GGC | GAG | TCC | ATG | GAT | GAT | 1056 |
| Pro | Gly | Ser | Pro 340 | Glu | Gln | Ser | Gln | Pro 345 | Ala | Gly | Glu | Ser | Met 350 | Asp | Asp | |
| GGA | GAT | TAC | GAG | GAC | CAG | AGA | CAC | AGG | CAA | CTG | AAC | GAG | CAT | GGC | GAA | 1104 |
| Gly | Asp | Tyr 355 | Glu | Asp | Gln | Arg | His 360 | Arg | Gln | Leu | Asn | Glu 365 | His | Gly | Glu | |
| GAG | GAT | GAA | GAT | GAG | GAC | GAA | GTG | GAG | GAG | GAA | GAG | TAC | CTA | CAA | TTG | 1152 |
| Glu | Asp 370 | Glu | Asp | Glu | Asp | Glu 375 | Val | Glu | Glu | Glu | Glu 380 | Tyr | Leu | Gln | Leu | |
| GGC | CCA | GCC | TCG | GAG | CCC | CTT | AAC | TTA | ACA | CAA | CAA | CCA | GCT | GAC | AAG | 1200 |
| Gly 385 | Pro | Ala | Ser | Glu | Pro 390 | Leu | Asn | Leu | Thr | Gln 395 | Gln | Pro | Ala | Asp | Lys 400 | |
| GTC | AAC | AAC | ACT | ACC | AAC | CCA | ACG | TCC | AGT | GCG | CCA | CAA | GGC | TGC | CTG | 1248 |
| Val | Asn | Asn | Thr | Thr 405 | Asn | Pro | Thr | Ser | Ser 410 | Ala | Pro | Gln | Gly | Cys 415 | Leu | |
| GGC | AAT | GAG | CCA | TTC | AAG | CCA | CCA | CCT | CCT | CTG | CCA | GTC | AGA | GCC | TCC | 1296 |
| Gly | Asn | Glu | Pro 420 | Phe | Lys | Pro | Pro | Pro 425 | Pro | Leu | Pro | Val | Arg 430 | Ala | Ser | |
| ACC | TCG | GCA | CAC | GCT | CAA | ATG | CAG | AAG | TTC | AAC | GAA | TCR | TCC | TAC | GCG | 1344 |
| Thr | Ser | Ala | His 435 | Ala | Gln | Met | Gln | Lys 440 | Phe | Asn | Glu | Ser | Ser 445 | Tyr | Ala | |
| TCC | CAC | GTA | TCT | GCG | GTC | AAA | TTG | GGC | CAA | AAG | TCC | CCA | CAT | GCC | GGC | 1392 |
| Ser | His 450 | Val | Ser | Ala | Val | Lys 455 | Leu | Gly | Gln | Lys | Ser 460 | Pro | His | Ala | Gly | |
| CAG | CTC | CAG | CTG | ACC | AAG | GGC | AAG | TGT | TGT | CCA | CAG | AAG | CGG | GAA | TGC | 1440 |
| Gln | Leu | Gln 465 | Leu | Thr | Lys | Gly 470 | Lys | Cys | Cys | Pro | Gln 475 | Lys | Arg | Glu | Cys 480 | |
| CCC | TCC | TCG | CAG | TCG | GAG | CTA | TCG | GAT | TGC | GGT | TAT | GGC | ACC | CAG | GTG | 1488 |
| Pro | Ser | Ser | Gln 485 | Ser | Glu | Leu | Ser | Asp 490 | Cys | Gly | Tyr | Gly | Thr 495 | Gln | Val | |
| GAA | AAT | CAG | GAA | TCC | ATT | TCC | ACC | TCC | AGC | AAC | GAT | GAT | GAT | GGG | CCG | 1536 |
| Glu | Asn | Gln | Glu 500 | Ser | Ile | Ser | Thr | Ser 505 | Ser | Asn | Asp | Asp | Asp 510 | Gly | Pro | |
| CAG | GGC | AAG | CCG | CAG | CAC | CAG | AAG | CCT | CCG | TGT | AAC | ACG | AAG | CCA | CGG | 1584 |
| Gln | Gly | Lys 515 | Pro | Gln | His | Gln | Lys 520 | Pro | Pro | Cys | Asn | Thr 525 | Lys | Pro | Arg | |
| AAT | AAA | CCA | CGG | ACG | ATT | ATG | TCG | CCA | ATG | GAC | AAA | AAG | GAG | CTT | AGA | 1632 |
| Asn | Lys | Pro 530 | Arg | Thr | Ile | Met | Ser 535 | Pro | Met | Asp | Lys | Lys 540 | Glu | Leu | Arg | |
| CGC | AAA | AAA | CTG | GTC | AAG | CGC | AGC | AAA | AGC | AGC | CTC | ATC | AAC | ATG | AAG | 1680 |
| Arg 545 | Lys | Lys | Leu | Val | Lys 550 | Arg | Ser | Lys | Ser | Ser 555 | Leu | Ile | Asn | Met | Lys 560 | |

| | | | | | | | | | | | | | | | | |
|---|---|---|---|---|---|---|---|---|---|---|---|---|---|---|---|---|
| GGT | CTG | GTA | CAG | CAC | ACC | CCC | ACC | GAT | GAT | GAC | ATC | TCC | AAT | CTG | CTG | 1728 |
| Gly | Leu | Val | Gln | His | Thr | Pro | Thr | Asp | Asp | Asp | Ile | Ser | Asn | Leu | Leu | |
| | | | 565 | | | | 570 | | | | | | | 575 | | |
| AAG | GAA | TTC | ACC | GTG | GAT | TTC | CTC | CTC | AAG | GGT | TAC | AGC | TAT | CTG | GTG | 1776 |
| Lys | Glu | Phe | Thr | Val | Asp | Phe | Leu | Leu | Lys | Gly | Tyr | Ser | Tyr | Leu | Val | |
| | | | 580 | | | | 585 | | | | | | 590 | | | |
| GAG | GAA | CTG | CAC | ATG | CAA | CTG | CTT | TCC | AAT | GCG | AAG | GTG | CCC | ATT | GAC | 1824 |
| Glu | Glu | Leu | His | Met | Gln | Leu | Leu | Ser | Asn | Ala | Lys | Val | Pro | Ile | Asp | |
| | | 595 | | | | | 600 | | | | | 605 | | | | |
| ACA | TCG | CAC | TTC | TTT | TGG | CTG | GTA | ACC | TAC | TTC | CTG | AAG | TTT | GCC | GCC | 1872 |
| Thr | Ser | His | Phe | Phe | Trp | Leu | Val | Thr | Tyr | Phe | Leu | Lys | Phe | Ala | Ala | |
| | 610 | | | | | 615 | | | | | 620 | | | | | |
| CAA | CTG | GAG | CTG | GAT | ATG | GAG | CAC | ATC | GAC | ACT | ATT | CTC | ACC | TAC | GAT | 1920 |
| Gln | Leu | Glu | Leu | Asp | Met | Glu | His | Ile | Asp | Thr | Ile | Leu | Thr | Tyr | Asp | |
| 625 | | | | 630 | | | | 635 | | | | | | 640 | | |
| GTT | TTG | AGC | TAC | TTG | ACC | TAT | GAG | GGT | GTG | TCC | CTA | TGT | GAG | CAA | CTG | 1968 |
| Val | Leu | Ser | Tyr | Leu | Thr | Tyr | Glu | Gly | Val | Ser | Leu | Cys | Glu | Gln | Leu | |
| | | | | 645 | | | | | 650 | | | | | 655 | | |
| GAA | CTG | AAT | GCC | CGA | CAG | GAG | GGC | AGT | GAC | CTG | AAG | CCC | TAT | CTA | AGG | 2016 |
| Glu | Leu | Asn | Ala | Arg | Gln | Glu | Gly | Ser | Asp | Leu | Lys | Pro | Tyr | Leu | Arg | |
| | | | 660 | | | | 665 | | | | | 670 | | | | |
| CGA | ATG | CAC | TTG | GTG | GTG | ACG | GCC | ATC | CGG | GAG | TTC | CTC | CAG | GCC | ATT | 2064 |
| Arg | Met | His | Leu | Val | Val | Thr | Ala | Ile | Arg | Glu | Phe | Leu | Gln | Ala | Ile | |
| | | 675 | | | | | 680 | | | | | 685 | | | | |
| GAT | ACG | TAC | AAC | AAA | GTG | ACT | CAT | CTG | AAC | GAG | GAC | GAC | AAA | GCC | CAT | 2112 |
| Asp | Thr | Tyr | Asn | Lys | Val | Thr | His | Leu | Asn | Glu | Asp | Asp | Lys | Ala | His | |
| | 690 | | | | | 695 | | | | | 700 | | | | | |
| TTG | AGG | CAG | CTT | CAG | CTG | CAG | ATT | AGC | GAA | ATG | TCC | GAT | CTG | AGG | TGC | 2160 |
| Leu | Arg | Gln | Leu | Gln | Leu | Gln | Ile | Ser | Glu | Met | Ser | Asp | Leu | Arg | Cys | |
| 705 | | | | 710 | | | | | 715 | | | | | 720 | | |
| CTT | TTT | GTG | CTT | CTG | CTG | AGG | CGT | TTC | AAT | CCC | AGC | ATT | CAT | TCC | AAG | 2208 |
| Leu | Phe | Val | Leu | Leu | Leu | Arg | Arg | Phe | Asn | Pro | Ser | Ile | His | Ser | Lys | |
| | | | | 725 | | | | 730 | | | | | | 735 | | |
| CAG | TAT | CTT | CAG | GAT | CTG | GTG | GTT | ACC | AAT | CAC | ATC | CTC | CTA | CTC | ATT | 2256 |
| Gln | Tyr | Leu | Gln | Asp | Leu | Val | Val | Thr | Asn | His | Ile | Leu | Leu | Leu | Ile | |
| | | | 740 | | | | | 745 | | | | | 750 | | | |
| CTG | GAC | AGT | TCG | GCC | AAA | CTT | GGT | GGA | TGT | CAA | ACC | ATT | CGC | CTG | TCG | 2304 |
| Leu | Asp | Ser | Ser | Ala | Lys | Leu | Gly | Gly | Cys | Gln | Thr | Ile | Arg | Leu | Ser | |
| | | 755 | | | | | 760 | | | | | 765 | | | | |
| GAG | CAC | ATA | ACA | CAG | TTT | GCC | ACG | CTG | GAG | GTG | ATG | CAC | TAC | TAT | GGC | 2352 |
| Glu | His | Ile | Thr | Gln | Phe | Ala | Thr | Leu | Glu | Val | Met | His | Tyr | Tyr | Gly | |
| | 770 | | | | | 775 | | | | | 780 | | | | | |
| ATT | CTG | TTG | GAG | GAC | TTC | AAC | AAC | AAC | GGA | GAG | TTT | GTC | AAT | GAC | TGC | 2400 |
| Ile | Leu | Leu | Glu | Asp | Phe | Asn | Asn | Asn | Gly | Glu | Phe | Val | Asn | Asp | Cys | |
| 785 | | | | | 790 | | | | | 795 | | | | | 800 | |
| ATC | TTC | ACC | ATG | ATG | CAT | CAC | ATC | GGT | GGC | GAT | CTG | GGC | CAG | ATT | GGG | 2448 |
| Ile | Phe | Thr | Met | Met | His | His | Ile | Gly | Gly | Asp | Leu | Gly | Gln | Ile | Gly | |
| | | | | 805 | | | | | 810 | | | | | 815 | | |
| GTT | CTA | TTT | CAA | CCA | ATT | ATT | TTG | AAA | ACC | TAT | TCA | AGA | ATT | TGG | GAA | 2496 |
| Val | Leu | Phe | Gln | Pro | Ile | Ile | Leu | Lys | Thr | Tyr | Ser | Arg | Ile | Trp | Glu | |
| | | | 820 | | | | | 825 | | | | | 830 | | | |
| GCG | GAC | TAT | GAA | CTG | TGC | GAT | GAC | TGG | TCT | GAT | CTT | ATC | GAG | TAT | GTG | 2544 |
| Ala | Asp | Tyr | Glu | Leu | Cys | Asp | Asp | Trp | Ser | Asp | Leu | Ile | Glu | Tyr | Val | |
| | | 835 | | | | | 840 | | | | | 845 | | | | |
| ATT | CAC | AAG | TTC | ATG | AAT | ACT | CCT | CCG | AAG | TCG | CCA | CTC | ACC | ATT | CCT | 2592 |
| Ile | His | Lys | Phe | Met | Asn | Thr | Pro | Pro | Lys | Ser | Pro | Leu | Thr | Ile | Pro | |
| | 850 | | | | | 855 | | | | | 860 | | | | | |
| ACA | ACT | TCC | TTG | ACG | GAA | ATG | ACC | AAG | GAA | CAC | AAC | CAG | GAG | CAT | ACC | 2640 |
| Thr | Thr | Ser | Leu | Thr | Glu | Met | Thr | Lys | Glu | His | Asn | Gln | Glu | His | Thr | |
| 865 | | | | | 870 | | | | | 875 | | | | | 880 | |

| | | | | | | | | | | | | | | | | |
|---|---|---|---|---|---|---|---|---|---|---|---|---|---|---|---|---|
| GTT | TGC | TCT | TGG | TCG | CAG | GAG | GAA | ATG | GAC | ACA | CTT | TAT | TGG | TAT | TAT | 2688 |
| Val | Cys | Ser | Trp | Ser 885 | Gln | Glu | Glu | Met 890 | Asp | Thr | Leu | Tyr | Trp | Tyr 895 | Tyr | |
| GTG | CAG | AGC | AAG | AAG | AAC | AAC | GAT | ATT | GTG | GGA | AAG | ATA | GTT | AAG | CTC | 2736 |
| Val | Gln | Ser | Lys 900 | Lys | Asn | Asn | Asp | Ile 905 | Val | Gly | Lys | Ile | Val 910 | Lys | Leu | |
| TTC | AGC | AAC | AAC | GGC | AAC | AAG | CTG | AAA | ACC | AGG | ATT | TCT | ATT | ATC | CAA | 2784 |
| Phe | Ser | Asn 915 | Asn | Gly | Asn | Lys | Leu | Lys 920 | Thr | Arg | Ile | Ser | Ile 925 | Ile | Gln | |
| CAA | CTT | TTG | CAA | CAA | GAC | ATT | ATC | ACC | CTG | TTG | GAA | TAC | GAT | GAC | CTG | 2832 |
| Gln | Leu | Leu 930 | Gln | Gln | Asp | Ile | Ile 935 | Thr | Leu | Leu | Glu | Tyr 940 | Asp | Asp | Leu | |
| ATG | AAG | TTC | GAG | GAT | GCG | GAG | TAT | CAG | AGA | ACT | TTG | CTG | ACA | ACT | CCC | 2880 |
| Met 945 | Lys | Phe | Glu | Asp | Ala 950 | Glu | Tyr | Gln | Arg | Thr 955 | Leu | Leu | Thr | Thr | Pro 960 | |
| ACT | TCC | GCA | ACA | ACA | GAG | TCT | GGA | ATT | GAG | ATT | AAG | GAG | TGC | GCC | TAC | 2928 |
| Thr | Ser | Ala | Thr | Thr 965 | Glu | Ser | Gly | Ile | Glu 970 | Ile | Lys | Glu | Cys | Ala 975 | Tyr | |
| GGC | AAA | CCC | TCA | GAT | GAT | GTT | CAG | ATC | CTG | CTG | GAC | CTG | ATC | ATT | AAG | 2976 |
| Gly | Lys | Pro | Ser 980 | Asp | Asp | Val | Gln | Ile 985 | Leu | Leu | Asp | Leu | Ile 990 | Ile | Lys | |
| GAA | AAC | AAG | GCG | CAG | CAT | TTG | TTA | TGG | CTG | CAA | AGG | ATC | CTC | ATT | GAG | 3024 |
| Glu | Asn | Lys 995 | Ala | Gln | His | Leu | Leu 1000 | Trp | Leu | Gln | Arg | Ile 1005 | Leu | Ile | Glu | |
| TGC | TGC | TTC | GTT | AAA | CTG | ACC | CTG | CGG | AGT | GGT | CTC | AAG | GTT | CCG | GAA | 3072 |
| Cys | Cys 1010 | Phe | Val | Lys | Leu | Thr 1015 | Leu | Arg | Ser | Gly | Leu 1020 | Lys | Val | Pro | Glu | |
| GGC | GAT | CAC | ATC | ATG | GAG | CCG | GTG | GCC | TAC | CAC | TGC | ATC | TGC | AAG | CAG | 3120 |
| Gly | Asp | His | Ile | Met | Glu | Pro | Val | Ala | Tyr | His | Cys | Ile | Cys | Lys | Gln | |
| 1025 | | | | 1030 | | | | | 1035 | | | | | | 1040 | |
| AAG | TCC | ATT | CCG | GTG | GTG | CAG | TGG | AAC | AAC | GAG | CAA | TCC | ACT | ACG | ATG | 3168 |
| Lys | Ser | Ile | Pro | Val 1045 | Val | Gln | Trp | Asn | Asn 1050 | Glu | Gln | Ser | Thr | Thr 1055 | Met | |
| CTG | TAC | CAG | CCT | TTT | GTT | CTC | CTG | CTC | CAC | AAG | CTG | GGC | ATT | CAG | CTG | 3216 |
| Leu | Tyr | Gln | Pro 1060 | Phe | Val | Leu | Leu | Leu 1065 | His | Lys | Leu | Gly | Ile 1070 | Gln | Leu | |
| CCG | GCG | GAC | GCG | GGC | TCG | ATC | TTC | GCC | AGA | ATT | CCG | GAC | TAC | TGG | ACA | 3264 |
| Pro | Ala | Asp | Ala | Gly | Ser | Ile | Phe | Ala | Arg | Ile | Pro | Asp | Tyr | Trp | Thr | |
| | | 1075 | | | | | 1080 | | | | | 1085 | | | | |
| CCG | GAG | ACA | ATG | TAC | GGA | CTC | GCC | AAA | AAG | CTG | GGA | CCG | CTG | GAC | AAA | 3312 |
| Pro | Glu | Thr | Met | Tyr | Gly | Leu | Ala | Lys | Lys | Leu | Gly | Pro | Leu | Asp | Lys | |
| | 1090 | | | | | 1095 | | | | | 1100 | | | | | |
| CGT | GAG | TTA | AAG | TCA | ACC | ACA | GAA | AAA | AAC | AAC | CCA | TTT | GTC | ATT | CCA | 3360 |
| Arg | Glu | Leu | Lys | Ser | Thr | Thr | Glu | Lys | Asn | Asn | Pro | Phe | Val | Ile | Pro | |
| 1105 | | | | | 1110 | | | | | 1115 | | | | | 1120 | |
| CAA | AGG | TGA | | | | | | | | | | | | | | 3369 |
| Gln | Arg | * | | | | | | | | | | | | | | |

( 2 ) INFORMATION FOR SEQ ID NO:3:

( i ) SEQUENCE CHARACTERISTICS:
        ( A ) LENGTH: 1122 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Met | Ser | Arg | Val | Arg | Gln | Leu | His | Asn | His | Ile | Trp | Asn | Asn | Asn |
| 1 | | | | 5 | | | | | 10 | | | | | 15 |
| Phe | Asp | Lys | Val | Lys | Ser | Val | Met | Asp | Trp | Leu | Leu | Ala | Thr | Pro | Gln |
| | | | 20 | | | | | 25 | | | | | 30 | | |

-continued

```
Leu Tyr Ser Ala Phe Ser Ser Leu Gly Cys Leu Glu Gly Asp Thr Tyr
         35                  40                  45
Val Val Asn Pro Asn Ala Leu Ala Ile Leu Glu Glu Ile Asn Tyr Lys
         50                  55                  60
Leu Thr Tyr Glu Asp Gln Thr Leu Arg Thr Phe Arg Arg Ala Ile Gly
 65                  70                  75                  80
Phe Gly Gln Asn Val Arg Ser Asp Leu Ile Pro Leu Leu Glu Asn Ala
                 85                  90                  95
Lys Asp Asp Ala Val Leu Glu Ser Val Ile Arg Ile Leu Val Asn Leu
            100                 105                 110
Thr Val Pro Val Glu Cys Leu Phe Ser Val Asp Val Met Tyr Arg Thr
            115                 120                 125
Asp Val Gly Arg His Thr Ile Phe Glu Leu Asn Lys Leu Leu Tyr Thr
    130                 135                 140
Ser Lys Glu Ala Phe Thr Glu Ala Arg Ser Thr Lys Ser Val Val Glu
145                 150                 155                 160
Tyr Met Lys His Ile Leu Glu Ser Asp Pro Lys Leu Ser Pro His Lys
                165                 170                 175
Cys Asp Gln Ile Asn Asn Cys Leu Leu Leu Arg Asn Ile Leu His
            180                 185                 190
Ile Pro Glu Thr His Ala His Cys Val Met Pro Met Met Gln Ser Met
        195                 200                 205
Pro His Gly Ile Ser Met Gln Asn Thr Ile Leu Trp Asn Leu Phe Ile
    210                 215                 220
Gln Ser Ile Asp Lys Leu Leu Leu Tyr Leu Met Thr Cys Pro Gln Arg
225                 230                 235                 240
Ala Phe Trp Gly Val Thr Met Val Gln Leu Ile Ala Leu Ile Tyr Lys
                245                 250                 255
Asp Gln His Gly Ser Gly Asp Ser Ser Pro Met Leu Thr Ser Asp Pro
            260                 265                 270
Thr Ser Asp Ser Ser Asp Asn Gly Ser Asn Gly Arg Gly Met Gly Gly
        275                 280                 285
Gly Met Arg Glu Gly Thr Ala Ala Thr Leu Gln Glu Val Ser Arg Lys
    290                 295                 300
Gly Gln Glu Tyr Gln Asn Ala Met Ala Arg Val Pro Ala Asp Lys Pro
305                 310                 315                 320
Asp Gly Ser Glu Glu Ala Ser Asp Met Thr Gly Asn Asp Ser Glu Gln
                325                 330                 335
Pro Gly Ser Pro Glu Gln Ser Gln Pro Ala Gly Glu Ser Met Asp Asp
            340                 345                 350
Gly Asp Tyr Glu Asp Gln Arg His Arg Gln Leu Asn Glu His Gly Glu
        355                 360                 365
Glu Asp Glu Asp Glu Asp Glu Val Glu Glu Glu Glu Tyr Leu Gln Leu
    370                 375                 380
Gly Pro Ala Ser Glu Pro Leu Asn Leu Thr Gln Gln Pro Ala Asp Lys
385                 390                 395                 400
Val Asn Asn Thr Thr Asn Pro Thr Ser Ser Ala Pro Gln Gly Cys Leu
                405                 410                 415
Gly Asn Glu Pro Phe Lys Pro Pro Pro Leu Pro Val Arg Ala Ser
            420                 425                 430
Thr Ser Ala His Ala Gln Met Gln Lys Phe Asn Glu Ser Ser Tyr Ala
        435                 440                 445
Ser His Val Ser Ala Val Lys Leu Gly Gln Lys Ser Pro His Ala Gly
```

```
                    450                         455                         460
Gln   Leu   Gln   Leu   Thr   Lys   Gly   Lys   Cys   Cys   Pro   Gln   Lys   Arg   Glu   Cys
465                     470                     475                         480

Pro   Ser   Ser   Gln   Ser   Glu   Leu   Ser   Asp   Cys   Gly   Tyr   Gly   Thr   Gln   Val
                  485                     490                          495

Glu   Asn   Gln   Glu   Ser   Ile   Ser   Thr   Ser   Ser   Asn   Asp   Asp   Asp   Gly   Pro
                  500                     505                          510

Gln   Gly   Lys   Pro   Gln   His   Gln   Lys   Pro   Pro   Cys   Asn   Thr   Lys   Pro   Arg
            515                     520                          525

Asn   Lys   Pro   Arg   Thr   Ile   Met   Ser   Pro   Met   Asp   Lys   Lys   Glu   Leu   Arg
      530                           535                     540

Arg   Lys   Lys   Leu   Val   Lys   Arg   Ser   Lys   Ser   Ser   Leu   Ile   Asn   Met   Lys
545                     550                     555                               560

Gly   Leu   Val   Gln   His   Thr   Pro   Thr   Asp   Asp   Ile   Ser   Asn   Leu   Leu
                        565                     570                     575

Lys   Glu   Phe   Thr   Val   Asp   Phe   Leu   Leu   Lys   Gly   Tyr   Ser   Tyr   Leu   Val
                  580                     585                          590

Glu   Glu   Leu   His   Met   Gln   Leu   Leu   Ser   Asn   Ala   Lys   Val   Pro   Ile   Asp
            595                     600                          605

Thr   Ser   His   Phe   Phe   Trp   Leu   Val   Thr   Tyr   Phe   Leu   Lys   Phe   Ala   Ala
610                           615                           620

Gln   Leu   Glu   Leu   Asp   Met   Glu   His   Ile   Asp   Thr   Ile   Leu   Thr   Tyr   Asp
625                           630                     635                           640

Val   Leu   Ser   Tyr   Leu   Thr   Tyr   Glu   Gly   Val   Ser   Leu   Cys   Glu   Gln   Leu
                        645                     650                     655

Glu   Leu   Asn   Ala   Arg   Gln   Glu   Gly   Ser   Asp   Leu   Lys   Pro   Tyr   Leu   Arg
                  660                     665                     670

Arg   Met   His   Leu   Val   Val   Thr   Ala   Ile   Arg   Glu   Phe   Leu   Gln   Ala   Ile
            675                     680                     685

Asp   Thr   Tyr   Asn   Lys   Val   Thr   His   Leu   Asn   Glu   Asp   Asp   Lys   Ala   His
      690                     695                     700

Leu   Arg   Gln   Leu   Gln   Leu   Gln   Ile   Ser   Glu   Met   Ser   Asp   Leu   Arg   Cys
705                     710                     715                               720

Leu   Phe   Val   Leu   Leu   Leu   Arg   Arg   Phe   Asn   Pro   Ser   Ile   His   Ser   Lys
                        725                     730                          735

Gln   Tyr   Leu   Gln   Asp   Leu   Val   Val   Thr   Asn   His   Ile   Leu   Leu   Leu   Ile
                  740                     745                          750

Leu   Asp   Ser   Ser   Ala   Lys   Leu   Gly   Gly   Cys   Gln   Thr   Ile   Arg   Leu   Ser
            755                     760                     765

Glu   His   Ile   Thr   Gln   Phe   Ala   Thr   Leu   Glu   Val   Met   His   Tyr   Tyr   Gly
      770                     775                     780

Ile   Leu   Leu   Glu   Asp   Phe   Asn   Asn   Asn   Gly   Glu   Phe   Val   Asn   Asp   Cys
785                           790                     795                           800

Ile   Phe   Thr   Met   Met   His   His   Ile   Gly   Gly   Asp   Leu   Gly   Gln   Ile   Gly
                        805                     810                           815

Val   Leu   Phe   Gln   Pro   Ile   Ile   Leu   Lys   Thr   Tyr   Ser   Arg   Ile   Trp   Glu
                  820                     825                     830

Ala   Asp   Tyr   Glu   Leu   Cys   Asp   Asp   Trp   Ser   Asp   Leu   Ile   Glu   Tyr   Val
            835                     840                     845

Ile   His   Lys   Phe   Met   Asn   Thr   Pro   Pro   Lys   Ser   Pro   Leu   Thr   Ile   Pro
850                           855                     860

Thr   Thr   Ser   Leu   Thr   Glu   Met   Thr   Lys   Glu   His   Asn   Gln   Glu   His   Thr
865                     870                     875                               880
```

Val Cys Ser Trp Ser Gln Glu Glu Met Asp Thr Leu Tyr Trp Tyr Tyr
            885                 890                 895

Val Gln Ser Lys Lys Asn Asn Asp Ile Val Gly Lys Ile Val Lys Leu
            900                 905                 910

Phe Ser Asn Asn Gly Asn Lys Leu Lys Thr Arg Ile Ser Ile Ile Gln
        915                 920                 925

Gln Leu Leu Gln Gln Asp Ile Ile Thr Leu Leu Glu Tyr Asp Asp Leu
    930                 935                 940

Met Lys Phe Glu Asp Ala Glu Tyr Gln Arg Thr Leu Leu Thr Thr Pro
945                 950                 955                 960

Thr Ser Ala Thr Thr Glu Ser Gly Ile Glu Ile Lys Glu Cys Ala Tyr
                965                 970                 975

Gly Lys Pro Ser Asp Asp Val Gln Ile Leu Leu Asp Leu Ile Ile Lys
            980                 985                 990

Glu Asn Lys Ala Gln His Leu Leu Trp Leu Gln Arg Ile Leu Ile Glu
        995                 1000                1005

Cys Cys Phe Val Lys Leu Thr Leu Arg Ser Gly Leu Lys Val Pro Glu
    1010                1015                1020

Gly Asp His Ile Met Glu Pro Val Ala Tyr His Cys Ile Cys Lys Gln
1025                1030                1035                1040

Lys Ser Ile Pro Val Val Gln Trp Asn Asn Glu Gln Ser Thr Thr Met
                1045                1050                1055

Leu Tyr Gln Pro Phe Val Leu Leu Leu His Lys Leu Gly Ile Gln Leu
            1060                1065                1070

Pro Ala Asp Ala Gly Ser Ile Phe Ala Arg Ile Pro Asp Tyr Trp Thr
        1075                1080                1085

Pro Glu Thr Met Tyr Gly Leu Ala Lys Lys Leu Gly Pro Leu Asp Lys
    1090                1095                1100

Arg Glu Leu Lys Ser Thr Thr Glu Lys Asn Asn Pro Phe Val Ile Pro
1105                1110                1115                1120

Gln Arg ( 2 ) INFORMATION FOR SEQ ID NO:4:

( i ) SEQUENCE CHARACTERISTICS:
        ( A ) LENGTH: 4170 base pairs
        ( B ) TYPE: nucleic acid
        ( C ) STRANDEDNESS: double
        ( D ) TOPOLOGY: linear ( i i ) MOLECULE TYPE: cDNA
        ( A ) DESCRIPTION: tim cDNA sequence wherein R at position 1335

( i i i ) HYPOTHETICAL: NO ( i v ) ANTI-SENSE: NO ( v i ) ORIGINAL SOURCE:
        ( A ) ORGANISM: Drosophila melanogaster ( i x ) FEATURE:
        ( A ) NAME/KEY: CDS
        ( B ) LOCATION: 1..4170

( x i ) SEQUENCE DESCRIPTION: SEQ ID NO:4:

ATG AGC AGA GTT AGG CAG CTC CAC AAT CAC ATC TGG AAT AAT CAG AAC    48
Met Ser Arg Val Arg Gln Leu His Asn His Ile Trp Asn Asn Gln Asn
 1               5                  10                  15

TTT GAT AAA GTG AAA TCG GTT ATG GAC TGG TTA CTA GCA ACT CCG CAG    96
Phe Asp Lys Val Lys Ser Val Met Asp Trp Leu Leu Ala Thr Pro Gln
            20                  25                  30

| | | | | | | | | | | | | | | | | |
|---|---|---|---|---|---|---|---|---|---|---|---|---|---|---|---|---|
| TTG | TAC | AGC | GCG | TTC | TCC | TCC | TTG | GGT | TGC | TTG | GAG | GGC | GAT | ACC | TAT | 144 |
| Leu | Tyr | Ser | Ala | Phe | Ser | Ser | Leu | Gly | Cys | Leu | Glu | Gly | Asp | Thr | Tyr | |
| | | 35 | | | | | 40 | | | | | 45 | | | | |
| GTG | GTC | AAC | CCG | AAT | GCA | TTG | GCC | ATT | CTG | GAG | GAG | ATC | AAC | TAC | AAG | 192 |
| Val | Val | Asn | Pro | Asn | Ala | Leu | Ala | Ile | Leu | Glu | Glu | Ile | Asn | Tyr | Lys | |
| | 50 | | | | 55 | | | | | 60 | | | | | | |
| CTC | ACC | TAT | GAG | GAC | CAA | ACA | CTG | CGC | ACC | TTT | CGA | CGG | GCC | ATT | GGA | 240 |
| Leu | Thr | Tyr | Glu | Asp | Gln | Thr | Leu | Arg | Thr | Phe | Arg | Arg | Ala | Ile | Gly | |
| 65 | | | | | 70 | | | | | 75 | | | | | 80 | |
| TTT | GGC | CAG | AAT | GTG | AGG | TCA | GAC | CTG | ATA | CCG | CTG | CTG | GAG | AAT | GCC | 288 |
| Phe | Gly | Gln | Asn | Val | Arg | Ser | Asp | Leu | Ile | Pro | Leu | Leu | Glu | Asn | Ala | |
| | | | | 85 | | | | | 90 | | | | | 95 | | |
| AAG | GAT | GAT | GCG | GTC | CTG | GAG | TCG | GTC | ATC | CGG | ATA | CTC | GTC | AAT | CTG | 336 |
| Lys | Asp | Asp | Ala | Val | Leu | Glu | Ser | Val | Ile | Arg | Ile | Leu | Val | Asn | Leu | |
| | | | 100 | | | | | 105 | | | | | 110 | | | |
| ACG | GTG | CCG | GTG | GAG | TGC | CTC | TTC | TCC | GTG | GAC | GTG | ATG | TAC | CGC | ACG | 384 |
| Thr | Val | Pro | Val | Glu | Cys | Leu | Phe | Ser | Val | Asp | Val | Met | Tyr | Arg | Thr | |
| | | 115 | | | | | 120 | | | | | 125 | | | | |
| GAT | GTG | GGT | CGC | CAC | ACC | ATC | TTC | GAG | CTG | AAT | AAG | CTG | CTG | TAC | ACC | 432 |
| Asp | Val | Gly | Arg | His | Thr | Ile | Phe | Glu | Leu | Asn | Lys | Leu | Leu | Tyr | Thr | |
| | 130 | | | | 135 | | | | | 140 | | | | | | |
| AGC | AAG | GAA | GCA | TTT | ACC | GAG | GCC | AGG | AGC | ACC | AAG | AGC | GTG | GTG | GAG | 480 |
| Ser | Lys | Glu | Ala | Phe | Thr | Glu | Ala | Arg | Ser | Thr | Lys | Ser | Val | Val | Glu | |
| 145 | | | | | 150 | | | | | 155 | | | | | 160 | |
| TAC | ATG | AAA | CAC | ATA | CTG | GAG | TCG | GAC | CCT | AAG | CTG | TCG | CCG | CAC | AAA | 528 |
| Tyr | Met | Lys | His | Ile | Leu | Glu | Ser | Asp | Pro | Lys | Leu | Ser | Pro | His | Lys | |
| | | | | 165 | | | | | 170 | | | | | 175 | | |
| TGC | GAT | CAA | ATC | AAC | AAC | TGT | CTG | CTG | CTG | AGA | AAT | ATC | CTG | CAC | | 576 |
| Cys | Asp | Gln | Ile | Asn | Asn | Cys | Leu | Leu | Leu | Arg | Asn | Ile | Leu | His | | |
| | | | 180 | | | | | 185 | | | | | 190 | | | |
| ATT | CCA | GAG | ACG | CAT | GCC | CAT | TGC | GTG | ATG | CCC | ATG | ATG | CAG | TCG | ATG | 624 |
| Ile | Pro | Glu | Thr | His | Ala | His | Cys | Val | Met | Pro | Met | Met | Gln | Ser | Met | |
| | | 195 | | | | | 200 | | | | | 205 | | | | |
| CCG | CAT | GGC | ATC | TCC | ATG | CAG | AAC | ACG | ATC | TTG | TGG | AAT | CTC | TTC | ATC | 672 |
| Pro | His | Gly | Ile | Ser | Met | Gln | Asn | Thr | Ile | Leu | Trp | Asn | Leu | Phe | Ile | |
| | 210 | | | | 215 | | | | | 220 | | | | | | |
| CAG | AGC | ATC | GAC | AAG | TTA | CTC | CTG | TAT | CTG | ATG | ACC | TGT | CCG | CAG | AGA | 720 |
| Gln | Ser | Ile | Asp | Lys | Leu | Leu | Leu | Tyr | Leu | Met | Thr | Cys | Pro | Gln | Arg | |
| 225 | | | | | 230 | | | | | 235 | | | | | 240 | |
| GCC | TTC | TGG | GGA | GTG | ACC | ATG | GTG | CAA | CTG | ATT | GCT | TTG | ATC | TAC | AAG | 768 |
| Ala | Phe | Trp | Gly | Val | Thr | Met | Val | Gln | Leu | Ile | Ala | Leu | Ile | Tyr | Lys | |
| | | | | 245 | | | | | 250 | | | | | 255 | | |
| GAT | CAG | CAT | GGC | AGT | GGC | GAT | TCC | AGC | CCC | ATG | CTG | ACC | TCT | GAT | CCC | 816 |
| Asp | Gln | His | Gly | Ser | Gly | Asp | Ser | Ser | Pro | Met | Leu | Thr | Ser | Asp | Pro | |
| | | | 260 | | | | | 265 | | | | | 270 | | | |
| ACC | TCC | GAT | TCC | TCG | GAC | AAC | GGC | AGC | AAT | GGC | CGT | GGC | ATG | GGC | GGT | 864 |
| Thr | Ser | Asp | Ser | Ser | Asp | Asn | Gly | Ser | Asn | Gly | Arg | Gly | Met | Gly | Gly | |
| | | 275 | | | | | 280 | | | | | 285 | | | | |
| GGC | ATG | CGG | GAA | GGA | ACA | GCG | GCC | ACT | TTG | CAG | GAG | GTC | AGC | CGC | AAG | 912 |
| Gly | Met | Arg | Glu | Gly | Thr | Ala | Ala | Thr | Leu | Gln | Glu | Val | Ser | Arg | Lys | |
| | 290 | | | | 295 | | | | | 300 | | | | | | |
| GGT | CAG | GAG | TAT | CAG | AAC | GCC | ATG | GCC | AGA | GTG | CCA | GCG | GAT | AAG | CCC | 960 |
| Gly | Gln | Glu | Tyr | Gln | Asn | Ala | Met | Ala | Arg | Val | Pro | Ala | Asp | Lys | Pro | |
| 305 | | | | | 310 | | | | | 315 | | | | | 320 | |
| GAT | GGC | TCC | GAA | GAG | GCC | AGC | GAT | ATG | ACG | GGG | AAC | GAC | AGC | GAG | CAG | 1008 |
| Asp | Gly | Ser | Glu | Glu | Ala | Ser | Asp | Met | Thr | Gly | Asn | Asp | Ser | Glu | Gln | |
| | | | | 325 | | | | | 330 | | | | | 335 | | |
| CCT | GGA | TCG | CCG | GAG | CAA | TCG | CAG | CCC | GCC | GGC | GAG | TCC | ATG | GAT | GAT | 1056 |
| Pro | Gly | Ser | Pro | Glu | Gln | Ser | Gln | Pro | Ala | Gly | Glu | Ser | Met | Asp | Asp | |
| | | | 340 | | | | | 345 | | | | | 350 | | | |

| | | | | | | | | | | | | | | | | |
|---|---|---|---|---|---|---|---|---|---|---|---|---|---|---|---|---|
| GGA | GAT | TAC | GAG | GAC | CAG | AGA | CAC | AGG | CAA | CTG | AAC | GAG | CAT | GGC | GAA | 1104 |
| Gly | Asp | Tyr | Glu | Asp | Gln | Arg | His | Arg | Gln | Leu | Asn | Glu | His | Gly | Glu | |
| | | 355 | | | 360 | | | | | | 365 | | | | | |
| GAG | GAT | GAA | GAT | GAG | GAC | GAA | GTG | GAG | GAG | GAA | GAG | TAC | CTA | CAA | TTG | 1152 |
| Glu | Asp | Glu | Asp | Glu | Asp | Glu | Val | Glu | Glu | Glu | Glu | Tyr | Leu | Gln | Leu | |
| 370 | | | | | 375 | | | | | | 380 | | | | | |
| GGC | CCA | GCC | TCG | GAG | CCC | CTT | AAC | TTA | ACA | CAA | CAA | CCA | GCT | GAC | AAG | 1200 |
| Gly | Pro | Ala | Ser | Glu | Pro | Leu | Asn | Leu | Thr | Gln | Gln | Pro | Ala | Asp | Lys | |
| 385 | | | | | 390 | | | | | 395 | | | | | 400 | |
| GTC | AAC | AAC | ACT | ACC | AAC | CCA | ACG | TCC | AGT | GCG | CCA | CAA | GGC | TGC | CTG | 1248 |
| Val | Asn | Asn | Thr | Thr | Asn | Pro | Thr | Ser | Ser | Ala | Pro | Gln | Gly | Cys | Leu | |
| | | | | 405 | | | | | 410 | | | | | 415 | | |
| GGC | AAT | GAG | CCA | TTC | AAG | CCA | CCA | CCT | CCT | CTG | CCA | GTC | AGA | GCC | TCC | 1296 |
| Gly | Asn | Glu | Pro | Phe | Lys | Pro | Pro | Pro | Pro | Leu | Pro | Val | Arg | Ala | Ser | |
| | | | 420 | | | | | 425 | | | | | 430 | | | |
| ACC | TCG | GCA | CAC | GCT | CAA | ATG | CAG | AAG | TTC | AAC | GAA | TCR | TCC | TAC | GCG | 1344 |
| Thr | Ser | Ala | His | Ala | Gln | Met | Gln | Lys | Phe | Asn | Glu | Ser | Ser | Tyr | Ala | |
| | | 435 | | | | 440 | | | | | 445 | | | | | |
| TCC | CAC | GTA | TCT | GCG | GTC | AAA | TTG | GGC | CAA | AAG | TCC | CCA | CAT | GCC | GGC | 1392 |
| Ser | His | Val | Ser | Ala | Val | Lys | Leu | Gly | Gln | Lys | Ser | Pro | His | Ala | Gly | |
| | 450 | | | | | 455 | | | | | 460 | | | | | |
| CAG | CTC | CAG | CTG | ACC | AAG | GGC | AAG | TGT | TGT | CCA | CAG | AAG | CGG | GAA | TGC | 1440 |
| Gln | Leu | Gln | Leu | Thr | Lys | Gly | Lys | Cys | Cys | Pro | Gln | Lys | Arg | Glu | Cys | |
| 465 | | | | | 470 | | | | | 475 | | | | | 480 | |
| CCC | TCC | TCG | CAG | TCG | GAG | CTA | TCG | GAT | TGC | GGT | TAT | GGC | ACC | CAG | GTG | 1488 |
| Pro | Ser | Ser | Gln | Ser | Glu | Leu | Ser | Asp | Cys | Gly | Tyr | Gly | Thr | Gln | Val | |
| | | | | 485 | | | | | 490 | | | | | 495 | | |
| GAA | AAT | CAG | GAA | TCC | ATT | TCC | ACC | TCC | AGC | AAC | GAC | GAT | GAT | GGG | CCG | 1536 |
| Glu | Asn | Gln | Glu | Ser | Ile | Ser | Thr | Ser | Ser | Asn | Asp | Asp | Asp | Gly | Pro | |
| | | | 500 | | | | | 505 | | | | | 510 | | | |
| CAG | GGC | AAG | CCG | CAG | CAC | CAG | AAG | CCT | CCG | TGT | AAC | ACG | AAG | CCA | CGG | 1584 |
| Gln | Gly | Lys | Pro | Gln | His | Gln | Lys | Pro | Pro | Cys | Asn | Thr | Lys | Pro | Arg | |
| | | 515 | | | | 520 | | | | | 525 | | | | | |
| AAT | AAA | CCA | CGG | ACG | ATT | ATG | TCG | CCA | ATG | GAC | AAA | AAG | GAG | CTT | AGA | 1632 |
| Asn | Lys | Pro | Arg | Thr | Ile | Met | Ser | Pro | Met | Asp | Lys | Lys | Glu | Leu | Arg | |
| | 530 | | | | | 535 | | | | 540 | | | | | | |
| CGC | AAA | AAA | CTG | GTC | AAG | CGC | AGC | AAA | AGC | AGC | CTC | ATC | AAC | ATG | AAG | 1680 |
| Arg | Lys | Lys | Leu | Val | Lys | Arg | Ser | Lys | Ser | Ser | Leu | Ile | Asn | Met | Lys | |
| 545 | | | | | 550 | | | | | 555 | | | | | 560 | |
| GGT | CTG | GTA | CAG | CAC | ACC | CCC | ACC | GAT | GAT | GAC | ATC | TCC | AAT | CTG | CTG | 1728 |
| Gly | Leu | Val | Gln | His | Thr | Pro | Thr | Asp | Asp | Asp | Ile | Ser | Asn | Leu | Leu | |
| | | | | 565 | | | | | 570 | | | | | 575 | | |
| AAG | GAA | TTC | ACC | GTG | GAT | TTC | CTC | CTC | AAG | GGT | TAC | AGC | TAT | CTG | GTG | 1776 |
| Lys | Glu | Phe | Thr | Val | Asp | Phe | Leu | Leu | Lys | Gly | Tyr | Ser | Tyr | Leu | Val | |
| | | | 580 | | | | | 585 | | | | | 590 | | | |
| GAG | GAA | CTG | CAC | ATG | CAA | CTG | CTT | TCC | AAT | GCG | AAG | GTG | CCC | ATT | GAC | 1824 |
| Glu | Glu | Leu | His | Met | Gln | Leu | Leu | Ser | Asn | Ala | Lys | Val | Pro | Ile | Asp | |
| | | 595 | | | | 600 | | | | | 605 | | | | | |
| ACA | TCG | CAC | TTC | TTT | TGG | CTG | GTA | ACC | TAC | TTC | CTG | AAG | TTT | GCC | GCC | 1872 |
| Thr | Ser | His | Phe | Phe | Trp | Leu | Val | Thr | Tyr | Phe | Leu | Lys | Phe | Ala | Ala | |
| | 610 | | | | | 615 | | | | | 620 | | | | | |
| CAA | CTG | GAG | CTG | GAT | ATG | GAG | CAC | ATC | GAC | ACT | ATT | CTC | ACC | TAC | GAT | 1920 |
| Gln | Leu | Glu | Leu | Asp | Met | Glu | His | Ile | Asp | Thr | Ile | Leu | Thr | Tyr | Asp | |
| 625 | | | | | 630 | | | | | 635 | | | | | 640 | |
| GTT | TTG | AGC | TAC | TTG | ACC | TAT | GAG | GGT | GTG | TCC | CTA | TGT | GAG | CAA | CTG | 1968 |
| Val | Leu | Ser | Tyr | Leu | Thr | Tyr | Glu | Gly | Val | Ser | Leu | Cys | Glu | Gln | Leu | |
| | | | | 645 | | | | | 650 | | | | | 655 | | |
| GAA | CTG | AAT | GCC | CGA | CAG | GAG | GGC | AGT | GAC | CTG | AAG | CCC | TAT | CTA | AGG | 2016 |
| Glu | Leu | Asn | Ala | Arg | Gln | Glu | Gly | Ser | Asp | Leu | Lys | Pro | Tyr | Leu | Arg | |
| | | | 660 | | | | | 665 | | | | | 670 | | | |

| | | | | | | | | | | | | | | | | |
|---|---|---|---|---|---|---|---|---|---|---|---|---|---|---|---|---|
| CGA | ATG | CAC | TTG | GTG | GTG | ACG | GCC | ATC | CGG | GAG | TTC | CTC | CAG | GCC | ATT | 2064 |
| Arg | Met | His | Leu | Val | Val | Thr | Ala | Ile | Arg | Glu | Phe | Leu | Gln | Ala | Ile | |
| | 675 | | | | | 680 | | | | | 685 | | | | | |
| GAT | ACG | TAC | AAC | AAA | GTG | ACT | CAT | CTG | AAC | GAG | GAC | GAC | AAA | GCC | CAT | 2112 |
| Asp | Thr | Tyr | Asn | Lys | Val | Thr | His | Leu | Asn | Glu | Asp | Asp | Lys | Ala | His | |
| | 690 | | | | 695 | | | | | 700 | | | | | | |
| TTG | AGG | CAG | CTT | CAG | CTG | CAG | ATT | AGC | GAA | ATG | TCC | GAT | CTG | AGG | TGC | 2160 |
| Leu | Arg | Gln | Leu | Gln | Leu | Gln | Ile | Ser | Glu | Met | Ser | Asp | Leu | Arg | Cys | |
| 705 | | | | 710 | | | | | 715 | | | | | 720 | | |
| CTT | TTT | GTG | CTT | CTG | CTG | AGG | CGT | TTC | AAT | CCC | AGC | ATT | CAT | TCC | AAG | 2208 |
| Leu | Phe | Val | Leu | Leu | Leu | Arg | Arg | Phe | Asn | Pro | Ser | Ile | His | Ser | Lys | |
| | | | | 725 | | | | | 730 | | | | | 735 | | |
| CAG | TAT | CTT | CAG | GAT | CTG | GTG | GTT | ACC | AAT | CAC | ATC | CTC | CTA | CTC | ATT | 2256 |
| Gln | Tyr | Leu | Gln | Asp | Leu | Val | Val | Thr | Asn | His | Ile | Leu | Leu | Leu | Ile | |
| | | | 740 | | | | | 745 | | | | | 750 | | | |
| CTG | GAC | AGT | TCG | GCC | AAA | CTT | GGT | GGA | TGT | CAA | ACC | ATT | CGC | CTG | TCG | 2304 |
| Leu | Asp | Ser | Ser | Ala | Lys | Leu | Gly | Gly | Cys | Gln | Thr | Ile | Arg | Leu | Ser | |
| | | 755 | | | | | 760 | | | | | 765 | | | | |
| GAG | CAC | ATA | ACA | CAG | TTT | GCC | ACG | CTG | GAG | GTG | ATG | CAC | TAC | TAT | GGC | 2352 |
| Glu | His | Ile | Thr | Gln | Phe | Ala | Thr | Leu | Glu | Val | Met | His | Tyr | Tyr | Gly | |
| | 770 | | | | | 775 | | | | | 780 | | | | | |
| ATT | CTG | TTG | GAG | GAC | TTC | AAC | AAC | AAC | GGA | GAG | TTT | GTC | AAT | GAC | TGC | 2400 |
| Ile | Leu | Leu | Glu | Asp | Phe | Asn | Asn | Asn | Gly | Glu | Phe | Val | Asn | Asp | Cys | |
| 785 | | | | | 790 | | | | | 795 | | | | | 800 | |
| ATC | TTC | ACC | ATG | ATG | CAT | CAC | ATC | GGT | GGC | GAT | CTG | GGC | CAG | ATT | GGG | 2448 |
| Ile | Phe | Thr | Met | Met | His | His | Ile | Gly | Gly | Asp | Leu | Gly | Gln | Ile | Gly | |
| | | | | 805 | | | | | 810 | | | | | 815 | | |
| GTT | CTA | TTT | CAA | CCA | ATT | ATT | TTG | AAA | ACC | TAT | TCA | AGA | ATT | TGG | GAA | 2496 |
| Val | Leu | Phe | Gln | Pro | Ile | Ile | Leu | Lys | Thr | Tyr | Ser | Arg | Ile | Trp | Glu | |
| | | | 820 | | | | | 825 | | | | | 830 | | | |
| GCG | GAC | TAT | GAA | CTG | TGC | GAT | GAC | TGG | TCT | GAT | CTT | ATC | GAG | TAT | GTG | 2544 |
| Ala | Asp | Tyr | Glu | Leu | Cys | Asp | Asp | Trp | Ser | Asp | Leu | Ile | Glu | Tyr | Val | |
| | | 835 | | | | | 840 | | | | | 845 | | | | |
| ATT | CAC | AAG | TTC | ATG | AAT | ACT | CCT | CCG | AAG | TCG | CCA | CTC | ACC | ATT | CCT | 2592 |
| Ile | His | Lys | Phe | Met | Asn | Thr | Pro | Pro | Lys | Ser | Pro | Leu | Thr | Ile | Pro | |
| | 850 | | | | | 855 | | | | | 860 | | | | | |
| ACA | ACT | TCC | TTG | ACG | GAA | ATG | ACC | AAG | GAA | CAC | AAC | CAG | GAG | CAT | ACC | 2640 |
| Thr | Thr | Ser | Leu | Thr | Glu | Met | Thr | Lys | Glu | His | Asn | Gln | Glu | His | Thr | |
| 865 | | | | | 870 | | | | | 875 | | | | | 880 | |
| GTT | TGC | TCT | TGG | TCG | CAG | GAG | GAA | ATG | GAC | ACA | CTT | TAT | TGG | TAT | TAT | 2688 |
| Val | Cys | Ser | Trp | Ser | Gln | Glu | Glu | Met | Asp | Thr | Leu | Tyr | Trp | Tyr | Tyr | |
| | | | | 885 | | | | | 890 | | | | | 895 | | |
| GTG | CAG | AGC | AAG | AAG | AAC | AAC | GAT | ATT | GTG | GGA | AAG | ATA | GTT | AAG | CTC | 2736 |
| Val | Gln | Ser | Lys | Lys | Asn | Asn | Asp | Ile | Val | Gly | Lys | Ile | Val | Lys | Leu | |
| | | | 900 | | | | | 905 | | | | | 910 | | | |
| TTC | AGC | AAC | AAC | GGC | AAC | AAG | CTG | AAA | ACC | AGG | ATT | TCT | ATT | ATC | CAA | 2784 |
| Phe | Ser | Asn | Asn | Gly | Asn | Lys | Leu | Lys | Thr | Arg | Ile | Ser | Ile | Ile | Gln | |
| | | 915 | | | | | 920 | | | | | 925 | | | | |
| CAA | CTT | TTG | CAA | CAA | GAC | ATT | ATC | ACC | CTG | TTG | GAA | TAC | GAT | GAC | CTG | 2832 |
| Gln | Leu | Leu | Gln | Gln | Asp | Ile | Ile | Thr | Leu | Leu | Glu | Tyr | Asp | Asp | Leu | |
| | 930 | | | | | 935 | | | | | 940 | | | | | |
| ATG | AAG | TTC | GAG | GAT | GCG | GAG | TAT | CAG | AGA | ACT | TTG | CTG | ACA | ACT | CCC | 2880 |
| Met | Lys | Phe | Glu | Asp | Ala | Glu | Tyr | Gln | Arg | Thr | Leu | Leu | Thr | Thr | Pro | |
| 945 | | | | | 950 | | | | | 955 | | | | | 960 | |
| ACT | TCC | GCA | ACA | ACA | GAG | TCT | GGA | ATT | GAG | ATT | AAG | GAG | TGC | GCC | TAC | 2928 |
| Thr | Ser | Ala | Thr | Thr | Glu | Ser | Gly | Ile | Glu | Ile | Lys | Glu | Cys | Ala | Tyr | |
| | | | | 965 | | | | | 970 | | | | | 975 | | |
| GGC | AAA | CCC | TCA | GAT | GAT | GTT | CAG | ATC | CTG | CTG | GAC | CTG | ATC | ATT | AAG | 2976 |
| Gly | Lys | Pro | Ser | Asp | Asp | Val | Gln | Ile | Leu | Leu | Asp | Leu | Ile | Ile | Lys | |
| | | | 980 | | | | | 985 | | | | | 990 | | | |

```
GAA  AAC  AAG  GCG  CAG  CAT  TTG  TTA  TGG  CTG  CAA  AGG  ATC  CTC  ATT  GAG    3024
Glu  Asn  Lys  Ala  Gln  His  Leu  Leu  Trp  Leu  Gln  Arg  Ile  Leu  Ile  Glu
          995                      1000                     1005

TGC  TGC  TTC  GTT  AAA  CTG  ACC  CTG  CGG  AGT  GGT  CTC  AAG  GTT  CCG  GAA    3072
Cys  Cys  Phe  Val  Lys  Leu  Thr  Leu  Arg  Ser  Gly  Leu  Lys  Val  Pro  Glu
     1010                     1015                     1020

GGC  GAT  CAC  ATC  ATG  GAG  CCG  GTG  GCC  TAC  CAC  TGC  ATC  TGC  AAG  CAG    3120
Gly  Asp  His  Ile  Met  Glu  Pro  Val  Ala  Tyr  His  Cys  Ile  Cys  Lys  Gln
1025                     1030                     1035                     1040

AAG  TCC  ATT  CCG  GTG  GTG  CAG  TGG  AAC  AAC  GAG  CAA  TCC  ACT  ACG  ATG    3168
Lys  Ser  Ile  Pro  Val  Val  Gln  Trp  Asn  Asn  Glu  Gln  Ser  Thr  Thr  Met
                         1045                     1050                     1055

CTG  TAC  CAG  CCT  TTT  GTT  CTC  CTG  CTC  CAC  AAG  CTG  GGC  ATT  CAG  CTG    3216
Leu  Tyr  Gln  Pro  Phe  Val  Leu  Leu  Leu  His  Lys  Leu  Gly  Ile  Gln  Leu
               1060                     1065                     1070

CCG  GCG  GAC  GCG  GGC  TCG  ATC  TTC  GCC  AGA  ATT  CCG  GAC  TAC  TGG  ACA    3264
Pro  Ala  Asp  Ala  Gly  Ser  Ile  Phe  Ala  Arg  Ile  Pro  Asp  Tyr  Trp  Thr
          1075                     1080                     1085

CCG  GAG  ACA  ATG  TAC  GGA  CTC  GCC  AAA  AAG  CTG  GGA  CCG  CTG  GAC  AAA    3312
Pro  Glu  Thr  Met  Tyr  Gly  Leu  Ala  Lys  Lys  Leu  Gly  Pro  Leu  Asp  Lys
     1090                     1095                     1100

CTC  AAC  CTC  AAG  TTC  GAC  GCC  AGT  GAA  CTG  GAG  GAT  GCG  ACG  GCG  TCG    3360
Leu  Asn  Leu  Lys  Phe  Asp  Ala  Ser  Glu  Leu  Glu  Asp  Ala  Thr  Ala  Ser
1105                     1110                     1115                     1120

AGT  CCG  TCG  CGT  TAC  CAC  CAC  ACC  GGA  CCC  CGC  AAC  TCG  CTC  AGC  TCG    3408
Ser  Pro  Ser  Arg  Tyr  His  His  Thr  Gly  Pro  Arg  Asn  Ser  Leu  Ser  Ser
                         1125                     1130                     1135

GTA  AGC  AGC  CTG  GAC  GTG  GAT  CTC  GGC  GAT  ACC  GAG  GAG  CTG  GCC  CTT    3456
Val  Ser  Ser  Leu  Asp  Val  Asp  Leu  Gly  Asp  Thr  Glu  Glu  Leu  Ala  Leu
               1140                     1145                     1150

ATA  CCC  GAG  GTG  GAT  GCG  GCC  GTG  GAG  AAG  GCA  CAC  GCC  ATG  GCA  TCC    3504
Ile  Pro  Glu  Val  Asp  Ala  Ala  Val  Glu  Lys  Ala  His  Ala  Met  Ala  Ser
          1155                     1160                     1165

ACG  CCA  TCG  CCC  AGC  GAG  ATT  TTC  GCG  GTT  CCC  AAG  ACG  AAG  CAC  TGC    3552
Thr  Pro  Ser  Pro  Ser  Glu  Ile  Phe  Ala  Val  Pro  Lys  Thr  Lys  His  Cys
     1170                     1175                     1180

AAC  TCG  ATC  ATC  AGA  TAC  ACA  CCA  GAT  CCC  ACG  CCT  CCA  GTG  CCC  AAC    3600
Asn  Ser  Ile  Ile  Arg  Tyr  Thr  Pro  Asp  Pro  Thr  Pro  Pro  Val  Pro  Asn
1185                     1190                     1195                     1200

TGG  CTG  CAG  TTG  GTC  ATG  CGC  AGC  AAA  TGC  AAT  CAT  CGC  ACA  GGT  CCG    3648
Trp  Leu  Gln  Leu  Val  Met  Arg  Ser  Lys  Cys  Asn  His  Arg  Thr  Gly  Pro
                         1205                     1210                     1215

TCT  GGT  GAT  CCC  AGC  GAT  TGC  GTT  GGC  TCC  TCG  TCG  ACA  ACC  GTG  GAC    3696
Ser  Gly  Asp  Pro  Ser  Asp  Cys  Val  Gly  Ser  Ser  Ser  Thr  Thr  Val  Asp
               1220                     1225                     1230

GAT  GAG  GGA  TTT  GGC  AAG  TCC  ATC  AGT  GCA  GCC  ACT  TCG  CAG  GCG  GCG    3744
Asp  Glu  Gly  Phe  Gly  Lys  Ser  Ile  Ser  Ala  Ala  Thr  Ser  Gln  Ala  Ala
          1235                     1240                     1245

AGC  ACC  TCC  ATG  AGC  ACG  GTT  AAT  CCC  ACA  ACC  ACT  TTG  AGC  CTG  AAC    3792
Ser  Thr  Ser  Met  Ser  Thr  Val  Asn  Pro  Thr  Thr  Thr  Leu  Ser  Leu  Asn
     1250                     1255                     1260

ATG  CTA  AAC  ACC  TTC  ATG  GGA  AGC  CAC  AAC  GAG  AAC  AGC  AGC  AGT  TCT    3840
Met  Leu  Asn  Thr  Phe  Met  Gly  Ser  His  Asn  Glu  Asn  Ser  Ser  Ser  Ser
1265                     1270                     1275                     1280

GGT  TGC  GGG  GGC  ACC  GTC  TCC  TCC  CTG  TCC  ATG  GTG  GCT  CTG  ATG  AGC    3888
Gly  Cys  Gly  Gly  Thr  Val  Ser  Ser  Leu  Ser  Met  Val  Ala  Leu  Met  Ser
                         1285                     1290                     1295

ACC  GGC  GCG  GCA  GGC  GGA  GGA  GGT  AAC  ACC  TCC  GGG  CTG  GAA  ATG  GAT    3936
Thr  Gly  Ala  Ala  Gly  Gly  Gly  Gly  Asn  Thr  Ser  Gly  Leu  Glu  Met  Asp
               1300                     1305                     1310
```

| | | | | | | | | | | | | | | | | |
|---|---|---|---|---|---|---|---|---|---|---|---|---|---|---|---|---|
| GTG | GAC | GCC | TCC | ATG | AAG | TCC | TCG | TTC | GAG | CGG | CTG | GAG | GTA | AAC | GGA | 3984 |
| Val | Asp | Ala | Ser | Met | Lys | Ser | Ser | Phe | Glu | Arg | Leu | Glu | Val | Asn | Gly | |
| | | 1315 | | | | 1320 | | | | | 1325 | | | | | |
| TCG | CAC | TTC | TCG | CGG | GCC | AAC | AAC | TTG | GAC | CAG | GAG | TAC | AGT | GCC | ATG | 4032 |
| Ser | His | Phe | Ser | Arg | Ala | Asn | Asn | Leu | Asp | Gln | Glu | Tyr | Ser | Ala | Met | |
| | 1330 | | | | 1335 | | | | 1340 | | | | | | | |
| GTG | GCA | TCT | GTG | TAC | GAA | AAG | GAG | AAG | GAA | TTA | AAC | AGC | GAC | AAT | GTC | 4080 |
| Val | Ala | Ser | Val | Tyr | Glu | Lys | Glu | Lys | Glu | Leu | Asn | Ser | Asp | Asn | Val | |
| 1345 | | | | | 1350 | | | | 1355 | | | | | 1360 | | |
| TCT | TTG | GCC | TCG | GAC | CTG | ACC | AGA | ATG | TAT | GTG | AGC | GAT | GAG | GAC | GAT | 4128 |
| Ser | Leu | Ala | Ser | Asp | Leu | Thr | Arg | Met | Tyr | Val | Ser | Asp | Glu | Asp | Asp | |
| | | | | 1365 | | | | 1370 | | | | 1375 | | | | |
| CGA | CTT | GAG | CGA | ACC | GAG | ATC | CGG | GTG | CCC | CAC | TAT | CAC | TGA | | | 4170 |
| Arg | Leu | Glu | Arg | Thr | Glu | Ile | Arg | Val | Pro | His | Tyr | His | | | | |
| | | | 1380 | | | | 1385 | | | | 1390 | | | | | |

( 2 ) INFORMATION FOR SEQ ID NO:5:

( i ) SEQUENCE CHARACTERISTICS:
        ( A ) LENGTH: 1389 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| | | | | | | | | | | | | | | |
|---|---|---|---|---|---|---|---|---|---|---|---|---|---|---|
| Met | Ser | Arg | Val | Arg | Gln | Leu | His | Asn | His | Ile | Trp | Asn | Asn | Asn |
| 1 | | | | 5 | | | | | 10 | | | | | 15 |
| Phe | Asp | Lys | Val | Lys | Ser | Val | Met | Asp | Trp | Leu | Leu | Ala | Thr | Pro | Gln |
| | | | 20 | | | | | 25 | | | | | 30 | | |
| Leu | Tyr | Ser | Ala | Phe | Ser | Ser | Leu | Gly | Cys | Leu | Glu | Gly | Asp | Thr | Tyr |
| | | | 35 | | | | 40 | | | | | 45 | | | |
| Val | Val | Asn | Pro | Asn | Ala | Leu | Ala | Ile | Leu | Glu | Glu | Ile | Asn | Tyr | Lys |
| | 50 | | | | | 55 | | | | | 60 | | | | |
| Leu | Thr | Tyr | Glu | Asp | Gln | Thr | Leu | Arg | Thr | Phe | Arg | Arg | Ala | Ile | Gly |
| 65 | | | | | 70 | | | | | 75 | | | | | 80 |
| Phe | Gly | Gln | Asn | Val | Arg | Ser | Asp | Leu | Ile | Pro | Leu | Leu | Glu | Asn | Ala |
| | | | | 85 | | | | | 90 | | | | | 95 | |
| Lys | Asp | Asp | Ala | Val | Leu | Glu | Ser | Val | Ile | Arg | Ile | Leu | Val | Asn | Leu |
| | | | 100 | | | | | 105 | | | | | 110 | | |
| Thr | Val | Pro | Val | Glu | Cys | Leu | Phe | Ser | Val | Asp | Val | Met | Tyr | Arg | Thr |
| | | | 115 | | | | | 120 | | | | | 125 | | |
| Asp | Val | Gly | Arg | His | Thr | Ile | Phe | Glu | Leu | Asn | Lys | Leu | Leu | Tyr | Thr |
| | 130 | | | | | 135 | | | | | 140 | | | | |
| Ser | Lys | Glu | Ala | Phe | Thr | Glu | Ala | Arg | Ser | Thr | Lys | Ser | Val | Val | Glu |
| 145 | | | | | 150 | | | | | 155 | | | | | 160 |
| Tyr | Met | Lys | His | Ile | Leu | Glu | Ser | Asp | Pro | Lys | Leu | Ser | Pro | His | Lys |
| | | | | 165 | | | | | 170 | | | | | 175 | |
| Cys | Asp | Gln | Ile | Asn | Asn | Cys | Leu | Leu | Leu | Arg | Asn | Ile | Leu | His | |
| | | | 180 | | | | | 185 | | | | | 190 | | |
| Ile | Pro | Glu | Thr | His | Ala | His | Cys | Val | Met | Pro | Met | Gln | Ser | Met | |
| | | | 195 | | | | | 200 | | | | | 205 | | |
| Pro | His | Gly | Ile | Ser | Met | Gln | Asn | Thr | Ile | Leu | Trp | Asn | Leu | Phe | Ile |
| | | 210 | | | | | 215 | | | | | 220 | | | |
| Gln | Ser | Ile | Asp | Lys | Leu | Leu | Leu | Tyr | Leu | Met | Thr | Cys | Pro | Gln | Arg |
| 225 | | | | | 230 | | | | | 235 | | | | | 240 |
| Ala | Phe | Trp | Gly | Val | Thr | Met | Val | Gln | Leu | Ile | Ala | Leu | Ile | Tyr | Lys |
| | | | | 245 | | | | | 250 | | | | | 255 | |

-continued

| Asp | Gln | His | Gly | Ser | Gly | Asp | Ser | Ser | Pro | Met | Leu | Thr | Ser | Asp | Pro |
| | | | 260 | | | | 265 | | | | | 270 | | | |

| Thr | Ser | Asp | Ser | Ser | Asp | Asn | Ser | Asn | Gly | Arg | Gly | Met | Gly | Gly |
| | | 275 | | | | 280 | | | | 285 | | | | |

| Gly | Met | Arg | Glu | Gly | Thr | Ala | Thr | Leu | Gln | Glu | Val | Ser | Arg | Lys |
| | 290 | | | | | 295 | | | | 300 | | | | |

| Gly | Gln | Glu | Tyr | Gln | Asn | Ala | Met | Ala | Arg | Val | Pro | Ala | Asp | Lys | Pro |
| 305 | | | | | 310 | | | | 315 | | | | | | 320 |

| Asp | Gly | Ser | Glu | Glu | Ala | Ser | Asp | Met | Thr | Gly | Asn | Asp | Ser | Glu | Gln |
| | | | | 325 | | | | 330 | | | | | | 335 | |

| Pro | Gly | Ser | Pro | Glu | Gln | Ser | Gln | Pro | Ala | Gly | Glu | Ser | Met | Asp | Asp |
| | | | 340 | | | | 345 | | | | | 350 | | | |

| Gly | Asp | Tyr | Glu | Asp | Gln | Arg | His | Arg | Gln | Leu | Asn | Glu | His | Gly | Glu |
| | | 355 | | | | 360 | | | | | 365 | | | | |

| Glu | Asp | Glu | Asp | Glu | Asp | Val | Glu | Glu | Glu | Glu | Tyr | Leu | Gln | Leu |
| 370 | | | | | 375 | | | | 380 | | | | | |

| Gly | Pro | Ala | Ser | Glu | Pro | Leu | Asn | Leu | Thr | Gln | Gln | Pro | Ala | Asp | Lys |
| 385 | | | | | 390 | | | | 395 | | | | | | 400 |

| Val | Asn | Asn | Thr | Thr | Asn | Pro | Thr | Ser | Ser | Ala | Pro | Gln | Gly | Cys | Leu |
| | | | | 405 | | | | | 410 | | | | | 415 | |

| Gly | Asn | Glu | Pro | Phe | Lys | Pro | Pro | Pro | Leu | Pro | Val | Arg | Ala | Ser |
| | | | 420 | | | | 425 | | | | | 430 | | |

| Thr | Ser | Ala | His | Ala | Gln | Met | Gln | Lys | Phe | Asn | Glu | Ser | Ser | Tyr | Ala |
| | | | 435 | | | | 440 | | | | | 445 | | | |

| Ser | His | Val | Ser | Ala | Val | Lys | Leu | Gly | Gln | Lys | Ser | Pro | His | Ala | Gly |
| | | 450 | | | | 455 | | | | | 460 | | | | |

| Gln | Leu | Gln | Leu | Thr | Lys | Gly | Lys | Cys | Cys | Pro | Gln | Lys | Arg | Glu | Cys |
| 465 | | | | | 470 | | | | | 475 | | | | | 480 |

| Pro | Ser | Ser | Gln | Ser | Glu | Leu | Ser | Asp | Cys | Gly | Tyr | Gly | Thr | Gln | Val |
| | | | | 485 | | | | | 490 | | | | | 495 | |

| Glu | Asn | Gln | Glu | Ser | Ile | Ser | Thr | Ser | Ser | Asn | Asp | Asp | Gly | Pro |
| | | | 500 | | | | 505 | | | | | 510 | | |

| Gln | Gly | Lys | Pro | Gln | His | Gln | Lys | Pro | Pro | Cys | Asn | Thr | Lys | Pro | Arg |
| | | 515 | | | | 520 | | | | | 525 | | | | |

| Asn | Lys | Pro | Arg | Thr | Ile | Met | Ser | Pro | Met | Asp | Lys | Lys | Glu | Leu | Arg |
| | 530 | | | | 535 | | | | | 540 | | | | | |

| Arg | Lys | Lys | Leu | Val | Lys | Arg | Ser | Lys | Ser | Ser | Leu | Ile | Asn | Met | Lys |
| 545 | | | | | 550 | | | | | 555 | | | | | 560 |

| Gly | Leu | Val | Gln | His | Thr | Pro | Thr | Asp | Asp | Ile | Ser | Asn | Leu | Leu |
| | | | | 565 | | | | 570 | | | | | 575 | |

| Lys | Glu | Phe | Thr | Val | Asp | Phe | Leu | Leu | Lys | Gly | Tyr | Ser | Tyr | Leu | Val |
| | | | 580 | | | | | 585 | | | | | 590 | | |

| Glu | Glu | Leu | His | Met | Gln | Leu | Leu | Ser | Asn | Ala | Lys | Val | Pro | Ile | Asp |
| | | | 595 | | | | 600 | | | | | 605 | | | |

| Thr | Ser | His | Phe | Phe | Trp | Leu | Val | Thr | Tyr | Phe | Leu | Lys | Phe | Ala | Ala |
| | | 610 | | | | 615 | | | | | 620 | | | | |

| Gln | Leu | Glu | Leu | Asp | Met | Glu | His | Ile | Asp | Thr | Ile | Leu | Thr | Tyr | Asp |
| 625 | | | | | 630 | | | | | 635 | | | | | 640 |

| Val | Leu | Ser | Tyr | Leu | Thr | Tyr | Glu | Gly | Val | Ser | Leu | Cys | Glu | Gln | Leu |
| | | | | 645 | | | | | 650 | | | | | 655 | |

| Glu | Leu | Asn | Ala | Arg | Gln | Glu | Gly | Ser | Asp | Leu | Lys | Pro | Tyr | Leu | Arg |
| | | | | 660 | | | | | 665 | | | | | 670 | |

| Arg | Met | His | Leu | Val | Val | Thr | Ala | Ile | Arg | Glu | Phe | Leu | Gln | Ala | Ile |
| | | 675 | | | | | 680 | | | | | 685 | | | |

Asp Thr Tyr Asn Lys Val Thr His Leu Asn Glu Asp Lys Ala His
690                 695                 700

Leu Arg Gln Leu Gln Leu Gln Ile Ser Glu Met Ser Asp Leu Arg Cys
705                 710                 715                 720

Leu Phe Val Leu Leu Arg Arg Phe Asn Pro Ser Ile His Ser Lys
                725                 730                 735

Gln Tyr Leu Gln Asp Leu Val Val Thr Asn His Ile Leu Leu Ile
            740                 745                 750

Leu Asp Ser Ser Ala Lys Leu Gly Gly Cys Gln Thr Ile Arg Leu Ser
        755                 760                 765

Glu His Ile Thr Gln Phe Ala Thr Leu Glu Val Met His Tyr Tyr Gly
770                 775                 780

Ile Leu Leu Glu Asp Phe Asn Asn Asn Gly Glu Phe Val Asn Asp Cys
785                 790                 795                 800

Ile Phe Thr Met Met His His Ile Gly Gly Asp Leu Gly Gln Ile Gly
                805                 810                 815

Val Leu Phe Gln Pro Ile Ile Leu Lys Thr Tyr Ser Arg Ile Trp Glu
            820                 825                 830

Ala Asp Tyr Glu Leu Cys Asp Asp Trp Ser Asp Leu Ile Glu Tyr Val
        835                 840                 845

Ile His Lys Phe Met Asn Thr Pro Pro Lys Ser Pro Leu Thr Ile Pro
    850                 855                 860

Thr Thr Ser Leu Thr Glu Met Thr Lys Glu His Asn Gln Glu His Thr
865                 870                 875                 880

Val Cys Ser Trp Ser Gln Glu Glu Met Asp Thr Leu Tyr Trp Tyr Tyr
                885                 890                 895

Val Gln Ser Lys Lys Asn Asn Asp Ile Val Gly Lys Ile Val Lys Leu
            900                 905                 910

Phe Ser Asn Asn Gly Asn Lys Leu Lys Thr Arg Ile Ser Ile Ile Gln
        915                 920                 925

Gln Leu Leu Gln Gln Asp Ile Ile Thr Leu Leu Glu Tyr Asp Asp Leu
    930                 935                 940

Met Lys Phe Glu Asp Ala Glu Tyr Gln Arg Thr Leu Leu Thr Thr Pro
945                 950                 955                 960

Thr Ser Ala Thr Thr Glu Ser Gly Ile Glu Ile Lys Glu Cys Ala Tyr
                965                 970                 975

Gly Lys Pro Ser Asp Asp Val Gln Ile Leu Leu Asp Leu Ile Ile Lys
            980                 985                 990

Glu Asn Lys Ala Gln His Leu Leu Trp Leu Gln Arg Ile Leu Ile Glu
        995                 1000                1005

Cys Cys Phe Val Lys Leu Thr Leu Arg Ser Gly Leu Lys Val Pro Glu
    1010                1015                1020

Gly Asp His Ile Met Glu Pro Val Ala Tyr His Cys Ile Cys Lys Gln
1025                1030                1035                1040

Lys Ser Ile Pro Val Val Gln Trp Asn Asn Glu Gln Ser Thr Thr Met
                1045                1050                1055

Leu Tyr Gln Pro Phe Val Leu Leu Leu His Lys Leu Gly Ile Gln Leu
            1060                1065                1070

Pro Ala Asp Ala Gly Ser Ile Phe Ala Arg Ile Pro Asp Tyr Trp Thr
        1075                1080                1085

Pro Glu Thr Met Tyr Gly Leu Ala Lys Lys Leu Gly Pro Leu Asp Lys
    1090                1095                1100

Leu Asn Leu Lys Phe Asp Ala Ser Glu Leu Glu Asp Ala Thr Ala Ser

|      |      |      |      | 1105 |      |      |      |      | 1110 |      |      |      |      | 1115 |      |      |      |      | 1120 |
|---|---|---|---|---|---|---|---|---|---|---|---|---|---|---|---|---|---|---|---|

Ser Pro Ser Arg Tyr His His Thr Gly Pro Arg Asn Ser Leu Ser Ser
                     1125                     1130              1135

Val Ser Ser Leu Asp Val Asp Leu Gly Asp Thr Glu Glu Leu Ala Leu
                1140                   1145              1150

Ile Pro Glu Val Asp Ala Ala Val Glu Lys Ala His Ala Met Ala Ser
                1155                   1160              1165

Thr Pro Ser Pro Ser Glu Ile Phe Ala Val Pro Lys Thr Lys His Cys
    1170                   1175                   1180

Asn Ser Ile Ile Arg Tyr Thr Pro Asp Pro Thr Pro Pro Val Pro Asn
1185                   1190                   1195              1200

Trp Leu Gln Leu Val Met Arg Ser Lys Cys Asn His Arg Thr Gly Pro
                1205                   1210              1215

Ser Gly Asp Pro Ser Asp Cys Val Gly Ser Ser Ser Thr Thr Val Asp
            1220                   1225              1230

Asp Glu Gly Phe Gly Lys Ser Ile Ser Ala Ala Thr Ser Gln Ala Ala
            1235                   1240              1245

Ser Thr Ser Met Ser Thr Val Asn Pro Thr Thr Thr Leu Ser Leu Asn
    1250                   1255                   1260

Met Leu Asn Thr Phe Met Gly Ser His Asn Glu Asn Ser Ser Ser Ser
1265                   1270                   1275              1280

Gly Cys Gly Gly Thr Val Ser Ser Leu Ser Met Val Ala Leu Met Ser
            1285                   1290              1295

Thr Gly Ala Ala Gly Gly Gly Gly Asn Thr Ser Gly Leu Glu Met Asp
            1300                   1305              1310

Val Asp Ala Ser Met Lys Ser Ser Phe Glu Arg Leu Glu Val Asn Gly
            1315                   1320              1325

Ser His Phe Ser Arg Ala Asn Asn Leu Asp Gln Glu Tyr Ser Ala Met
    1330                   1335                   1340

Val Ala Ser Val Tyr Glu Lys Glu Lys Glu Leu Asn Ser Asp Asn Val
1345                   1350                   1355              1360

Ser Leu Ala Ser Asp Leu Thr Arg Met Tyr Val Ser Asp Glu Asp Asp
            1365                   1370              1375

Arg Leu Glu Arg Thr Glu Ile Arg Val Pro His Tyr His
            1380                   1385

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Drosophila melanogaster ( x i ) SEQUENCE DESCRIPTION: SEQ ID NO:6:

Lys Lys Glu Leu Arg Arg Lys Lys
  1              5

( 2 ) INFORMATION FOR SEQ ID NO:7:

( i ) SEQUENCE CHARACTERISTICS:

( A ) LENGTH: 30 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Drosophila melanogaster ( x i ) SEQUENCE DESCRIPTION: SEQ ID NO:7:

| Asp | Asp | Gly | Asp | Tyr | Glu | Asp | Gln | Arg | His | Arg | Gln | Leu | Asn | Glu | His |
|---|---|---|---|---|---|---|---|---|---|---|---|---|---|---|---|
| 1 | | | | 5 | | | | | 10 | | | | | 15 | |
| Gly | Glu | Glu | Asp | Glu | Asp | Glu | Asp | Glu | Val | Glu | Glu | Glu | Glu | | |
| | | | 20 | | | | 25 | | | | | 30 | | | |

( 2 ) INFORMATION FOR SEQ ID NO:8:

( i ) SEQUENCE CHARACTERISTICS:
( A ) LENGTH: 5192 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( x i ) SEQUENCE DESCRIPTION: SEQ ID NO:8:

```
AATTTCATCA GTGCATATAA CAGCACTGAA ACTATAACAC GATCTATTCT GCAAAGAAAC      60
CCAAAAAGTG CTCAGAAAAG CTCAATTGCT TAGAAACATA AACAATCAGC TTTAATTGTT     120
GATTGCAATT CGGCTAAAAC TAAAACTAAA ACAGTAAAAT TGTCTGCGAT AGAAAAAATT     180
TAAATAATTG TTACAGATAC CGCGCAAATG GCTAAGAAGT ACCTCAATGT TCGCAGTCGA     240
CAATGAGCAG AGTTAGGCAG CTCCACAATC ACATCTGGAA TAATCAGAAC TTTGATAAAG     300
TGAAATCGGT TATGGACTGG TTACTAGCAA CTCCGCAGTT GTACAGCGCG TTCTCCTCCT     360
TGGGTTGCTT GGAGGGCGAT ACCTATGTGG TCAACCCGAA TGCATTGGCC ATTCTGGAGG     420
AGATCAACTA CAAGCTCACC TATGAGGACC AAACACTGCG CACCTTTCGA CGGGCCATTG     480
GATTTGGCCA GAATGTGAGG TCAGACCTGA TACCGCTGCT GGAGAATGCC AAGGATGATG     540
CGGTCCTGGA GTCGGTCATC CGGATACTCG TCAATCTGAC GGTGCCGGTG GAGTGCCTCT     600
TCTCCGTGGA CGTGATGTAC CGCACGGATG TGGGTCGCCA CACCATCTTC GAGCTGAATA     660
AGCTGCTGTA CACCAGCAAG GAAGCATTTA CCGAGGCCAG GAGCACCAAG AGCGTGGTGG     720
AGTACATGAA ACACATACTG GAGTCGGACC CTAAGCTGTC GCCGCACAAA TGCGATCAAA     780
TCAACAACTG TCTGCTGCTG CTGAGAAATA TCCTGCACAT TCCAGAGACG CATGCCCATT     840
GCGTGATGCC CATGATGCAG TCGATGCCGC ATGGCATCTC CATGCAGAAC ACGATCTTGT     900
GGAATCTCTT CATCCAGAGC ATCGACAAGT TACTCCTGTA TCTGATGACC TGTCCGCAGA     960
GAGCCTTCTG GGGAGTGACC ATGGTGCAAC TGATTGCTTT GATCTACAAG GATCAGCATG    1020
GCAGTGGCGA TTCCAGCCCC ATGCTGACCT CTGATCCCAC CTCCGATTCC TCGGACAACG    1080
GCAGCAATGG CCGTGGCATG GGCGGTGGCA TGCGGGAAGG AACAGCGGCC ACTTTGCAGG    1140
AGGTCAGCCG CAAGGGTCAG GAGTATCAGA ACGCCATGGC CAGAGTGCCA GCGGATAAGC    1200
CCGATGGCTC CGAAGAGGCC AGCGATATGA CGGGGAACGA CAGCGAGCAG CCTGGATCGC    1260
CGGAGCAATC GCAGCCCGCC GGCGAGTCCA TGGATGATGG AGATTACGAG GACCAGAGAC    1320
```

```
ACAGGCAACT  GAACGAGCAT  GGCGAAGAGG  ATGAAGATGA  GGACGAAGTG  GAGGAGGAAG  1380

AGTACCTACA  ATTGGGCCCA  GCCTCGGAGC  CCCTTAACTT  AACACAACAA  CCAGCTGACA  1440

AGGTCAACAA  CACTACCAAC  CCAACGTCCA  GTGCGCCACA  AGGCTGCCTG  GGCAATGAGC  1500

CATTCAAGCC  ACCACCTCCT  CTGCCAGTCA  GAGCCTCCAC  CTCGGCACAC  GCTCAAATGC  1560

AGAAGTTCAA  CGAATCRTCC  TACGCGTCCC  ACGTATCTGC  GGTCAAATTG  GGCCAAAAGT  1620

CCCCACATGC  CGGCCAGCTC  CAGCTGACCA  AGGGCAAGTG  TTGTCCACAG  AAGCGGGAAT  1680

GCCCCTCCTC  GCAGTCGGAG  CTATCGGATT  GCGGTTATGG  CACCCAGGTG  GAAAATCAGG  1740

AATCCATTTC  CACCTCCAGC  AACGACGATG  ATGGGCCGCA  GGGCAAGCCG  CAGCACCAGA  1800

AGCCTCCGTG  TAACACGAAG  CCACGGAATA  AACCACGGAC  GATTATGTCG  CCAATGGACA  1860

AAAAGGAGCT  TAGACGCAAA  AAACTGGTCA  AGCGCAGCAA  AAGCAGCCTC  ATCAACATGA  1920

AGGGTCTGGT  ACAGCACACC  CCCACCGATG  ATGACATCTC  CAATCTGCTG  AAGGAATTCA  1980

CCGTGGATTT  CCTCCTCAAG  GGTTACAGCT  ATCTGGTGGA  GGAACTGCAC  ATGCAACTGC  2040

TTTCCAATGC  GAAGGTGCCC  ATTGACACAT  CGCACTTCTT  TTGGCTGGTA  ACCTACTTCC  2100

TGAAGTTTGC  CGCCCAACTG  GAGCTGGATA  TGGAGCACAT  CGACACTATT  CTCACCTACG  2160

ATGTTTTGAG  CTACTTGACC  TATGAGGGTG  TGTCCCTATG  TGAGCAACTG  GAACTGAATG  2220

CCCGACAGGA  GGGCAGTGAC  CTGAAGCCCT  ATCTAAGGCG  AATGCACTTG  GTGGTGACGG  2280

CCATCCGGGA  GTTCCTCCAG  GCCATTGATA  CGTACAACAA  AGTGACTCAT  CTGAACGAGG  2340

ACGACAAAGC  CCATTTGAGG  CAGCTTCAGC  TGCAGATTAG  CGAAATGTCC  GATCTGAGGT  2400

GCCTTTTTGT  GCTTCTGCTG  AGGCGTTTCA  ATCCCAGCAT  TCATTCCAAG  CAGTATCTTC  2460

AGGATCTGGT  GGTTACCAAT  CACATCCTCC  TACTCATTCT  GGACAGTTCG  GCCAAACTTG  2520

GTGGATGTCA  AACCATTCGC  CTGTCGGAGC  ACATAACACA  GTTTGCCACG  CTGGAGGTGA  2580

TGCACTACTA  TGGCATTCTG  TTGGAGGACT  TCAACAACAA  CGGAGAGTTT  GTCAATGACT  2640

GCATCTTCAC  CATGATGCAT  CACATCGGTG  GCGATCTGGG  CCAGATTGGG  GTTCTATTTC  2700

AACCAATTAT  TTTGAAAACC  TATTCAAGAA  TTTGGGAAGC  GGACTATGAA  CTGTGCGATG  2760

ACTGGTCTGA  TCTTATCGAG  TATGTGATTC  ACAAGTTCAT  GAATACTCCT  CCGAAGTCGC  2820

CACTCACCAT  TCCTACAACT  TCCTTGACGG  AAATGACCAA  GGAACACAAC  CAGGAGCATA  2880

CCGTTTGCTC  TTGGTCGCAG  GAGGAAATGG  ACACACTTTA  TTGGTATTAT  GTGCAGAGCA  2940

AGAAGAACAA  CGATATTGTG  GGAAAGATAG  TTAAGCTCTT  CAGCAACAAC  GGCAACAAGC  3000

TGAAAACCAG  GATTTCTATT  ATCCAACAAC  TTTTGCAACA  AGACATTATC  ACCCTGTTGG  3060

AATACGATGA  CCTGATGAAG  TTCGAGGATG  CGGAGTATCA  GAGAACTTTG  CTGACAACTC  3120

CCACTTCCGC  AACAACAGAG  TCTGGAATTG  AGATTAAGGA  GTGCGCCTAC  GGCAAACCCT  3180

CAGATGATGT  TCAGATCCTG  CTGGACCTGA  TCATTAAGGA  AAACAAGGCG  CAGCATTTGT  3240

TATGGCTGCA  AAGGATCCTC  ATTGAGTGCT  GCTTCGTTAA  ACTGACCCTG  CGGAGTGGTC  3300

TCAAGGTTCC  GGAAGGCGAT  CACATCATGG  AGCCGGTGGC  CTACCACTGC  ATCTGCAAGC  3360

AGAAGTCCAT  TCCGGTGGTG  CAGTGGAACA  ACGAGCAATC  CACTACGATG  CTGTACCAGC  3420

CTTTTGTTCT  CCTGCTCCAC  AAGCTGGGCA  TTCAGCTGCC  GGCGGACGCG  GGCTCGATCT  3480

TCGCCAGAAT  TCCGGACTAC  TGGACACCGG  AGACAATGTA  CGGACTCGCC  AAAAAGCTGG  3540

GACCGCTGGA  CAAACGTGAG  TTAAAGTCAA  CCACAGAAAA  AACAACCCA   TTTGTCATTC  3600

CACAAAGGTG  ATGTATATAC  CGTTATCAAC  AATTTTTGCT  CTCTCTCTGT  GTGAAATTTT  3660

GATCATGGGA  ATCTCGCCCG  AAACCGAATC  CAAATCCGTG  CTTCCATCCA  TTCCCATTCT  3720
```

-continued

| | | | | | | |
|---|---|---|---|---|---|---|
|CATTGTGTGT|CCGTCGGTGT|ATCTCGATAT|GCTGTGTGCC|TCTCTCCTTC|TCCTCCTTCT|3780|
|GGGCTCTTAT|AGTCAACCTC|AAGTTCGACG|CCAGTGAACT|GGAGGATGCG|ACGGCGTCGA|3840|
|GTCCGTCGCG|TTACCACCAC|ACCGGACCCC|GCAACTCGCT|CAGCTCGGTA|AGCAGCCTGG|3900|
|ACGTGGATCT|CGGCGATACC|GAGGAGCTGG|CCCTTATACC|CGAGGTGGAT|GCGGCCGTGG|3960|
|AGAAGGCACA|CGCCATGGCA|TCCACGCCAT|CGCCCAGCGA|GATTTTCGCG|GTTCCCAAGA|4020|
|CGAAGCACTG|CAACTCGATC|ATCAGATACA|CACCAGATCC|CACGCCTCCA|GTGCCCAACT|4080|
|GGCTGCAGTT|GGTCATGCGC|AGCAAATGCA|ATCATCGCAC|AGGTCCGTCT|GGTGATCCCA|4140|
|GCGATTGCGT|TGGCTCCTCG|TCGACAACCG|TGGACGATGA|GGGATTTGGC|AAGTCCATCA|4200|
|GTGCAGCCAC|TTCGCAGGCG|GCGAGCACCT|CCATGAGCAC|GGTTAATCCC|ACAACCACTT|4260|
|TGAGCCTGAA|CATGCTAAAC|ACCTTCATGG|GAAGCCACAA|CGAGAACAGC|AGCAGTTCTG|4320|
|GTTGCGGGGG|CACCGTCTCC|TCCCTGTCCA|TGGTGGCTCT|GATGAGCACC|GGCGCGGCAG|4380|
|GCGGAGGAGG|TAACACCTCC|GGGCTGGAAA|TGGATGTGGA|CGCCTCCATG|AAGTCCTCGT|4440|
|TCGAGCGGCT|GGAGGTAAAC|GGATCGCACT|TCTCGCGGGC|CAACAACTTG|GACCAGGAGT|4500|
|ACAGTGCCAT|GGTGGCATCT|GTGTACGAAA|AGGAGAAGGA|ATTAAACAGC|GACAATGTCT|4560|
|CTTTGGCCTC|GGACCTGACC|AGAATGTATG|TGAGCGATGA|GGACGATCGA|CTTGAGCGAA|4620|
|CCGAGATCCG|GGTGCCCCAC|TATCACTGAG|GATCCAATTC|CAATCGATCC|TAACCGATCC|4680|
|GATCCGATAT|CCGAGTTTTG|AGTGAGGCCC|ACCCAGCTGG|AAAGAATTGT|ACCTTAATCA|4740|
|ATCAAATCAA|GTAACGTTTA|ATATCACCCG|GCACAAGGAT|TGTACATTTT|ATGACCTCTA|4800|
|AATGCAAAAG|TATACCTGAT|TAATTAGCTA|CGCATAACGT|AAATTACGCG|GATAAACAAA|4860|
|AAAAGTCCAA|GCAGAAAGTG|AAGAAAAGTG|CATTATTTGG|TTAATGAATG|TGAGGCTCTG|4920|
|CAGACTGTTT|GCCTATGCTA|GCCCACTAGA|TACTCTTAAG|TTAACCTTAG|TTTCCAATCG|4980|
|TATTCGGTAT|ACCTACCTAC|CACATACACA|CACATACATG|TAAATGGGCA|GTTCCTGGTT|5040|
|CAAATAGTGC|AAATATACAC|ACATAAATCT|ATTTACACGT|TTAAGAAAGA|AGAGCGACCG|5100|
|GTGTCCATCC|ACCAAAAACC|ATCTGTATGT|ATATCCTTAG|TCATAAGTTA|TGCTTAGCAG|5160|
|TAATAAAGCT|TTCCCTGTAG|CCAAAAAAAA|AA| | |5192|

NUCLEAR LOCALIZATION FACTOR ASSOCIATED WITH CIRCADIAN RHYTHMS

CROSS-REFERENCE TO RELATED APPLICATIONS

The present application is a Continuation-In-Part of U.S. Ser. No. 08/552,354 filed Nov. 2, 1995, abandoned, which is a Continuation-In-Part of U.S. Ser. No. 08/442,214, filed May 16, 1995, abandoned, which is a Continuation-In-Part of U.S. Ser. No. 08/408,518, filed Mar. 20, 1995, abandoned, the disclosures of which are hereby incorporated by reference in their entireties. Applicants claim the benefits of these Applications under 35 U.S.C. § 120.

FINANCIAL SUPPORT

Research relating to the present invention has been funded in part by the National Science Foundation Science and Technology Center for Biological Timing, grant GM07982-09. The government may have certain rights in the invention.

TECHNICAL FIELD OF THE INVENTION

This invention relates to a factor involved in nuclear localization of proteins, and specifically to proteins involved in circadian rhythms. The invention also relates to mutants for the nuclear localization factor, an isolated DNA sequence and a purified nuclear localization factor protein.

BACKGROUND OF THE INVENTION

Circadian rhythms, found in most eukaryotes and some prokaryotes (Kay et al, *Cell*, 83:361 (1995)), are ~24 hour rhythms governed by an internal clock that functions autonomously, but can be entrained by environmental cycles of light or temperature. Circadian rhythms produced in constant darkness can also be reset by pulses of light. Such light pulses will shift the phase of the clock in different directions (advance or delay) and to varying degrees in a fashion that depends on the time of light exposure (Pittendrigh, in *Handbook of Behavioral Neurobiology*, 4, J. Aschoff, Ed., New York: Plenum, 1981, pp. 95–124).

Fruit flies show circadian regulation of several behaviors (Pittendrigh in *The Neurosciences Third Study Program*, F. O. Schmitt and F. G. Worden, Eds. (MIT Press, Cambridge Mass., 1974, Chap. 38; Jackson, in *Molecular Genetics of Biological Rhythms*, M. W. Young, Ed. (Dekker, New York, 1993), pp. 91–121). When populations of Drosophila are entrained to 12 hours of light followed by 12 hours of darkness (LD 12:12), adults emerge from pupae (enclose) rhythmically, with peak eclosion recurring every morning. The eclosion rhythm persists when the entraining cues are removed and behavior is monitored in constant darkness, thus indicting the existence of an endogenous clock. Adult locomotor activity is also controlled by an endogenous clock and recurs rhythmically with a 24-hour period.

Mutations in the Drosophila period (per) gene disrupt circadian rhythms of pupal eclosion and adult locomotor behavior (Konopka and Benzer *Proc. Natl. Acad. Sci. U.S.A.* 68:2112 (1971)). Although per has been cloned and sequenced and its pattern of expression has been analyzed (Baylies et al in *Molecular Genetics of Biological Rhythms*, M. W. Young, Ed. (Dekker, New York, 1993), pp. 123–153; Rosbash and Hall *Neuron* 3:387 (1989)), the biochemical function of the PER protein is unknown. PER shares some homology with a family of transcription factors (Crews et al *Cell* 52:143 (1988); Nambu et al *Cell* 67:1157 (1991); Reisz-Porszasz et al *Science* 256:1193 (1992); Hoffman et al *Cell* 252:954 (1991); Burbach et al *Proc. Natl. Acad. Sci. U.S.A.* 89:8185 (1992)) that possess a common sequence motif called the PAS domain. The PAS domain consists of two repeats of approximately 50 amino acids within a homology region of 258 to 308 amino acids. Sequence similarity between PER and protein regulating aspects of Drosophila development, SIM (encoded by the gene single-minded), was first recognized by Crews et al (Jackson et al *J. Neurogenet* 1:3 (1983); Dushay et al *J. Biol. Rhythms* 4:1 (1989); Dushay et al *Genetics* 125:557 (1990); Konopka et al *J. Neurogenet* 7:103 (1991)). Subsequent studies have shown that this homology region is also found in ARNT (arylhydrocarbon receptor nuclear translocator), a component of the multisubunit mammalian dioxin receptor (Reyes et al *Science* 256:1193 (1992); Hoffman et al *Neuron* 252:954 (1991)), and in AHR, the ligand-binding subunit of the dioxin receptor (Burbach et al *Proc. Natl. Acad. Sci. U.S.A* 89:8185 (1992)). The region of homology is now referred to as the PAS domain, after the first three proteins in which it was identified: PER, ARNT, and SIM (Huang et al *Nature* 364:259 (1993)).

Immunocytochemical experiments demonstrated that PER is a nuclear protein in a variety of Drosophila tissues (Konopka and Benzer (1971); Baylies et al (1993)). In cells of the adult fly visual and nervous systems, the amount of PER protein fluctuates with a circadian rhythm (Edery et al *Proc. Natl. Acad. Sci. U.S.A* 91:2260 (1994)), the protein is phosphorylated with a circadian rhythm (Edery et al (1994)), and PER is observed in nuclei at night but not late in the day (Siwicki et al *Neuron* 1:141 (1988); Saez and Young *Mol. Cell. Biol.* 8:5378 (1988); Zerr et al *J. Neurosci* 10:2749 (1990)). The expression of per RNA is also cyclic. However, peak mRNA amounts are present late in the day, and the smallest amounts are present late at night (Konopka and Benzer (1971)). Three mutant alleles—$per^O$, $per^S$, and $per^L$, —cause arrhythmic behavior or shorten or lengthen periods, respectively (Konopka and Benzer (1971)). These mutations also produce corresponding changes in the rhythms of per RNA and protein amounts (Edery et al (1994); Hardin et al *Nature* 343:536 (1990); *Proc. Natl. Acad. Sci. U.S.A.* 89:11711 (1992); Sehgal et al *Science* 263:1603 (1994)) and PER immunoreactivity in nuclei (Sewicki et al *Neuron* 1:141 (1988); Saez and Young *Mol. Cell. Biol.* 8:5378 (1988); Zerr et al *J. Neurosci.* 10:2749 (1990)). This suggests a possible role for molecular oscillations of per in the establishment of behavioral rhythms (Hardin et al (1992)). Several mutations that affect eclosion and locomotor activity have been isolated in behavioral screens (Jackson (1993); Konopka and Benzer (1971); Rosbash and Hall (1989); Baylies et al (1993) Jackson (1983); Dushay et al (1989); Dushay et al (1990); Konopka et al (1991)). The best characterized, and those with the strongest phenotypes, are mutations at the X chromosome-linked period (per) locus (Konopka and Benzer (1971); Rosbash and Hall (1989); Baylies et al (1993) Jackson (1983); Dushay et al (1989); Dushay et al (1990)). Missense mutations at per can lengthen or shorten the period of circadian rhythms, whereas null mutations abolish circadian rhythms altogether. The per gene is expressed in many cell types at various stages of development. In most cell types, the period protein (PER) is found in nuclei (James et al *EMBO J.* 5:2313 (1986); Liu et al *Genes Dev.* 2:228 (1988); Saez and Young *Mol. Cell. Biol.* 8, 5378 (1988); Liu et al *J. Neurosci.* 12:2735 (1992) Siwicki et al *Neuron* 1:141 (1988); Zerr et al *J. Neurosci.* 10:2749 (1990); Edery et al *Proc. Natl. Acad. Sci. U.S.A.* 91:2260 (1994)). A domain within PER is also found in the Drosophila single-minded protein (SIM) and in subunits of the mammalian aryl hydrocarbon receptor (Crews et al *Cell* 52:143 (1988); Hoffman et al Science 252:954 (1991); Burbach et al *Proc. Natl. Acad. Sci. U.S.A.* 89:8185 (1992); Reyes et al *Science* 256:1193 (1992)), and this domain (PAS, for PER, ARNT, and SIM) mediates dimerization of PER (Huang et al *Nature* 364:259 (1993)). The amounts of both PER protein and RNA oscillate with a circadian period, which is affected by the per mutations in the same manner as behavioral rhythms are affected (Siwicki et al (1988); Zerr et al (1990); Edery et al (1994); Hardin et al *Nature* 343:536 (1990); *Proc. Natl. Acad. Sci. U.S.A.* 89:11711 (1992)). Given the homologies to sim and the aryl hydrocarbon receptor (which are thought to regulate transcription), the effects of per on behavioral rhythms have been postulated to depend on circadian regulation of gene expression, including that of per itself (Hardin et al *Nature* 343:536 (1990); *Proc. Natl. Acad. Sci. U.S.A.* 89:11711 (1992)). However, neither direct proof of this postulate nor elucidation of per's actual biochemical function has been forthcoming.

SUMMARY OF THE INVENTION

Accordingly, a major object of the present invention is to provide a nuclear translocation protein which binds to a protein involved in circadian rhythms, including a protein, active fragments thereof, agonists thereof, mimics thereof, and combinations thereof, wherein the nuclear translocation protein has a specific binding activity to the protein involved in circadian rhythms and at least one of the following additional characteristics:

(i) cyclic transcription patterns related to the sleep-wake cycle, that are believed to inhibit the transcription of the nuclear translocation protein DNA once the nuclear translocation protein is present in the nucleus; or (ii) a stabilizing effect on the protein involved in circadian rhythms; or (iii) being light-sensitive and thereby capable of bestowing a light-sensitivity to the protein involved in circadian rhythms.

A further aspect of the present invention relates to the ability of the nuclear translocation protein to aid the process of circadian rhythm entrainment. More particularly, the nuclear translocation protein aids in entraining circadian rhythms to environmental cycles of light. This characteristic relates to the light-sensitivity of the nuclear translocation factor, as the light-sensitivity of the nuclear translocation protein is imparted to a protein required in circadian rhythms, due to that protein's dependence on the nuclear translocation protein for stability. In preferred embodiments, the nuclear translocation protein together with the protein required in circadian rhythms aid in the regulation of the transcription of DNA coding for one or both of these proteins. This aspect of the invention is exemplified for the PER and TIM proteins in Example 12, as appears herein.

In preferred embodiments the nuclear translocation factor will possess two of these additional characteristics. In more preferred embodiments, the nuclear translocation factor will have all of these characteristics.

An additional aspect of the present invention provides a novel use of the Period (PER) protein, wherein the PER protein aids in the nuclear translocation of the Timeless (TIM) protein and thereby plays a role in the regulation of timeless DNA transcription.

Another object is to provide an antibody to the aforesaid nuclear translocation protein.

Still another object of the invention is to provide an immortal cell line that produces the aforesaid antibody.

Yet another object is to provide a DNA sequence or degenerate variant thereof, which encodes a nuclear translocation protein, or a fragment thereof, including (A) the DNA sequences of SEQ ID NOS:1, 2 or 4;
(B) DNA sequences that hybridize to SEQ ID NOS:1, 2 or 4 under standard hybridization conditions; and
(C) DNA sequences that code on expression for amino acid sequences encoded by SEQ ID NOS:3 or 5.

Another object is to provide a probe capable of screening for the aforesaid nuclear translocation protein.

A further object is to provide a unicellular host transformed with a recombinant DNA molecule including a DNA sequence or degenerate variant thereof, which encodes a nuclear translocation protein, or a fragment thereof, from:

(A) the DNA sequences of SEQ ID NOS:1, 2 or 4;
(B) DNA sequences that hybridize to SEQ ID NOS:1, 2 or 4 under standard hybridization conditions; and
(C) DNA sequences that code on expression for amino acid sequences encoded by SEQ ID NOS:3 or 5,
wherein the DNA sequence is operatively linked to an expression control sequence.

Another object is to provide a method for detecting the presence or activity of the aforesaid nuclear translocation protein, including the steps of:

A. contacting a biological sample from an organism in which the presence or activity of the nuclear translocation factor is suspected with a binding partner of the protein under conditions that allow binding of the protein to the binding partner to occur; and B. detecting whether binding has occurred between the protein in the sample and the binding partner;
wherein the detection of binding indicates that presence or activity of the protein in the sample.

A further object is to provide a test kit for the demonstration of a nuclear translocation protein in a cellular sample, including:

A. a predetermined amount of a detectably labelled specific binding partner of a the nuclear translocation protein;

B. other reagents; and

C. directions for use of the kit.

Yet another object is to provide a method of preventing and/or treating disorders of a circadian rhythm, including administering to an animal a therapeutically effective amount of a material selected from the group consisting of a nuclear translocation protein, an agent capable of promoting the production and/or activity of the protein, an agent capable of mimicking the activity of the protein, an agent capable of inhibiting the production of the protein, and mixtures thereof, or a specific binding partner thereto, said protein having the characteristics of the aforementioned nuclear translocation protein.

Still another object is to provide a pharmaceutical composition for the treatment of disorders of a circadian rhythm including:

A. a therapeutically effective amount of a material selected from the group consisting of a nuclear translocation protein, an agent capable of promoting the production and/or activity of the protein, an agent capable of mimicking the activity of the protein, an agent capable of inhibiting the production of the protein, and mixtures thereof, or a specific binding partner thereto, the protein having the characteristics of the aforesaid nuclear translocation protein.

Another object is to provide an antisense nucleic acid against a nuclear translocation factor MRNA.

A further object is to provide a nuclear translocation factor-producing cell line transfected with the recombinant DNA molecule encoding a nuclear translocator protein.

With the foregoing and other objects, advantages and features of the invention that will become hereinafter apparent, the nature of the invention may be more clearly understood by reference to the following detailed description of the preferred embodiments of the invention and to the appended claims.

Figure 1A:
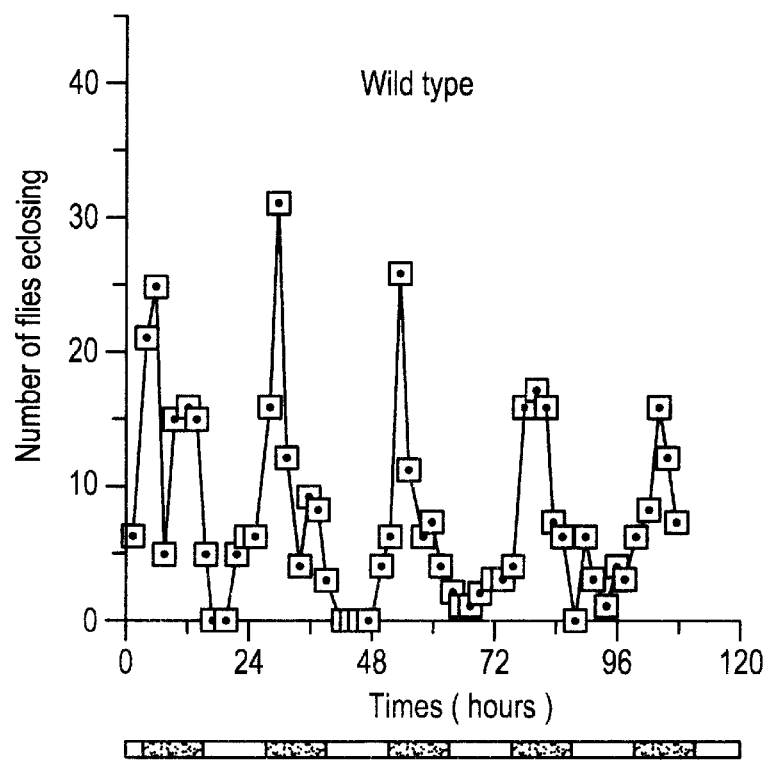
FIGS. 1A and 1B. Assessment of eclosion in tim flies. (A) Eclosion of wild-type flies in constant darkness (DD). (B) Eclosion of tim flies in DD. At the bottom of (B) are phases of LD cycles during entrainment (hatched boxes represent subjective day during collection). Flies were entrained by maintaining them in LD 12:12 at 25° C. for 4 days. Twenty hours before the first collection, lights were turned off. Newly emerged adults were collected and counted every 2 hours. A safelight that blocks wavelengths less than 600 nm (15-W bulb with a Kodak GBX-2 filter) was used to collect the eclosing adults.

Each collection consisted of shaking approximately 1,500 flies into a 15-mi conical polypropylene tube kept in dry ice. Total RNA was extracted from the heads, which were separated from the bodies by shaking frozen flies in sieves at temperatures below -20° C. A $^{32}$P-labeled riboprobe that protects 316 nucleotides (nt) of per MRNA (nt 123 to 438 of the per MRNA coding sequence) (Konopka and Benzer (1971); Rosbash and Hall (1989); Baylies et al (1993)) was transcribed from cloned per DNA. A tubulin riboprobe also was produced that protects 86 nt (nt 57 to 142 from the start of transcription of α 1 tubulin mRNA (Theurkauf et al *Proc. Natl. Acad. Sci. U.S. A.* 83:8477 (1986)). Ribonuclease (RNase) protection experiments were carried out as described (Zinn et al *Cell* 34:865 (1983)) with minor variations. Ten micrograms of head RNA was used for each time point, and digestions with RNase were for 30 minutes at 25° C. Hybridizations and RNase digestions were performed contemporaneously for wild-type, $per^O$, and tim RNA samples representing the first 4 days. For days 5 and 6 of the tim record, RNA hybridizations and digestions involved newly labeled riboprobes, so RNA from day 4 was again processed to allow direct comparison of per RNA amounts measured in the two sets of experiments. Digested samples were separated by electrophoresis on 5% polyacrylamide—8M urea gels. Dried gels were exposed to x-ray film and also analyzed with a phosphorimager (Molecular Dynamics) for quantitation. (A) RNase protection experiments showing amounts of per and tubulin RNA at different Zeitgeber times in wild-type (Canton S), $per^O$, and tim flies. The repeating series of numbers marking the lanes at the top of each autoradiograph indicates Zeitgeber time over four successive LD 12:12 cycles for wild-type and $per^O$ flies and six cycles for tim flies. (B) Quantitative analysis of per RNA amounts in Canton S, $per^O$, and tim flies. For the plots presented in (B), the autoradiographs shown in (A) were analyzed with a phosphorimager, and per and tubulin bands were quantitated. The plot shows per/tubulin ratio measured in wild-type flies. All other per/tubulin were normalized to per/tubulin amounts in the wild-type maximum. Data points on days 5 and 6 of the tim record were normalized relative to the highest per/tubulin ratio on those days. The phase of the LD 12:12 cycle is presented at the bottom of (b). Open boxes indicate lights on; closed boxes indicate lights off.

Figure 4A:
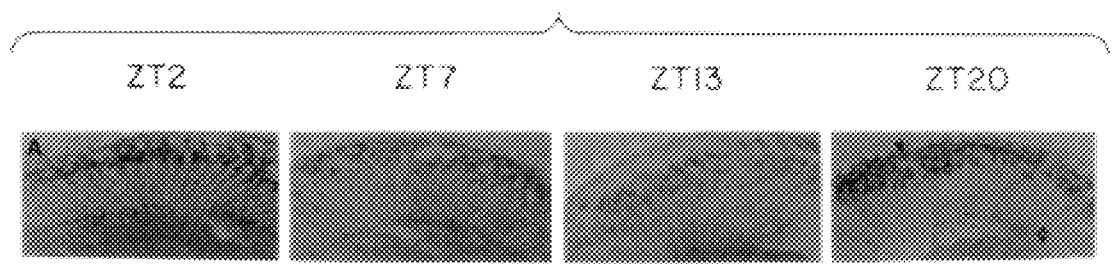
Figure 4B:
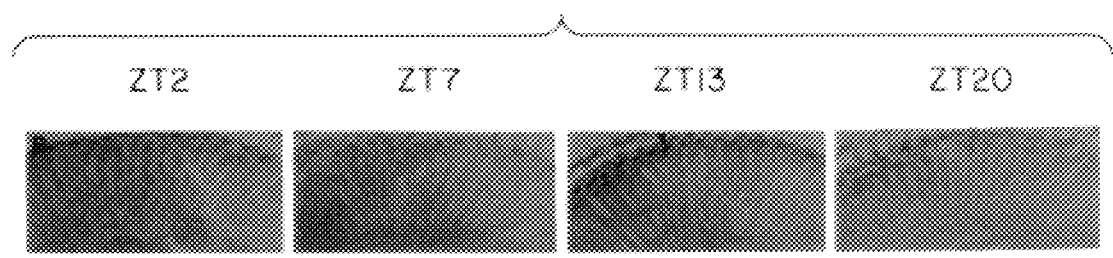
Figure 4C:
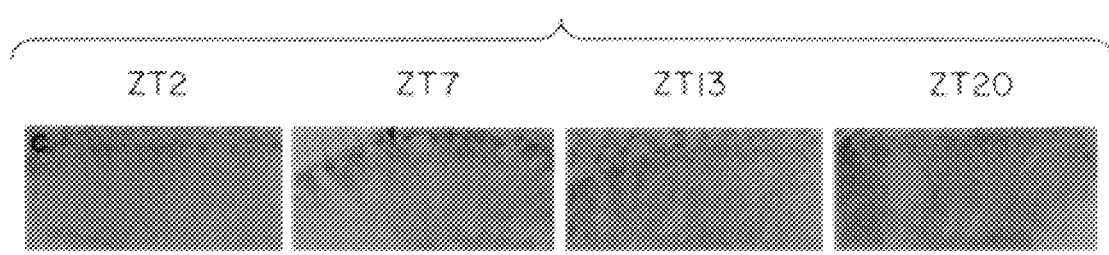

FIGS. 4A–4C. Expression of PER protein in (A) wild-type, (B) tim, and (C)$per^O$ mutant backgrounds at four time points. The nuclear layer is marked with open arrows. Structures underlying the lens frequently stain nonspecifically and do not reflect PER antibody staining in nuclei (black arrowheads). Flies were raised at 25° C. in a 12-hour light: 12-hour dark cycle (LD 12:12). Frozen sections (14 μm) from adult fly heads collected at the indicated times were incubated with PER antibody (1:30 dilution of immune serum with PER antibody 19-06 raised against full-length PER protein and preabsorbed against $per^O$ head lysate) for 16 hours at room temperature. Antibody staining was continued as described (Siwicki et al *Neuron* 1:141 (1988); Saez and Young *Mol. Cell. Biol.* 8:5378 (1988); Zerr et al *J. Neurosci.* 10:2749 (1990)) with the use of the Vectastain ABC kit (Vector labs).

FIGS. 5A–5G. Immunocytochemistry and protein immunoblot analysis of a PER-β-gal fusion protein (PER-SG) (Liu et al *Genes Dev.* 2:228 (1988); Liu et al *Neuron* 6:753 (1991); Liu et al *J. Neurosci.* 12:2735 (1992); Ewer et al *J. Neurosci.* 12:3321) in tim+ and tim recombinant lines. Shown is expression of PER-SG in head sections from tim+ (A through C) and tim mutant (D through F) recombinant lines. For (A) through (C), staining of nuclei was observed in photoreceptor cells (ret), lamina (lam), medulla (med), and some cells of the central brain. Open arrows indicate nuclear labeling. In (D) through (F), staining of photoreceptor cells and cells of the lamina, medulla, and central brain was also observed, but there is no indication of nuclear localization of the stain. Frozen sections were incubated with affinity-purified β-gal polyclonal antibody (Cappel/Organnon Technika, Durham, N.C.) (1:1000 dilution reabsorbed against adult fly acetone powder) and processed as described (FIG. 4). (G) Lines of tim+ and tim mutant flies containing PER-SG or a control line (Canton-S) lacking the transgene, were raised as described (FIG. 4). Flies (6 to 12 days old) were collected from ZT18 to ZT22. Extracts were prepared from the heads of flies as described (Zwiebel et al Proc. Natl. Acad. Sci. U.S.A. 88:3882 (1991)). Extract containing 1×(10 μg by Bradford assay), or the indicated fraction of total protein, was electrophoresed in each lane of an SDS-polyacrylamide gel (Laemmli et al Nature 227:680 (1970)) and analyzed for β-gal antigen levels as described by Saez and Young (Siwicki et al (1988); Saez and Young (1988); Zerr et al J. Neurosci. 10, 2749 (1990)). The primary antibody was a mouse β-gal monoclonal antibody, and the secondary antibody was goat antibody to mouse immunoglobulin G (heavy and light chains) alkaline phosphatase conjugate (both from Promega). Extracts from tim, PER-SG flies were loaded in the first four lanes; tim+, PER-SG extract in the fifth lane; and extract from a line that does not contain the PER-SG transgene (Canton-S) in the sixth lane. Molecular size markers (Amersham) are indicated to the left of the gel.

FIGS. 6A–6E. Localization of PER-β-gal and β-gal marker proteins in wild-type (left column) and tim mutant (right column) adult head sections. (A) PER1-95β-gal. (B) PER1-636β-gal (identical in amino acid composition to PER-SG, but constructed as described below). (C) PER1-636ΔNLS[66–79]β-gal. (D) Enhancer trap line S45 (expresses β-gal modified by the addition of a nuclear localization signal in the eye and a few cells in the brain). (E) Eye protein kinase C-β-gal (β-gal modified by the addition of the SV40 nuclear localization signal under the control of the eye-specific protein kinase C promoter) (Smith et al Science 254:1478 (1991)). Staining with antibodies to β-gal was as described in legend to FIG. 5. PER-β-gal fusion constructs were made by inserting an Xho I linker at nucleotide 3183)PER1-95β-gal; Acc I site) or at nucleotide 4936 (PER1-636β-gal and PER1-636ΔNLS[66–79]β-gal; Sac I site) (Baylies et al (1993)). PER1-636ΔNLS[66–79] β-gal is identical to PER1-636β-gal except that a fragment encoding amino acids 65 to 95 has been deleted in the former (Baylies et al (1993); Zwiebel et al Proc. Natl. Acad. Sci. U.S.A. 88:3882 (1991)). The Sph I-Xba I per promoter fragment was added and the per fragment excised with Xho I. All constructs were cloned into pCaSpeR-β-gal (Thummel et al Gene 74:445 (1988)), altered to create three different frames with Xho I linkers (L. B. Vosshall, thesis, Rockefeller University (1993)).

Figure 7:
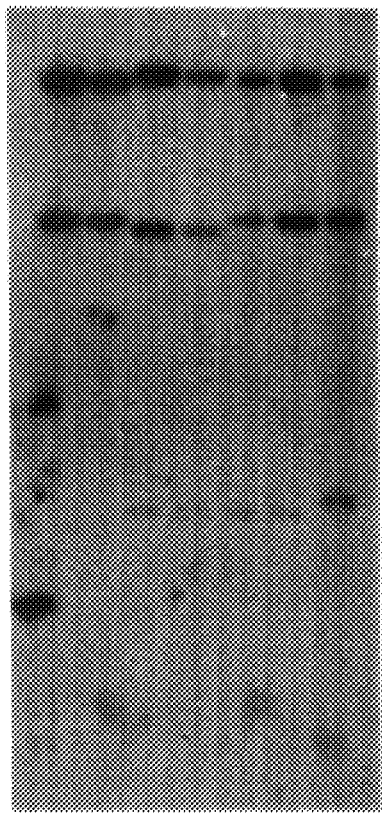

FIG. 7. Southern blot analysis of DNA from tim$^{02}$ and parental flies detecting a RFLP unique to tim$^{02}$ flies.

Figure 8:
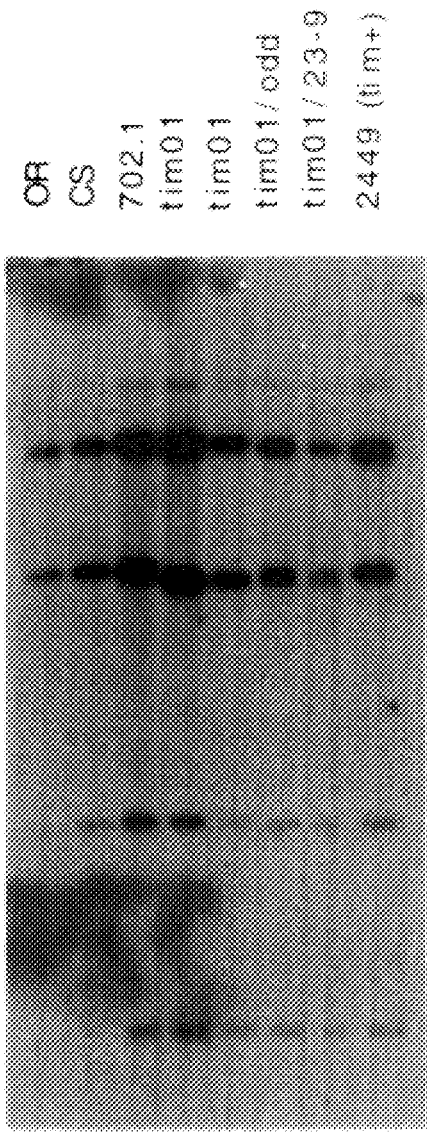

FIG. 8. Southern blot analysis of DNA from tim$^{01}$ and parental flies detecting a RFLP unique to tim$^{01}$ flies.

Figure 9:
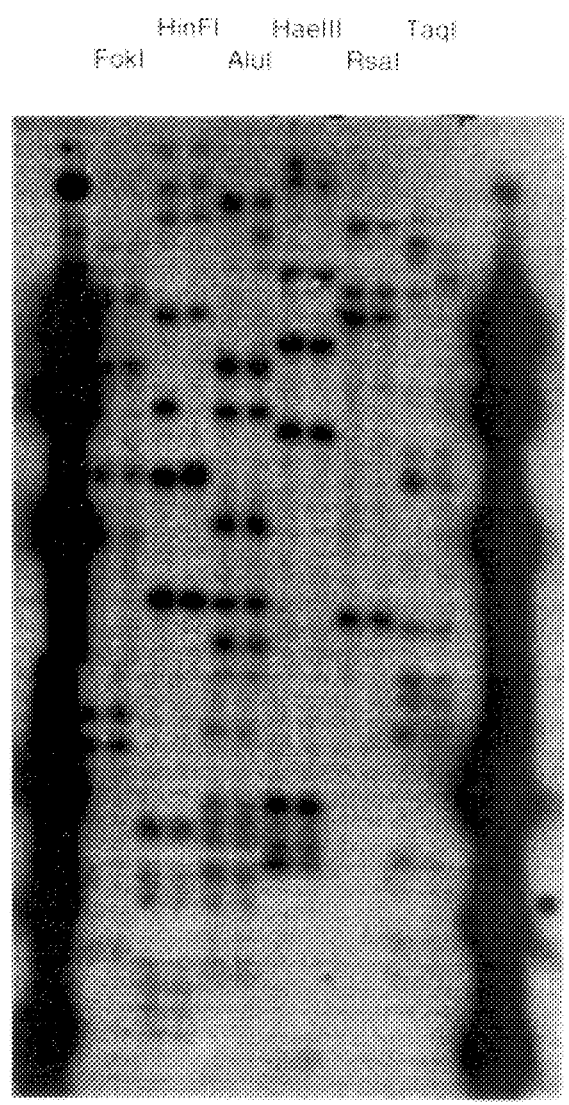

FIG. 9. Southern blot of mutant and wild-type DNAs cut with enzymes recognizing 4 and 5 bp sites.

Figure 10:
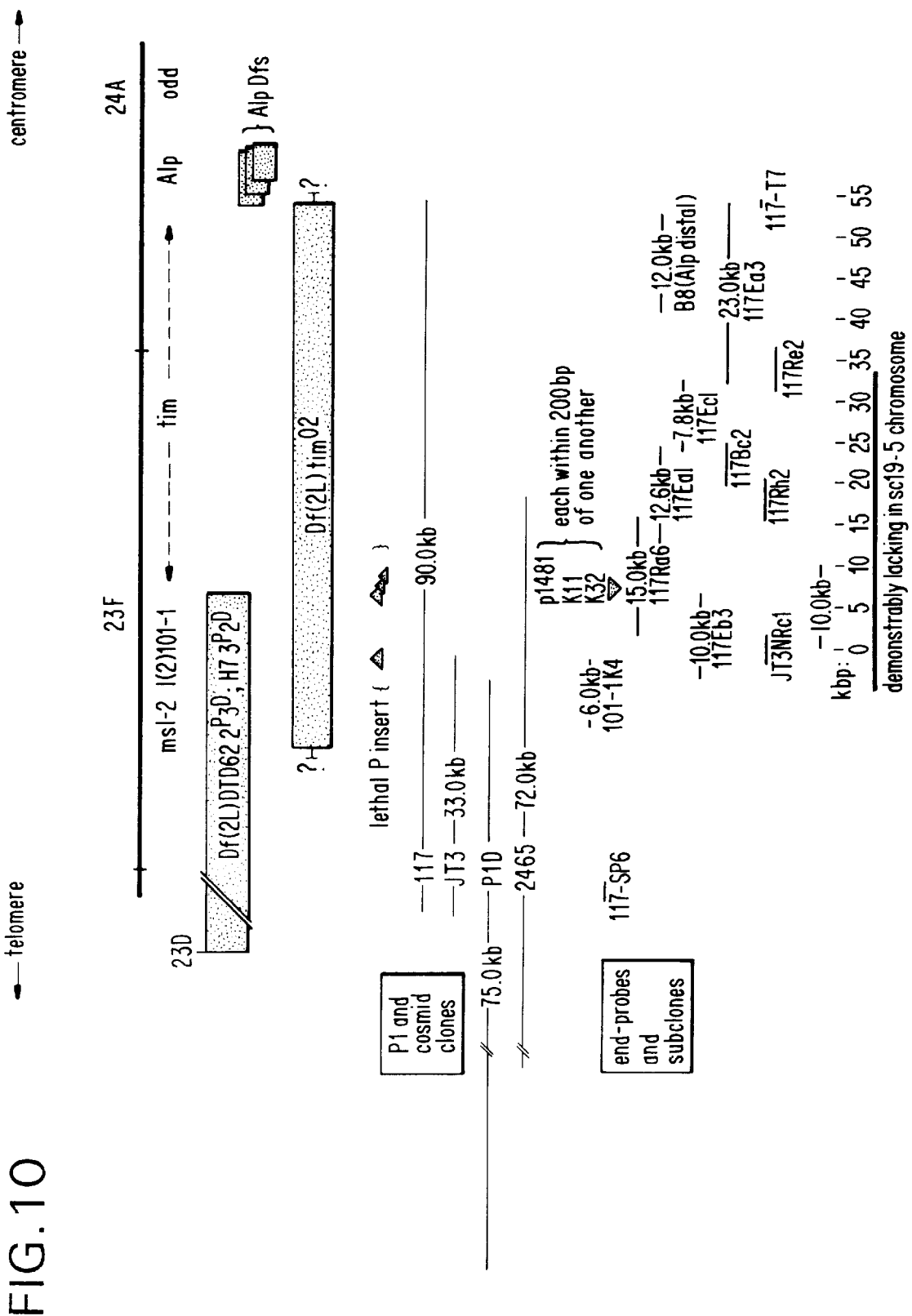

FIG. 10. Map of the tim region.

FIG. 11. Nucleotide sequence and conceptual translation of tim. The nucleotides deleted in tim$^{01}$ (2387 to 2450) are boxed, and the deduced amino acid sequence created by the new reading frame is indicated below the normal amino acid sequence created by the new reading frame is indicated below the normal amino acid sequence. The region in bold letters corresponds to the retained intron. When the intron is spliced out, amino acid 1105 is converted from R to L, and the reading frame continues to amino acid 1389. The acidic domain and potential NLS are indicated as white text on black. The polyadenylation signal is underlined.

Figures 12A, 12B, 12C:
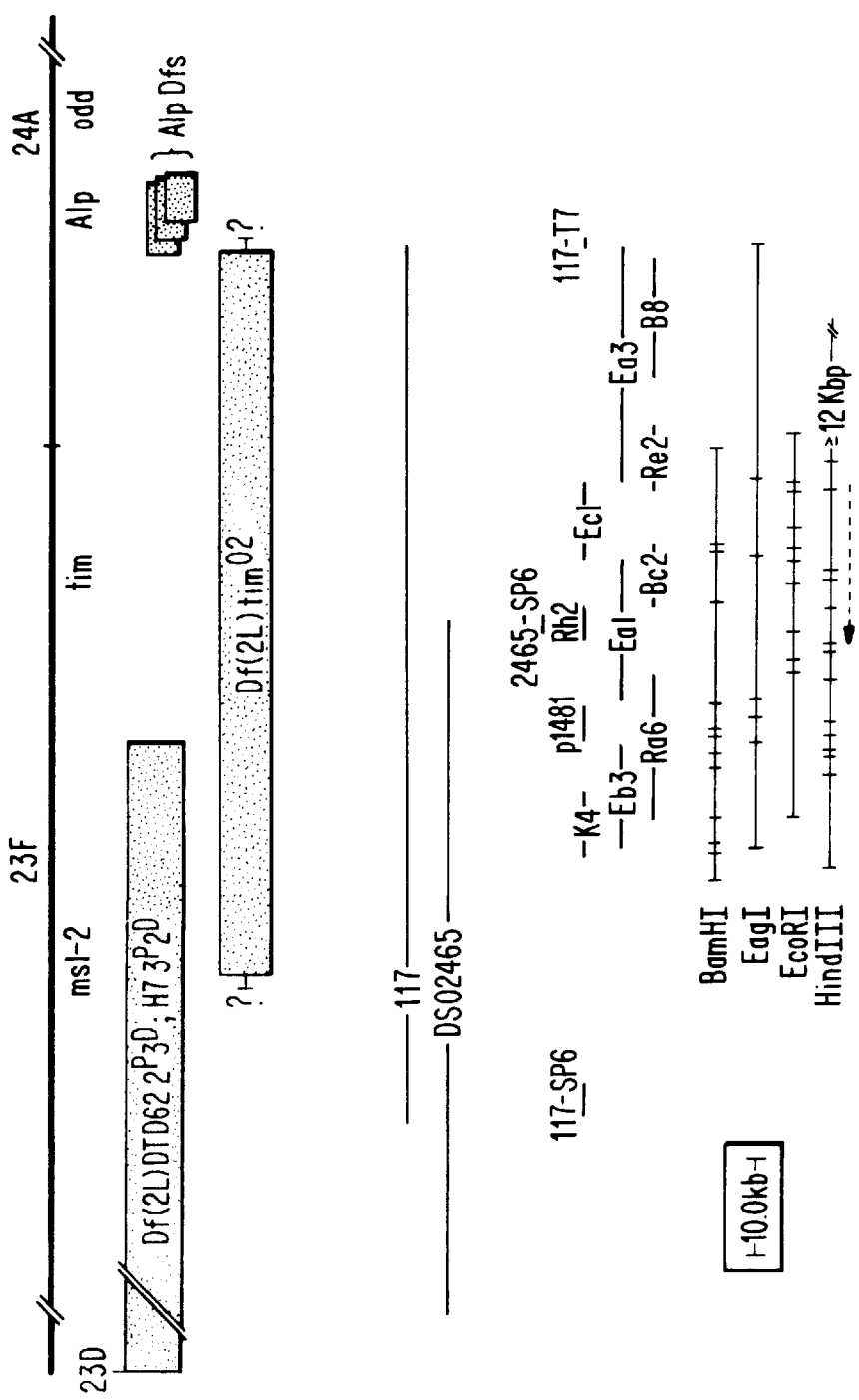

FIGS. 12A–12C. Schematic of tim locus on chromosome 2. The corresponding regions in A–C are in vertical register. (A) Mapping of tim by complementation tests with chromosome deficiencies. The deficiencies are depicted as solid bars representing the genetic material missing from the chromosome. Although Df(2L)DTD62 $2^P$ $3^D$; H7 $3^P$ $2^D$ is a synthetic deletion composed of two non-overlapping translocations of chromosome 2 to 13 (Sekelsky et al Genetics 139:1347 (1995)), for simplicity it is shown as a continuous deletion of chromosome 2. The proximal breakpoint of Df(2L)DTD62 $2^P$ $3^D$; H7 $3^P$ $2^D$ is located within clone Ra6 (C). The distal breakpoint of Df(2L)tim$^{02}$ lies to the left of msl-2, but has not been mapped further. The proximal breakpoint of Df(2L)tim$^{02}$ maps proximal to clone Ea3, and distal to a vital gene uncovered by the Ap deficiencies. (B) Overlapping P1 clones 117 (Shubo et al EMBO J. 14:2884 (1995)), and DS02465 (J. Lucchesi, W. Gelbart, Berkeley Drosophila Genome Project) used to generate a contig covering tim. (C) DNA clones and PCR products from the tim contig are shown in bold lines, and the restriction maps for Bam HI, Eag I, Eco RI, and Hind III corresponding to this region are shown. Clones K4 and p1481 were isolated by plasmid rescue from the P stocks 101-1 and P1481, respectively (J. Lucchesi, W. Gelbart, Berkeley Drosophila Genome Project). P1481 and two other P element insertions located within 200 bp (145-7, 145-12) were all found to be unlinked to the lethal phenotype upon which they were originally isolated (Myers, unpublished data). Clone B8 is from a walk covering the Alp gene (Cohen, personal communication).

Figures 13A, 13B:
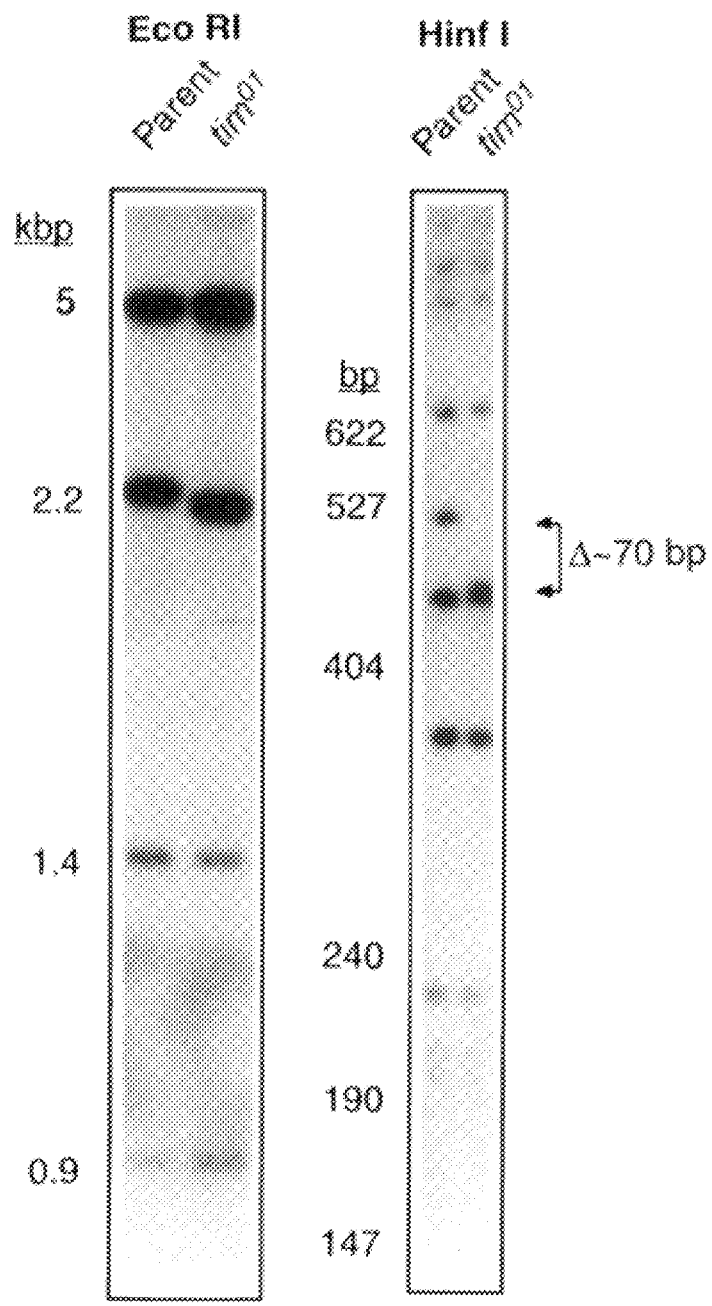

FIGS. 13A and 13B. Restriction Fragment Length Polymorphisms (RFLPs) detected in tim$^{01}$. Southern blots were prepared containing DNA from tim$^{02}$ and the wild type parental flies, after digestion with Eco RI (A) or Hinf I (B), and probed with the genomic DNA clone Ec1 (FIG. 12C). The gel in (A) was standard 1% agarose, whereas the gel in (B) was composed of 2% MetaPhor Agarose (FMC BioProducts, Rockland, Me.).

Figure 14A:
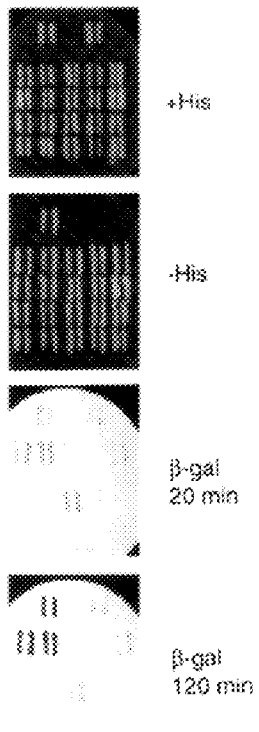
Figure 14B:
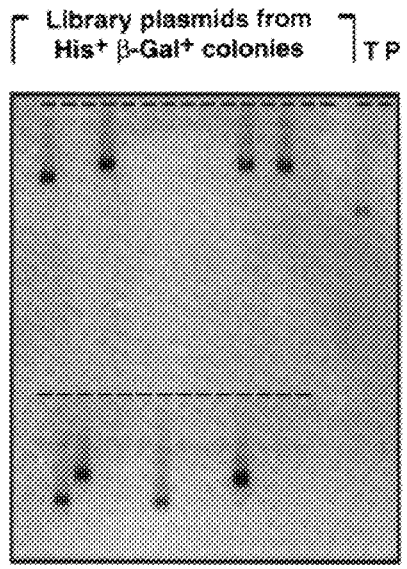
Figure 14C:
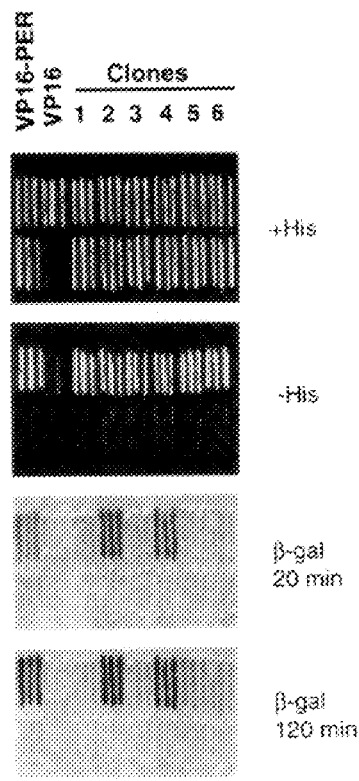

FIGS. 14A–14C. Two-hybrid screen for PER-interacting proteins. (A) Example of screening for His 3 and Lac Z reporter gene activation. Each panel shows duplicate yeast patches from 20 of the colonies that formed in the absence of histidine on the initial screening plates (4×5 grid). Positive control PER homodimerization transformants are on the upper left (LexA-PER+VP16-PER) and negative control transformants are on the upper right (Lex-A-PER+VP16). Top two panels: +His, control plate containing histidine (not selective for His 3 reporter gene activation) showing viability of the patches. –His, plate lacking histidine (re-test for the ability of transformants to grow in the absence of histidine). Bottom two panels, β-galactosidase assay performed on a filter lifted directly from the control plate in top panel; blue color indicates cumulative β-galactosidase activity after 20 min. or 120 min., as indicated. Altogether, 30 colonies grew in the absence of histidine (His+phenotype) from a screen of 2×10$^7$ library transformants, 67 of the His+colonies showed β-galactosidase activity, and, of 59 library plasmids purified from His+, β-gal+colonies, 48 produced PER-dependent interaction signals. Pink tinge of some patches in bottom panels is due to the Ade 2 mutation in the L40 strain. (B) Representative Southern blot of library plasmids isolated from His+, β-gal+yeast colonies probed with a 4.5-kb timeless cDNA (Myers et al *Science* Nov. 3, 1995). Short horizontal lines mark the positions corresponding to sample wells. T. positive control 1.5-kb insert from an independent, overlapping timeless cDNA clone. P, negative control 1.4-kb insert from per cDNA. Approximately 100–200 ng of each plasmid was digested to completion with Not I to release the insert, and agarose gel electrophoresis and Southern blotting were performed using standard methods. Blot was washed at high stringency (0.1× SSC, 0.1% SDS, 65° C.). Altogether, 16 of 48 clones producing PER-dependent interaction signals hybridized strongly to the probe. (C) PER-dependent interaction signals from the six independent two-hybrid clones hybridizing to timeless cDNA. Purified library plasmids were reintroduced into yeast to tests for His 3 and Lac Z reporter gene activation in a strain expressing the original LexA-PER bait (re-test) and a strain expressing an irrelevant bait (specificity test). Each panel shows triplicate yeast patches of LexA-PER strain (upper row) or LexA-Lamin strain (lower row) transformed with the positive control plasmid VP16-PER, the negative control plasmid VP16, or one of the six independent positive two-hybrid library plasmids (clones 1–6) that hybridized to timeless cDNA. Each triplicate represents three independent transformants. Panels arranged as in (A).

FIG. 15. Sequence alignments of clones encoding PER-interacting protein with timeless cDNA. Bar at top represents the 1389-codon open reading frame of full-length timeless cDNA (Myers et al *Science Nov.* 3, 1995). Bars below show alignments of each of the six clones (numbered 1–6 as in FIG. 14C) to the open reading frame; each bar begins and ends, respectively, with the number of the first and last complete codon within the sequence. Although clones 4, 5 and 6 all end with codon 906, they do not all end at the same nucleotide. In parentheses next to the designation of each clone is the number of times that clone was isolated in the two-hybrid screen.

FIGS. 16A–16D (A) Restricted region of PER sufficient for TIM-PER interaction signals. Two-hybrid assays in which the polarity of the elements has been reversed. Each panel shows triplicate patches of yeast expressing LexA-TIM 1 (upper row) or LelxA-TIM 2 (lower row) transformed with the negative control plasmid VP16, the positive control plasmid VP16-PER$_{233-685}$ or the indicated VP16-PER plasmid. Each triplicate represents three independent transformants. TIM1 and TIM2 bait hybrids correspond to the clones designated 1 and 2, respectively, in FIGS. 14C and 15. Top panel (+His), control plate containing histidine (not selective for His 3 reporter gene activation) showing viability of the patches. Middle panel (−His), plate lacking histidine (tests for the ability of transformants to grow in the absence of histidine). Bottom panel (βgal), β-galactosidase assay performed on a filter lifted directly from the control plate in top panel; blue color indicates cumulative β-galactosidase activity after 120 min. (B) Association of TIM and PER polypeptides in vitro. Left, Coomassie-stained SDS-PAGE gel of GST and GST-PER fusion proteins expressed in bacteria. Relative intensities of the major bands reflect the amount of GST fusion protein used in the in vitro TIM-PER binding assays; considerably more GST and GST-PER$_{530-640}$ were present than the other two GST-PER fusion proteins. Molecular weight markers on the right of each panel are in kilodaltons. Middle, differential binding of TIM fragment to different GST-PER fusion proteins. Autoradiograph showing SDS-PAGE analysis of in vitro-translated $^{35}$S-labelled TIM$_{1-1003}$ bound to the indicated GST-PER-agarose beads. First lane shows in vitro translation product prior to binding reaction. Right, differential binding of different TIM fragments to GST-PER. Autoradiograph showing SDS-PAGE analysis of indicated in vitro-translated $^{35}$S-labelled TIM fragments bound to GST-PER$_{1-640}$-agarose beads. First three lanes show indicated in vitro translation products prior to binding reaction.

Figure 17A:
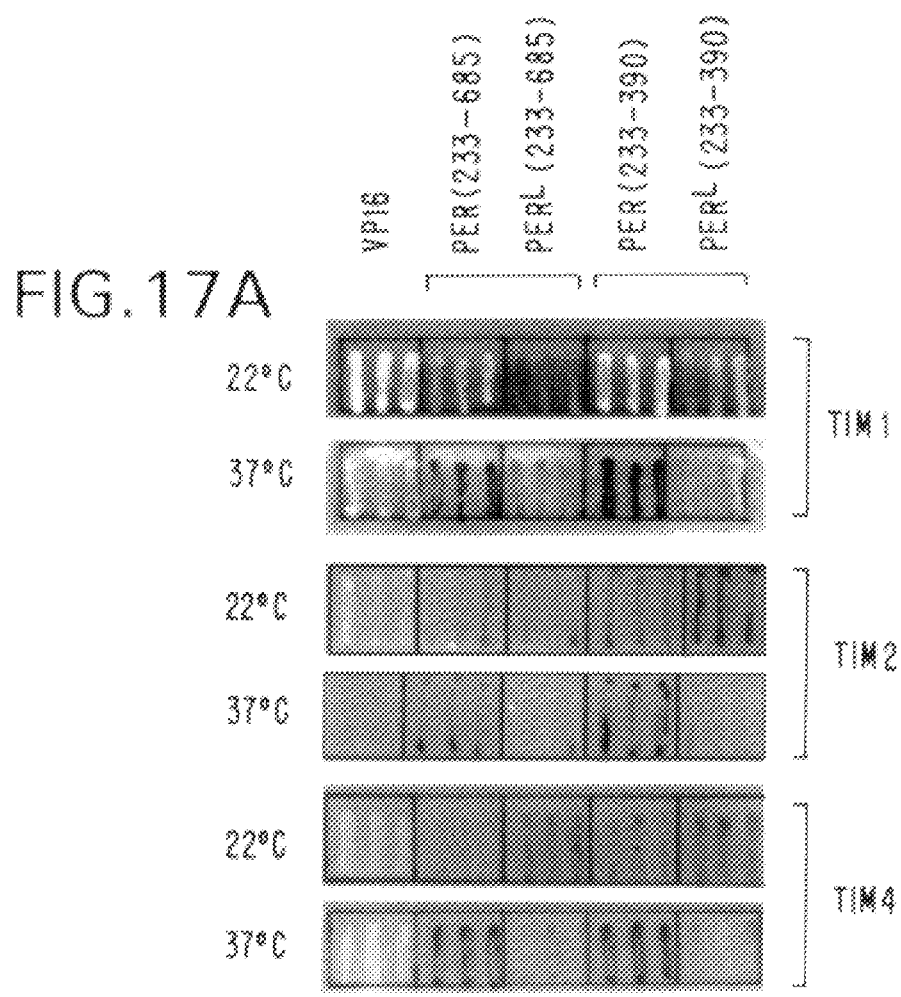
Figure 17B:
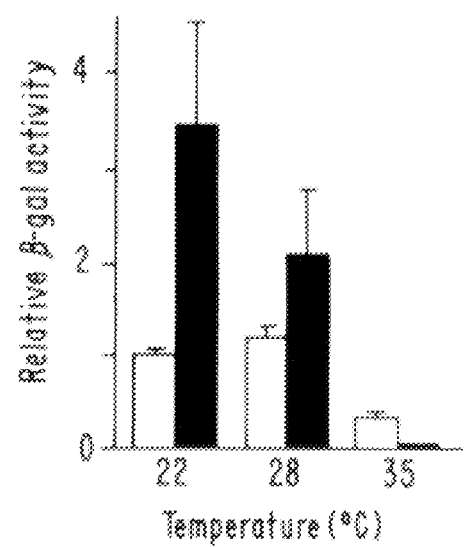

FIGS. 17A and 17B. Abnormal temperature-sensitivity of the interaction between TIM and PER$^L$. (A) Triplicate patches of yeast were grown at 22° C. or 37° C. on plates containing the β-galactosidase substrate X-gal. Yeast expressing the bait hybrids LexA-TIM1, LexA-TIM2, or LexA-TIM4 were transformed with the negative control plasmid VP16 or the indicated VP16-PER or VP16-PER$^L$ plasmid. Each triplicate represents three independent transformants. Blue precipitate indicates cumulative β-galactosidase activity. LexA-TIM1, LexA-TIM2 and LexA-IM4 baits correspond to the clones designated 1, 2 and 4, respectively, in FIGS. 14C and 15. To provide the clearest comparison of the TIM interaction signal produced by the corresponding PER and PER$^L$ proteins at each temperature, plates were incubated at the indicated temperatures until a clear signal developed in at least some of the patches, in general a shorter time for 37° C. plates than 22° C. plates (due to the greater activity of β-galactosidase activity at the higher temperature) and a shorter time for TIM2 and TIM4 plates than for TIM1 plates (due to the stronger PER interaction signals produced by TIM2 and TIM4. Yeast transformants were patched to plates containing TULL medium (synthetic medium lacking tryptophan and leucine) supplemented with X-Gal (Sigma) to a final concentration of 100 μg.ml (added to TULL medium as a 1000X stock in N,N-dimethyl formamide. Transformants shown in FIG. 17A were grown as follows: TIM1: 22° C. for 6 days, 37° C. for 5 days; TIM2 and TIM4: 22° C. for 1.5 days, 37° C. for 1 day. In this experiment, direct comparisons of signal strength are valid only for patches on a given plate, not across plates. (B) β-galactosidase activity from liquid cultures of yeast expressing LexA-TIM1 and VP16-PER$_{233-685}$ (open bars) or VP16-PER$_{233-685}$ (solid bars) and grown at the indicated temperatures. Shown are the mean and standard error determined for at least 11 cultures derived from at least 6 independent transformants. For LexA-TIM1/VP16-PER$_{233-685}$ at 35° C., the standard error is too small to be shown at this scale. Consistent with the plate assays shown in (A), the TIM1 interaction signal for PER$^L$ is stronger than that of wild-type PER at 35° C. (P<0.001). Specific β-galactosidase activity was calculated as $A_{420}$/hr/mg protein. Within each independent experiment, specific β-galactosidase activities were normalized to that of the TIM1, PER (wild-type) control culture grown at 22° C. For each experiment, single TIM,PER (wild-type) and TIM1, PER$^L$ transformants were processed in parallel. Each transformant yeast colony was resuspended in 6 ml of TULL medium. The suspension was divided into three 2 ml cultures, which were then grown at 22°, 28° or 35° C., respectively, for 24 hours. Cultures were diluted 100-fold with fresh TULL medium, and 2 ml of the diluted culture was grown (at the same temperature as the initial incubation) to a final $A_{600}$ of 0.8–1.2. Extraction of β-galactosidase from yeast and assays of β-galactosidase activity were performed as described [F. M. Ausubel et al Current Protocols in Molecular Biology, John Wiley and Sons, New York, 1988)]. Specific β-galactoside activities were normalized to that of the TIM1,PER (wild-type) control culture grown at 22° C.

Figure 18A:
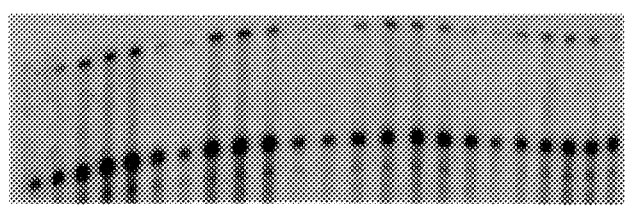
Figure 18B:
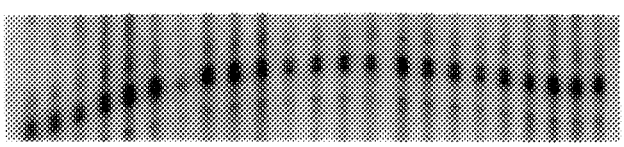
Figure 18C:
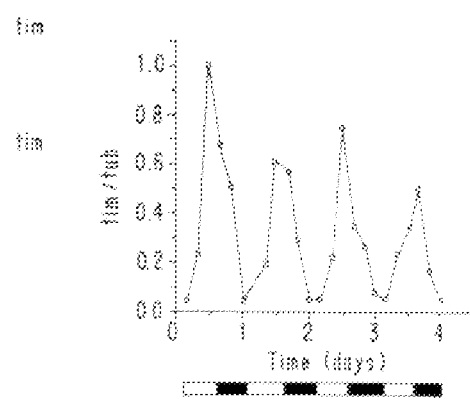
Figure 19A:
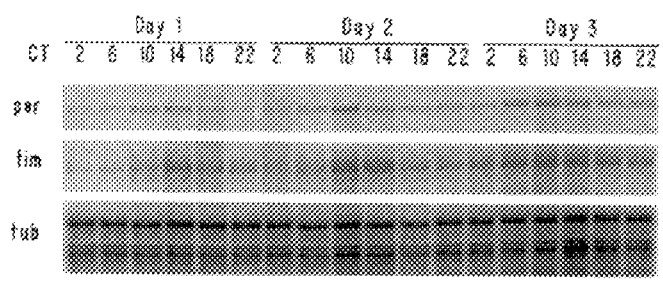
Figure 19C:
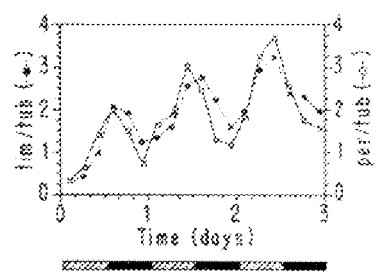
Figure 19B:
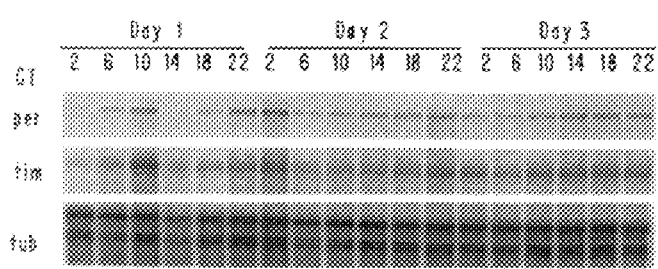
Figure 19D:
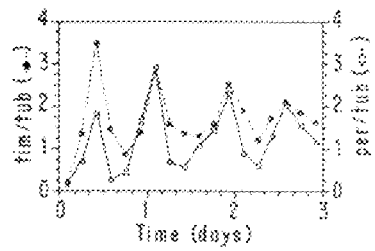

FIGS. 18A–18C. Temporal expression of tim RNA in wild type and tim mutant flies. (A, top) Adult flies maintained in a 12-hour light: 12 hour dark cycle (LD 12:12) for a minimum of three cycles were subjected to RNase protection assays as previously described (Sehgal (1994) *Science* 263:1603). Total head RNA (10 μg) from these flies was hybridized to a tim riboprobe that corresponds to nucleotide 1971 to nucleotide 2367 of the tim cDNA sequence (Myers et al, accompanying report) and also includes some plasmid vector sequences, and to a tubulin probe (tub) that is complementary to nucleotides 1 to 142 of the tubulin sequence (Therkauf et al (1986) *Proc. Natl. Acad. Sci. USA* 83:8477). Following RNase digestion, the fragments were run on a 5 % denaturing polyacrylamide gel. Pattern of tim RNA expression was examined at four-hour intervals over a four-day period. Numbers at the top of lanes correspond to zeitgeber time (ZT), which indicates the light:dark cycle that was used to entrain the flies (ZT0=lights on, ZT10=lights off). The ZT2 time point is missing on the second day. The tim riboprobe protects two fragments, possibly due to the presence of a specific breakdown product of the probe, or due to a nucleotide polymorphism(s) distinguishing the probe and the protected RNA as these were derived from different Drosophila strains. Fragments protected by the tub riboprobes are also indicated. This image was generated by scanning the original autoradiograph using the UMax scanning program included in the Adobe Photoshop software (A, bottom) tim and tub bands were quantitated using a phosphorimager and the tim/tub ratio which is defined here as 1. Data shown here (and in panel C) are for the top tim band, but a similar plot was obtained when the bottom band was quantitated (not shown). ZT14 on day 4 was quantitated separately because the gel fractured adjacent to this lane prior to quantitation. Its value was normalized to the rest of the data by requantitating other time points from the gel at the same time. (B, Left) Cycling of tim and per RNA under freerunning conditions in wild type and $per^s$ flies. Flies were entrained to three light:dark cycles and then transferred to constant darkness. Collections were made at four-hour intervals, starting 14 hours after "lights off." RNase protections (19. "Total RNA was isolated from ~80 μl fly heads using 1 ml of RNAzol B solution (TelTest Inc., Friendswood, Tex.). RNase protections were performed according to the manufacturer's specifications (RPA II kit, Ambion Inc., Austin, Tex.). RNA digestions were incubated for one hour at 37° C., and half the final sample volume was loaded, and electrophoresed on a 5% acrylamide/8M urea gel.) were performed on 15 μg of total head RNA, using probes for tim, per, and tubulin. The tim probe protects nucleotides 4963 to 5192 of the tim cDNA sequence (Myers et al *Science* Nov. 3, 1995), the per probe is described is described in Sehgal et al 1994 *Science* 263:1603, and the tubulin probe above. Image shows three day time course of tim, and per RNA in wild type and $per^s$ flies in constant darkness. Numbers atop each lane indicate circadian time of sample collection on three consecutive days. In freerunning conditions, circadian time is used in lieu of zeitgeber time, to reflect the entrainment regimen. Gels were exposed in a phosphorimager cassette (Molecular Dynamics), and the images were transferred to Adobe Photoshop software for printout. (B, right) tim/tubulin, and per/tubulin ratios were normalized such that the value of 1 corresponds to the mean relative per or tim RNA level produced in wild type flies reared in LD 12:12. These values were determined by collecting time points at 12 consecutive 2-hour intervals in a single LD 12:12 cycle. per and tim RNA levels for each time point were assessed in three separate experiments. The mean value of all time points was then set to 1. Wild type ZT2 and ZT12 samples from the above experiments were also subjected to RNase protection and run on each gel for comparison to the experimental digest (A. Rothenfluh-Hilfiker et al, unpublished data). (C, Top) Effect of the $tim^{01}$ mutation on the cycling of tim RNA in the presence of LD 12:12. RNase protection assays were carried out on 10 μg of total head RNA, with the tim and tubulin riboprobes described for panel (A), above. RNA determinations were made at four-hour intervals over a four-day period. ZT18 on day 1 and ZT14 on day 2 were not quantitated as these lanes were considerably underloaded relative to the other lanes. (C, bottom) Quantitations were performed as described for Panel A, above.

FIG. 19. Model depicting how interdependence of per and tim might generate circadian cycles in feedback regulation. PER protein accumulation and nuclear localization are suppressed in $tim^{01}$ mutants (Vosshall et al (1994) *Science* 263:1606; Price et al (1995) *EMBO J*. 14:4044). Thus, it is predicted that PER will accumulate in conjunction with per mRNA only if TIM proteins were amassed prior to per transcription. As per and tim RNAs accumulate with the same phase, delays in PER accumulation and nuclear localization are expected, probably reflecting times of PER/TIM heterodimer formation. If high levels of PER protein suppress per expression (Zeng et al (1994) *EMBO J* 13:3590), cycles in this regulation will result from separate temporal phases of per RNA accumulation and PER protein accumulation that are promoted by the pattern of tim expression. In the absence of a mechanism supporting such delays, feedback control should lead to constitutive gene and protein synthesis, albeit at intermediate levels.

FIGS. 20A–20D. Western blot analysis of TIM protein in wild type, $tim^0$, and $per^0$ flies. Equivalent amounts of total protein from fly heads isolated at various times were separated by SDS-PAGE, blotted to nitrocellulose, and probed with anti-TIM antibodies. Fly head extracts were prepared as described (Edery et al (1994); Zeng et al (1994)). TIM-specific antibodies were raised in rats against affinity purified glutathione-S-transferase fusion proteins expressing either residues 222–577 (Ab 307) or 1133–1389 (Ab 310) of TIM. The western blots shown in this report used Ab 307. The antibodies were prepared by HRP, Inc., Denver, Pa. All westerns were visualized by chemiluminescence (ECL, Amersham, Arlington Heights, Ill.). (A) Levels of TIM protein at 4 hour intervals in a LD cycle (12 hours light:12 hours dark). TIM, filled arrowhead; non-specific band, open arrowhead. The two lanes marked (D) (dark) and (L) (light) are extracts from $tim^0$ fly heads isolated from flies at ZT19 and ZT7, respectively. (B) Levels of TIM protein in $per^0$ fly heads under dark and light conditions. The $per^0$ dark sample was prepared from dark-reared flies, and the light sample from ZT7 of a LD cycle. (C) Levels of TIM protein in extracts from control and light treated $per^0$ flies previously reared in constant darkness. $per^0$ flies were maintained in constant darkness for 4 days. At time "0", a set of flies was pulsed with light (~8000 lux) for a period of 1 hour, then returned to constant darkness. Control flies and light pulsed flies were harvested 0, 1, 2, 3, 5, 7, and 9 hours from the start of pulse. One group of flies were harvested immediately after 15 minutes of light. Head extracts and western blots were performed as in FIG. 20A. Lane numbering corresponds to time (in hours) from the start of a 1 hour light pulse. (*), light treated. (D) All TIM bands shown in (C) were quantified by densitometry with reference to a constitutively produced, non-specific protein that cross-reacts with the TIM antibody [see (A, B)]. Dashed profile is light pulsed data.

FIGS. 21A–21E. Effects of light pulses on the phase of locomotor activity and TIM protein rhythms. (A) PRC of wild type flies. cn bw flies were entrained to an LD cycle for at least 3 days and then transferred to constant darkness. Ten minute pulses of light (~8000 lux) were administered at the indicated times. For each time point, the average phase of the locomotor activity rhythms of 16 pulsed flies was compared to that of 16 untreated control flies. Activity rhythms were assessed as described (Sehgal et al (1994); Vosshall et al (1994)). Standard errors of the mean were derived from at least three independent experiments for each time point. The graph depicts the phase change of the locomotor activity rhythm following a 10-minute light pulse as a function of circadian time. Subjective day is indicated by the stippled bar. (B) Response of TIM protein levels to a light pulse administered at ZT16 followed by transfer to constant darkness. (*), light pulsed flies. (C) Response of TIM protein levels to a light pulse administered at ZT23. As in (B), except that light exposure occurred at ZT23 instead of ZT16. Except as noted, methods were as described for light pulsed per$^0$ flies. (D) TIM bands shown in (B) were quantified by densitometry with reference to hsp70. (E) As hsp70 migrated past the region blotted, quantitation of TIM in (C) was performed against a non-specific, cross reacting protein as described (FIG. 20). Dashed profiles are light pulsed data.

FIGS. 22A–22H. TIM immunostaining observed in LD 12:12. Frontal sections of wild type heads show high levels of eye and brain staining at night (ZT22 and ZT20.5)(A, D, respectively) and low levels during the day (ZT1 and ZT7)(B, C). (E) TIM staining at CT6. (F) Pattern of staining in control, tim$^0$ head sections reared in DD. (G) TIM staining in cytoplasm, but not nuclei of eyes in per$^0$ flies reared in DD. (H) Higher magnification showing cytoplasmic and nuclear TIM staining in putative Lateral Neurons in wild type (ZT17). Circular structure is esophagus. Arrows in (A, and D) indicate labeling of photoreceptor nuclei. Filled arrowheads (A, D, and H) show staining of putative LNs. Open arrowhead (G); cytoplasmic staining of per$^0$ photoreceptors. For "Dark" time points, flies were collected and frozen under a safelight (15W bulb with Kodak GBX-2 filter). Sectioning, and immunostaining of heads performed as described (Vosshall et al (1994)). Except as noted, light pulses were administered as described.

FIG. 23A–23F. Time course of light dependent loss of TIM in wild type photoreceptors and putative LNs. Flies entrained to LD12:12 and exposed to a 10 min light pulse (23) delivered at ZT16 were collected at ZT17 (D), ZT18 (E), and ZT21 (F). Control flies (not light pulsed) collected at ZT17 (A), ZT19 (B), and ZT21 (C). Examples of TIM staining in photoreceptor nuclei (arrows) and putative LNs (arrowheads) are indicated in (A, B, C and D).

Figure 24:
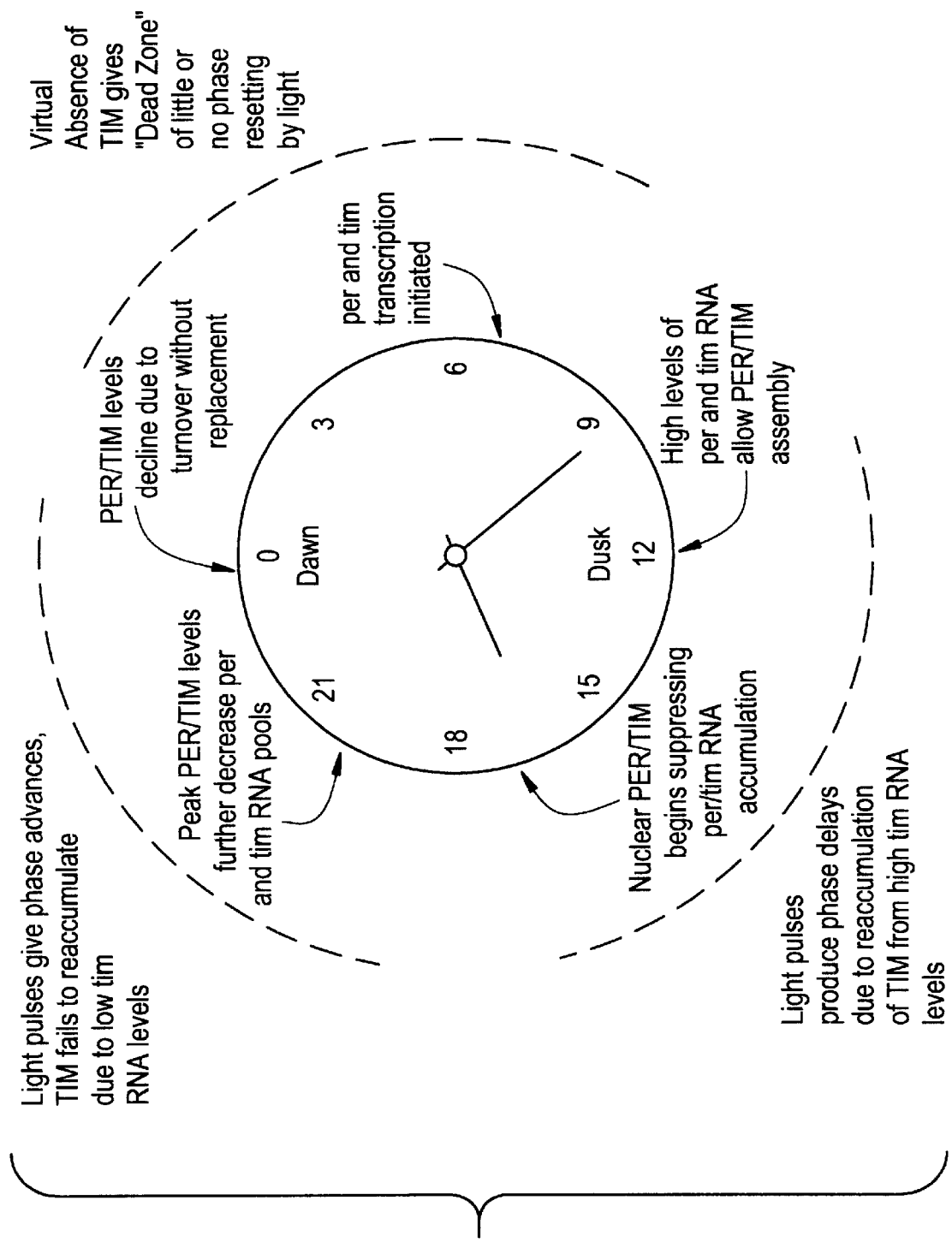

FIG. 24. Model for entrainment of the circadian pacemaker. As TIM protein appears to be an essential component of the Drosophila clock (Sehgal et al (1995)), and is rapidly degraded by light, the phase of molecular and behavioral rhythms should be altered by light at times of day when TIM proteins are present. tim RNA is most abundant in the early evening, at which time light pulses only transiently eliminate TIM proteins as they can be re-synthesized from existing RNA pools. If TIM suppresses accumulation of tim and per RNA (Sehgal et al (1995)), the extended interval of TIM accumulation should delay subsequent rounds of RNA synthesis. Lowest amounts of tim RNA are observed near dawn (Sehgal et al (1995)). Light pulses at that time prematurely eliminate TIM, which cannot be replaced until new tim RNA synthesis ensues with the following day' cycle. Premature elimination of TIM by light should lead to advanced synthesis of tim and per RNA.

DETAILED DESCRIPTION OF THE PREFERRED EMBODIMENTS OF THE INVENTION

In the fruit fly Drosophila melanogaster, two genes are essential components of the circadian clock, period and timeless (Sehgal et al (1994)). Mutations in either of these genes can produce arrhythmicity or change the period of the rhythm by several hours (Konopka and Benzer (1971); Sehgal et al (1994)). Molecular studies (Bargiello et al Proc. Natl. Acad. Sci. U.S.A. 81:2142 (1984); Reddy et al Cell 38:701 (1984); Myers Science 270:805 (1995); Hardin et al. Nature 343:536 (1990); Sehgal et al, (1995)) have shown that per and tim are transcribed with indistinguishable circadian rhythms that are influenced by an interaction of the TIM and PER proteins (Sehgal et al. (1994); Gekakiset et al Science, 270:811 (1995)). A physical association of the two proteins appears to be required for accumulation and nuclear localization of PER (Sehgal et al (1994); Gekakiset et al. (1995); Price et al. EMBO J., 14:4044 (1995)). It is likely that nuclear localization leads to suppression of per and tim transcription (Hardin et al. Nature, 343:536 (1990); Sehgal et al. (1995)). Cycles of gene expression are thought to be sustained by '5 hour differences in the phases of RNA and protein accumulation. The observed delays in PER accumulation may result, in part, from a requirement for TIM to stabilize PER (Sehgal et al (1994); Sehgal et al (1995); Price et al (1995)).

More particularly, the present invention relates to a factor involved in nuclear localization of proteins, and which is associated with circadian rhythms. In particular, the invention relates to the tim gene, which codes for the Timeless protein. Timeless is the second gene which has been associated with circadian rhythms in Drosophila, the first gene being per, which codes for the protein Period.

In the absence of the Timeless protein, TIM, gene products, such as the Period protein, PER, are not stable in the cytoplasm. Upon binding to the Timeless protein, proteins such as PER are stabilized and translocated into the nucleus. Once in the nucleus, the proteins act to inhibit the production of their own RNA. Both the tim and per genes are transcribed cyclically, and this transcription drives behavior. In particular, the gene products are present in the cytoplasm late in the day when a sleeping cycle is induced, while when the gene products are in the nucleus late at night, and a waking cycle follows.

The TIM protein not only acts as a nuclear translocation factor for the PER protein, but the PER protein also serves as a nuclear translocation factor for the TIM protein, thus indicating that PER and TIM act as mutual and reciprocal nuclear translocation factors. The nuclear translocation of the PER-TIM heterodimer is a crucial step in the regulation of both tim DNA and per DNA transcription.

The TIM protein also plays an important role in entraining the circadian rhythm of Drosophila, and by analogy other animals, to environmental cycles of light. This property of the TIM protein is due to its requirement for stabilizing the PER protein; its role in regulating per DNA transcription; and the TIM protein's extreme sensitivity to light.

Unlike the PER protein which requires the TIM protein for stability, the stability of the TIM protein is independent of the PER protein.

The present invention relates to the discovery of a mutant strain of Drosophila, with a "clock mutation," i.e., a mutation in a gene associated with circadian rhythms. In particular, the gene is the tim gene, which has the sequences identified by SEQ ID NOS:1, 2 and 4. Such mutant flies and cells isolated from the flies are included within the invention.

The following are definitions of terms used herein: The terms "nuclear localization factor", "translocation factor", "nuclear translocation factor", and any variants not specifically listed, may be used herein interchangeably, and as used throughout the present application and claims refer to proteinaceous material including single or multiple proteins, and extends to those proteins having the amino acid sequence data described herein and presented in SEQ ID NOS:3 and 5 and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "nuclear localization factor," "translocation factor," and "nuclear translocation factor" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

TABLE OF CORRESPONDENCE

| SYMBOL | | |
| --- | --- | --- |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein. A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the MRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the -10 and -35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into MRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al, supra; DNA Cloning, Vols. I & II, supra; Nucleic Acid Hybridization, supra.

By "active fragments" is meant any portion of the nuclear translocation factor which is capable of specifically binding to a protein which becomes stabilized and translocated into the nucleus upon binding to that translocation factor or portion thereof.

It should be appreciated that also within the scope of the present invention are DNA sequences encoding nuclear translocation factors such as tim which code for a Timeless protein having the same amino acid sequence as SEQ ID NOS:3 or 5, but which are degenerate to SEQ ID NOS:1, 2 or 4. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Termination codon | UAA (ochre) or UAG (amber) or UGA (opal) |

It should be understood that the codons specified above are for RNA sequences. The corresponding codons for DNA have a T substituted for U.

Mutations can be made in SEQ ID NOS:1, 2 and 4 such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino acids with nonpolar R groups
    Alanine
    Valine
    Leucine
    Isoleucine
    Proline
    Phenylalanine
    Tryptophan
    Methionine Amino acids with uncharged polar R groups
    Glycine
    Serine
    Threonine
    Cysteine
    Tyrosine
    Asparagine
    Glutamine Amino acids with charged polar R groups (negatively charged at pH 6.0)
    Aspartic acid
    Glutamic acid Basic amino acids (positively charged at pH 6.0)
    Lysine
    Arginine
    Histidine (at pH 6.0)

Another grouping may be those amino acids with phenyl groups:
    Phenylalanine
    Tryptophan
    Tyrosine Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
    Lys for Arg and vice versa such that a positive charge may be maintained;
    Glu for Asp and vice versa such that a negative charge may be maintained;
    Ser for Thr such that a free —OH can be maintained; and
    Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')₂ and F(v), which portions are preferred for use in the therapeutic methods described herein. Fab and F(ab')₂ portions of antibody molecules are prepared by the proteolytic reaction of papain and pepsin, respectively, on substantially intact antibody molecules by methods that are well-known. See for example, U.S. Pat. No. 4,342,566 to Theofilopolous et al Fab' antibody molecule portions are also well-known and are produced from F(ab')₂ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash.

In its primary aspect, the present invention concerns the identification of a nuclear localization factor, and the isolation and sequencing of a particular nuclear localization factor, that is believed to be present in cytoplasm and that serves as a stabilizer and translocator of a particular cellular protein, which forms a complex with that cellular protein and enters the nucleus of the cell to inhibit transcription of both the nuclear localization factor and the cellular protein.

The present nuclear localization factor is likewise noteworthy in that its own transcription appears to be demonstrably affected by its own presence in the nucleus.

A particular nuclear localization factor identified herein by SEQ ID NOS:3 or 5, is believed to be present in cytoplasm and the nucleus and to serve as a stabilizer and a specific translocator of a protein involved in circadian rhythms in response to its specific binding to the nuclear translocation factor. This particular factor is also believed to inhibit transcription of its own RNA and that of the protein involved in circadian rhythms. Alternatively, it may be that it is the association of both the protein thought to be the nuclear localization factor and the protein thought to be involved in circadian rhythms which is required for both the functions of nuclear translocation and controlling circadian rhythms.

As stated above, the present invention also relates to a recombinant DNA molecule or cloned gene, or a degenerate variant thereof, which encodes a nuclear localization factor.

The possibilities both diagnostic and therapeutic that are raised by the existence of the nuclear localization factor or factors, derive from the fact that the factors appear to participate in direct and causal protein-protein interaction between the protein involved in circadian rhythms and the nuclear localization factor that is bound thereto, and those factors that thereafter directly interface with the gene and effect transcription and accordingly gene activation. As suggested earlier and elaborated further on herein, the present invention contemplates pharmaceutical intervention in the cascade of reactions in which the nuclear localization factor is implicated, to modulate its own activity, and the activity initiated by the protein involved in circadian rhythms.

The nucleic acids encoding the nuclear localization factor, including the Timeless protein and fragments thereof, and the proteins encoded thereby, can be used in the treatment of numerous sleep-related disorders, including depression, narcolepsy and other mental disorders linked to the sleep-wake cycle. These proteins and nucleic acids can also be used in the treatment of jet lag.

Thus, in instances where it is desired to reduce or inhibit the gene activity resulting from a particular stimulus or factor, an appropriate inhibitor of the nuclear localization factor could be introduced to block the interaction of the nuclear localization factor with those factors causally connected with gene activation. Correspondingly, instances where insufficient gene activation is taking place could be remedied by the introduction of additional quantities of the nuclear localization factor or its chemical or pharmaceutical cognates, analogs, fragments and the like.

The nucleic acids of the invention can be administered by any method known in the art, in particular by liposomes, gene "guns," transgenic methodologies, gene therapy and the like.

As discussed earlier, the localization factors or their binding partners or other ligands or agents exhibiting either mimicry or antagonism to the localization factors or control over their production, may be prepared in pharmaceutical compositions, with a suitable carrier and at a strength effective for administration by various means to a patient experiencing an adverse medical condition associated specific transcriptional stimulation for the treatment thereof. A variety of administrative techniques may be utilized, among them parenteral techniques such as subcutaneous, intravenous and intraperitoneal injections, catheterizations and the like. Average quantities of the recognition factors or their subunits may vary and in particular should be based upon the recommendations and prescription of a qualified physician or veterinarian.

Also, antibodies including both polyclonal and monoclonal antibodies, and drugs that modulate the production or activity of the recognition factors and/or their subunits may possess certain diagnostic applications and may for example, be utilized for the purpose of detecting and/or measuring conditions such as to classify groups of individuals with sleep-related disorders, in order to better treat the disorders. For example, the recognition factor or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the nuclear localization factors of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al, "Hybridoma Techniques" (1980); Hammerling et al, "Monoclonal Antibodies And T-cell Hybridomas" (1981); Kennett et al, "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against localization factor peptides can be screened for various properties; i.e., isotype, epitope, affinity, etc. Of particular interest are monoclonal antibodies that neutralize the activity of the localization factor or its subunits. Such monoclonals can be readily identified in localization factor activity assays. High affinity antibodies are also useful when immunoaffinity purification of native or recombinant localization factor is possible.

Preferably, the anti-localization factor antibody used in the diagnostic methods of this invention is an affinity purified polyclonal antibody. More preferably, the antibody is a monoclonal antibody (Mab). In addition, it is preferable for the anti-localization factor antibody molecules used herein be in the form of Fab, Fab', F(ab')$_2$ or F(v) portions of whole antibody molecules.

As suggested earlier, the diagnostic method of the present invention comprises examining a cellular sample or medium by means of an assay including an effective amount of an antagonist to a nuclear localization factor/protein, such as an anti-localization factor antibody, preferably an affinity-purified polyclonal antibody, and more preferably a Mab. In addition, it is preferable for the anti-localization factor antibody molecules used herein be in the form of Fab, Fab', F(ab')$_2$ or F(v) portions or whole antibody molecules. As previously discussed, patients capable of benefiting from this method include those suffering from cancer, a pre-cancerous lesion, a viral infection or other like pathological derangement. Methods for isolating the localization factor and inducing anti-localization factor antibodies and for determining and optimizing the ability of anti-localization factor antibodies to assist in the examination of the target cells are all well-known in the art.

Methods for producing polyclonal anti-polypeptide antibodies are well-known in the art. See U.S. Pat. No. 4,493,795 to Nestor et al, A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a localization factor-binding portion thereof, or localization factor, or an origin-specific DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present localization factor and their ability to inhibit specified transcriptional activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al, *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-localization factor antibodies are also well-known in the art. See Niman et al, *Proc. Natl. Acad. Sci. USA*, 80:4949–4953 (1983). Typically, the present localization factor or a peptide analog is used either alone or conjugated to an immunogenic carrier, as the immunogen in the before described procedure for producing anti-localization factor monoclonal antibodies. The hybridomas are screened for the ability to produce an antibody that immunoreacts with the localization factor peptide analog and the present localization factor.

The present invention further contemplates therapeutic compositions useful in practicing the therapeutic methods of this invention. A subject therapeutic composition includes, in admixture, a pharmaceutically acceptable excipient (carrier) and one or more of a nuclear localization factor, polypeptide analog thereof or fragment thereof, as described herein as an active ingredient. In a preferred embodiment, the composition comprises an antigen capable of modulating the specific binding of the present localization factor within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of localization factor binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the factor/factor synthesis promoter antagonist or analog thereof, and one or more of the following active ingredients: an antibiotic, a steroid. Exemplary formulations are given below:

Formulations

| Ingredient | mg/ml |
|---|---|
| Intravenous Formulation I | |
| cefotaxime | 250.0 |
| nuclear localization factor | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II | |
| ampicillin | 250.0 |
| nuclear localization factor | 10.0 |
| sodium bisulfite USP | 3.2 |
| disodium edetate USP | 0.1 |
| water for injection q.s.a.d. | 1.0 ml |
| Intravenous Formulation III | |
| gentamicin (charged as sulfate) | 40.0 |
| nuclear localization factor | 10.0 |
| sodium bisulfite USP | 3.2 |
| disodium edetate USP | 0.1 |
| water for injection q.s.a.d. | 1.0 ml |
| Intravenous Formulation I | |
| localization factor | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation V | |
| localization factor antagonist | 5.0 |
| sodium bisulfite USP | 3.2 |
| disodium edetate USP | 0.1 |
| water for injection q.s.a.d. | 1.0 ml |

As used herein, "pg" means picogram, "ng" means nanogram, "ug" or "$\mu$g" mean microgram, "mg" means milligram, "ul" or "$\mu$l" mean microliter, "ml" means milliliter, "l" means liter.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2 $\mu$ plasmid or derivatives thereof; vectors useful in eukaryotic cells, such as vectors useful in insect or mammalian cells; vectors derived from combinations of plasmids and phage DNAS, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli*, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that nuclear localization factor analogs may be prepared from nucleotide sequences of the protein complex/subunit derived within the scope of the present invention. Analogs, such as fragments, may be produced, for example, by pepsin digestion of nuclear localization factor material. Other analogs, such as muteins, can be produced by standard site-directed mutagenesis of nuclear localization factor coding sequences. Analogs exhibiting "nuclear localization factor activity" such as small molecules, whether functioning as promoters or inhibitors, may be identified by known in vivo and/or in vitro assays.

As mentioned above, a DNA sequence encoding nuclear localization factor can be prepared synthetically rather than cloned. The DNA sequence can be designed with the appropriate codons for the nuclear localization factor amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al, *Science*, 223:1299 (1984); Jay et al, *J. Biol. Chem.*, 259:6311 (1984).

Synthetic DNA sequences allow convenient construction of genes which will express nuclear localization factor analogs or "muteins". Alternatively, DNA encoding muteins can be made by site-directed mutagenesis of native nuclear localization factor genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create analogs with unnatural amino acids.

The present invention extends to the preparation of antisense nucleotides and ribozymes that may be used to interfere with the expression of the receptor recognition proteins at the translational level. This approach utilizes antisense nucleic acid and ribozymes to block translation of a specific MRNA, either by masking that MRNA with an antisense nucleic acid or cleaving it with a ribozyme.

Antisense nucleic acids are DNA or RNA molecules that are complementary to at least a portion of a specific MRNA molecule. (See Weintraub, 1990; Marcus-Sekura, 1988.) In the cell, they hybridize to that mRNA, forming a double stranded molecule. The cell does not translate an MRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into nuclear localization factor-producing cells. Antisense methods have been used to inhibit the expression of many genes in vitro (Marcus-Sekura, 1988; Hambor et al, 1988). Also contemplated by the invention are nucleic acids which bind to a double stranded nucleic acid as a third strand to inhibit transcription.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988). Because they are sequence-specific, only MRNAS with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target MRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave MRNAS for nuclear localization factor proteins and their ligands.

The present invention also relates to a variety of diagnostic applications, including methods for detecting the presence of stimuli such as the earlier referenced polypeptide ligands, by reference to their ability to elicit the activities which are mediated by the present nuclear localization factor. As mentioned earlier, the nuclear localization factor can be used to produce antibodies to itself by a variety of known techniques, and such antibodies could then be isolated and utilized as in tests for the presence of particular transcriptional activity in suspect target cells.

As described in detail above, antibody(ies) to the nuclear localization factor can be produced and isolated by standard methods including the well known hybridoma techniques. For convenience, the antibody(ies) to the nuclear localization factor will be referred to herein as $Ab_1$ and antibody(ies) raised in another species as $Ab_2$.

The presence of nuclear localization factor in cells can be ascertained by the usual immunological procedures applicable to such determinations. A number of useful procedures are known. Three such procedures which are especially useful utilize either the nuclear localization factor labeled with a detectable label, antibody $Ab_1$ labeled with a detectable label, or antibody $Ab_2$ labeled with a detectable label. The procedures may be summarized by the following equations wherein the asterisk indicates that the particle is labeled, and "NLF" stands for the nuclear localization factor:

A. $NLF^* + Ab_1 = NLF^*Ab_1$

B. $NLF + Ab^* = NLFAb_1^*$

C. $NLF + Ab_1 + Ab_2^* = NLFAb_1Ab_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance, the nuclear localization factor forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-nuclear localization factor antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, AMCA blue, Lucifer yellow, Texas Red and auramine. A particular detecting material is anti-rabbit antibody prepared in goats and conjugated with fluorescein through an isothiocyanate.

The nuclear localization factor or its binding partner(s) can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

Additional labelling systems include biotin-labelling, followed by binding to a labelled avidin, or binding to an avidin followed by binding to a labelled anti-avidin antibody. Another labelling system include the use of digoxin-conjugated antibodies, which are then bound to labelled anti-digoxin antibodies.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the nuclear localization factor may be radiolabeled and combined, for example, with antibodies or other inhibitors thereto, after which binding studies would be carried out. Solutions would then be prepared that contain various quantities of labeled and unlabeled uncombined nuclear localization factor, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of predetermined transcriptional activity or predetermined transcriptional activity capability in suspected target cells. In accordance with the testing techniques discussed above, one class of such kits will contain at least the labeled nuclear localization factor or its binding partner, for instance an antibody specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of the presence or capability of cells for predetermined transcriptional activity, comprising:

(a) a predetermined amount of at least one labeled immunochemically reactive component obtained by the direct or indirect attachment of the present nuclear localization factor or a specific binding partner thereto, to a detectable label;

(b) other reagents; and (c) directions for use of said kit.

More specifically, the diagnostic test kit may comprise:

(a) a known amount of the nuclear localization factor as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling the nuclear localization factor to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the nuclear localization factor and a specific binding partner thereto.

In accordance with the above, an assay system for screening potential drugs effective to modulate the activity of the nuclear localization factor may be prepared. The nuclear localization factor may be introduced into a test system, and the prospective drug may also be introduced into the resulting cell culture, and the culture thereafter examined to observe any changes in the transcriptional activity of the cells, due either to the addition of the prospective drug alone, or due to the effect of added quantities of the known nuclear localization factor.

The following examples are presented in order to more fully illustrate the preferred embodiments of the invention. They should in no way be construed, however, as limiting the broad scope of the invention.

EXAMPLE 1

Because an analysis of the molecular mechanisms that underlie circadian rhythms requires the identification of other components in the pathway, a genetic screen was conducted in order to isolate new mutations affecting biological rhythms in Drosophila. The mutagenesis was based on the mobilization of single P transposable elements, as described (Cooley et al *Science* 239:1121 (1988)). The transposase-encoding, Δ2-3 P element from the Engels 2 strain (Robertson et al *Genetics* 118:461 (1988)) was used to mobilize a P(ry+) mutator element derived from strain R702.1 (Sprading and Rubin *Cell* 34:47 (1983)). Strains containing single new insertions of P(Ry+) were made homozygous for the insertion.

Figure 1B:
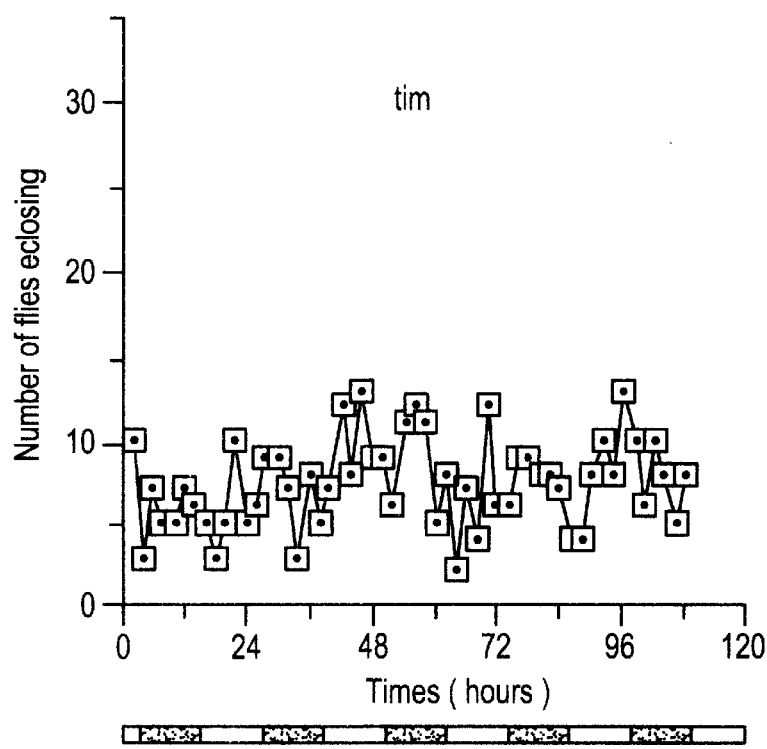

Approximately 7000 homozygous second or third chromosome lines were screened for altered eclosion rhythms as described (Konopka and Benzer (1971); Rosbash and Hall (1989); Baylies et al (1993)). Because wild-type flies emerge near dawn, cultures with large numbers of night-emerging adults were expanded for further analysis. Flies from one second chromosome line did not exhibit any preference for night or day emergence (Sehgal et al unpublished results). The arrhythmic eclosion pattern of the new mutant line was confirmed by monitoring eclosion at 2-hour intervals for 5 days in constant darkness (DD) after exposure to three cycles of LD 12:12 (FIG. 1). Wild-type flies under these conditions showed peaks of emergence at subjective dawn (FIG. 1A). No such discernible rhythm was found in the mutant flies in constant darkness (FIG. 1B).

EXAMPLE 2

Figure 2A:
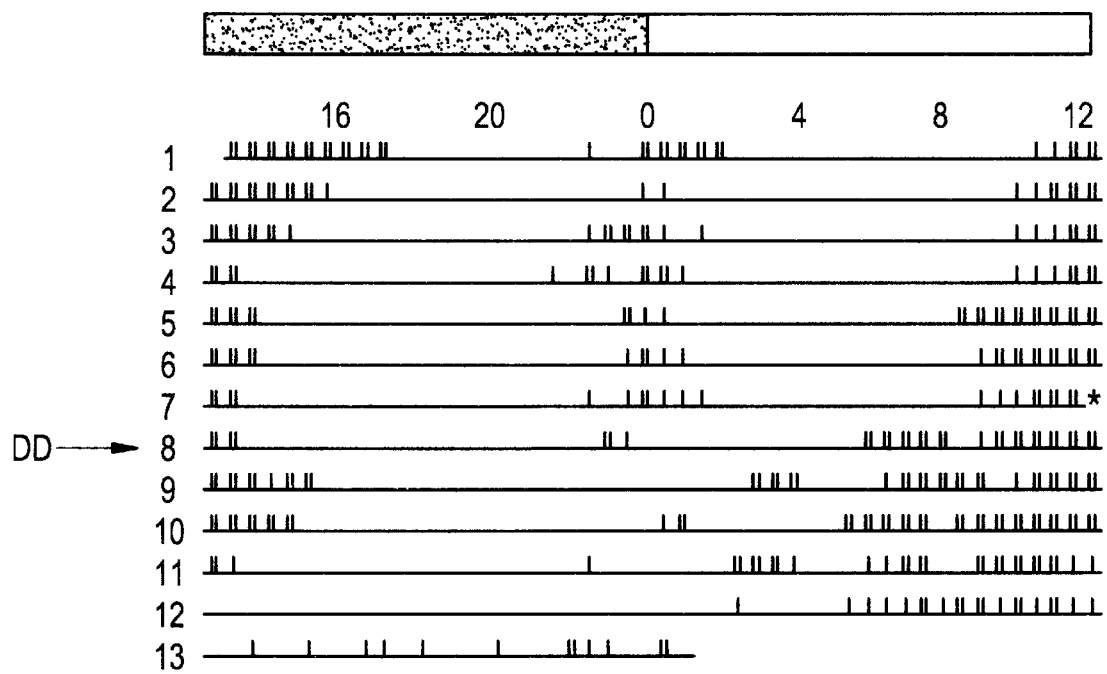
FIGS. 2A–2D. Locomotor activity profiles in tim flies. Shown are 13-day activity records from a wild-type (Canton S) fly (A) and from a tim fly (B). Drosophila cultures were maintained in a light:dark cycle (LD 12:12) for 3 days at 25° C. Adult flies from these cultures were etherized and placed individually in cylindrical glass tubes. Activity was then monitored at 25° C. (15) in the same LD 12:12 cycle for 7 days, and subsequently for 6 days in constant darkness (DD). Horizontal lines represent successive 24-hour intervals (top to bottom for each record). Activity corresponds to vertical deflections from the time lines. Time of day is indicated at the top of the records in Zeitgeber or circadian time (ZT0=lights on, ZT12=lights off during entrainment). For both records, the time indicated for each record with an arrow (DD). Portions of the records shown in (A) and (B) corresponding to constant darkness were subjected to chi square periodogram analysis (C and D) respectively (Hamblen et al *J. Neurogenet.* 3:249 (1986); Dowse et al *Behav. Genet.* 17:19 (1987)) (software obtained from Mini Mitter). Records were analyzed for evidence of periodicity in the 10- to 40-hour range. For each periodogram, the lower limit of statistical significance ($P<0.05$) is indicated by a sloping line. Prior analysis of several hundred wild-type flies by these methods indicated that ~90% produce robust, single peaks of activity with periodicities of 23 to 25 hours (Sehgal et al *Proc. Natl. Acad. Sci. U.S.A.* 89:1423 (1992)) like that shown in (C). In contrast, periodogram analysis of 407 of 436 tim flies (93%) showed no evidence of periodicity or showed weak multiple periodicities throughout the circadian and noncircadian range [the latter behavior is illustrated in (D)]. Twenty-nine of the 436 tim flies (7%) produced weak single periodicities that were seldom in the circadian range. In no case was circadian rhythmicity evident from visual inspection of the 436 records. Results similar to those for tim flies have been observed for $per^O$ flies (Sehgal et al, unpublished results; Hamblen et al *J. Neurogenet.* 3:249 (1986); Dowse et al *Behav. Genet.* 17:19 (1987)).
Figure 2B:
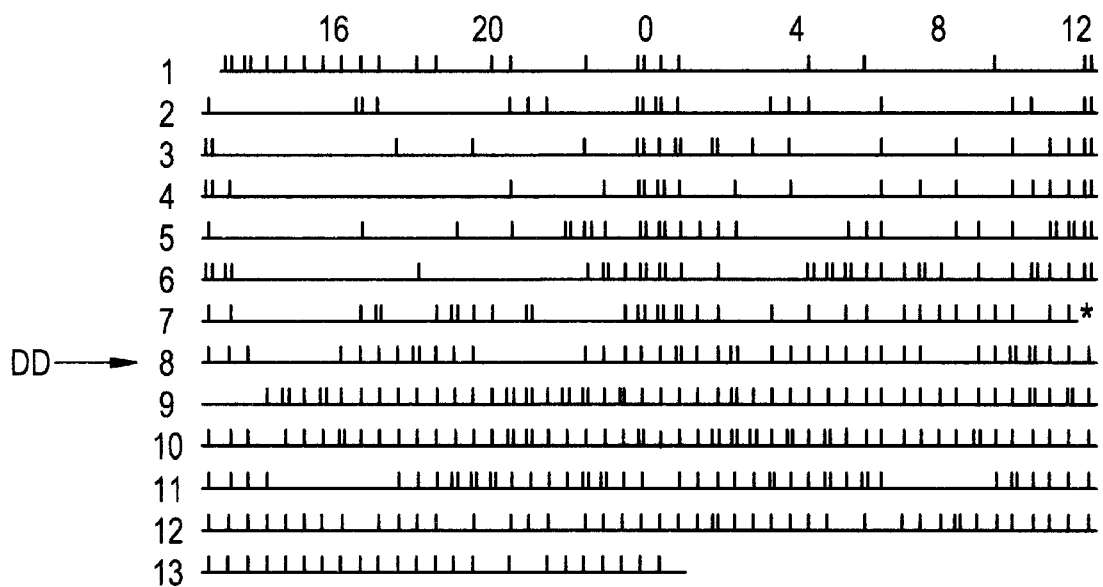
Figure 2C:
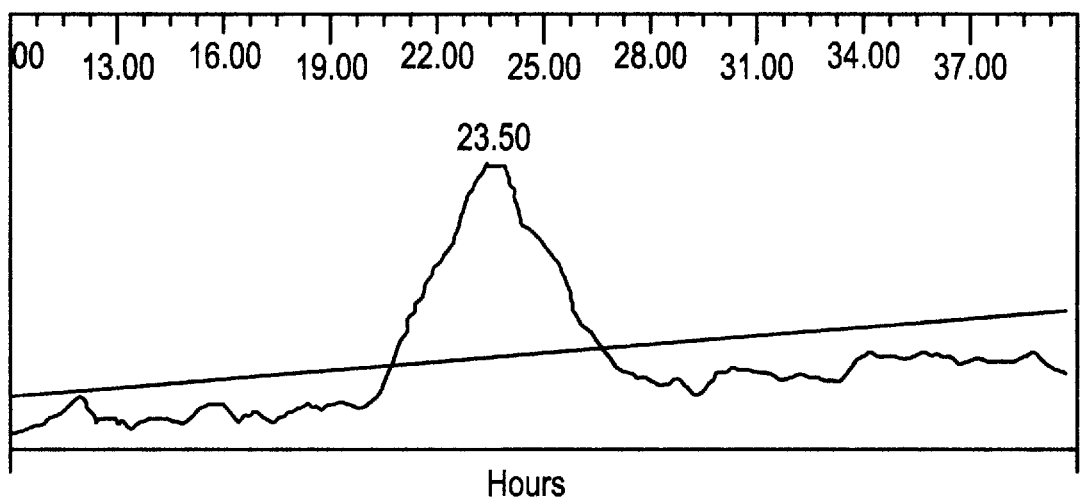
Figure 2D:
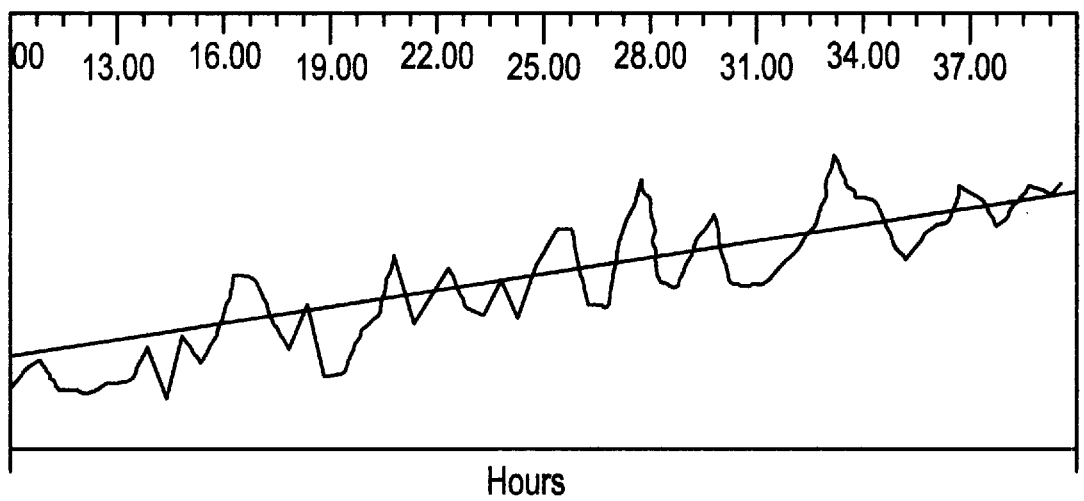

Some Drosophila clock mutants share effects on both eclosion and locomotor activity rhythms (Jackson (1993); Konopka and Benzer (1971); Rosbash and Hall (1989); Baylies et al (1993) Jackson (1983); Dushay et al (1989); Dushay et al (1990); Konopka et al (1991)). To determine whether the new mutation also affects locomotor activity, mutant flies were monitored for 7 days in LD 12:12 and subsequently for 6 days in DD. Wild-type flies showed rhythmic behavior in LD 12:12, with peaks of activity each morning and evening (FIG. 2A). These rhythms persisted in wild-type flies in DD, albeit with a less obvious bimodality (FIG. 2A). In contrast, although they were responsive to LD cycles, flies from the mutant line became arrhythmic when the LD cycle was removed (FIG. 2B). In this regard, the behavior of the new mutant resembles that produced by per$^0$ (Konopka and Benzer (1971); Rosbash and Hall (1989); Baylies et al (1993); Sehgal et al, unpublished results; Helfrich and Engelmann Z. *Naturforsch* 42C: 1335 (1987); Hamblen-Coyle et al *J. Insect. Behav.* 5:417 (1992); Wheeler et al *J. Biol. Rhythms* 8:67 (1993)). The rhythmic activity displayed by flies of both genotypes in the presence of light:dark cycles may be a forced response to LD as described (Helfrich and Engelmann (1987); Hamblen-Coyle et al (1992); Wheeler et al (1993)) and not indicative of an underlying circadian clock (Helfrich and Engelmann (1987); Hamblen-Coyle et al (1992); Wheeler et al (1993)). Thus far, over 400 flies of the mutant line have been analyzed for evidence of locomotor activity rhythms. Periodogram analysis (Hamblen et al J. Neurogenet. 3:249 (1986); Dowse et al *Behav. Genet.* 17:19 (1987)) and visual inspection of locomotor activity records failed to detect clear circadian rhythmicity in DD in any of the tim flies (FIG. 2).

The new clock mutation was localized on chromosome 2 by genetic recombination (Table 1) and is recessive.

Table 1. Recombination mapping of tim relative to markers on the left arm of chromosome 2. The genotypes of chromosomes that had recombined between tim, Sp and J (cross 1), between tim and dp (cross 2), or between tim and dpp (cross 3) are shown (recombinant chromosomes). Also indicated are the frequencies of such events (number of lines with the indicated recombinant genotype versus the total number of lines tested). The data indicate a location for tim that is approximately 17 map units distal to Sp, 5 map units distal to dp, and 3 map units proximal to dpp. Comparable tests with other markers on chromosome 2 (including fy, nub, b, cn, L, Pin, and or) were consistent with this placement of tim (Sehgal et al, unpublished results).

| Parental chromosomes | | | Recombinant chromosomes | | | Frequency |
|---|---|---|---|---|---|---|
| | | | Cross 1 | | | |
| + | Sp | J | + | + | + | 15/126 |
| tim | + | + | + | + | J | 1/126 |
| | | | tim | Sp | J | 6/126 |
| | | | tim | Sp | J | 0/126 |
| | | | + | Sp | + | 11/126 |
| | | | tim | + | J | 2/126 |

Although a site of P(ry+) hybridization mapped to the right arm of the affected chromosome (53A–C) and genetic recombination placed the ry+ marker at the same position, the site of insertion was not associated with the clock mutation.

Hybrid dysgenesis can induce P element excision mutations that ultimately have few or no P element sequences. (Kidwell, in Drosophila: *A Practical Approach*, D. B. Roberts, Ed. (IRL Press, Oxford, 1986), Chap. 3; Daniels and Chovrick *Genetics* 133:623 (1993); and Engels et al *Cell* 62:515 (1990)). Rather, mapping studies with various dominant and recessive markers showed that the behavioral mutation is located on the left arm of chromosome 2 distal to *Sternopleural* (*Sp*), which is located at 2-22 (Table 1). Further recombination mapping was carried out with markers in the region extending from 2-0 to 2-16. The mutation, which is referred to as timeless (tim), maps between decapentaplegic (dpp) and dumpy (dp) (Table 1). None of the previously isolated clock mutations of Drosophila maps to this chromosomal interval (Jackson (1993); Konopka and Benzer (1971); Rosbash and Hall (1989); Baylies et al (1993); Jackson (1983); Dushay et al (1989); Dushay et al (1990); Konopka et al (1991)). Furthermore, the tim mutation has not been associated with any obvious morphological or developmental change. Preliminary inspection of the anatomy of the nervous system in embryos, and of the brain and visual system in adults, also failed to distinguish tim mutants from wild-type Drosophila (Sehgal et al, unpublished results).

EXAMPLE 3

Figure 3A:
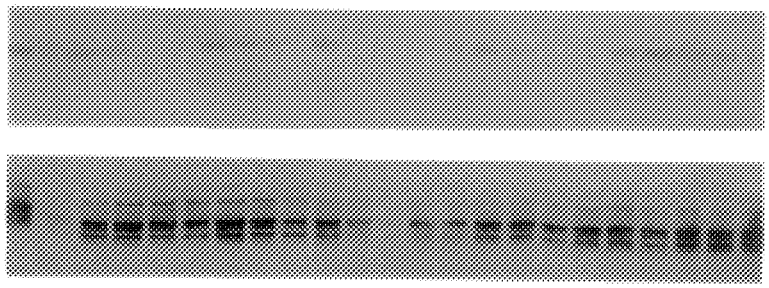
FIGS. 3A–3F. Amounts of per RNA accumulation in the heads of wild-type, $per^O$, and tim flies in LD cycles. The per RNA amounts were assayed in RNase protection assays. Wild-type (Canton S), $per^O$, and tim flies were contemporaneously entrained as follows: 0- to 5-day-old adult flies were transferred to fresh bottles and maintained in LD 12:12 at 25° C. for 3 days. Beginning on the fourth day, collections were made at ZT2, 6, 10, 14, 18, and 22 (ZT0=lights on).
Figure 3B:
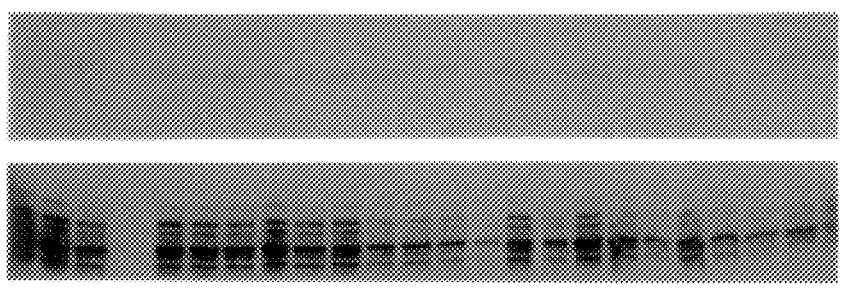
Figure 3C:
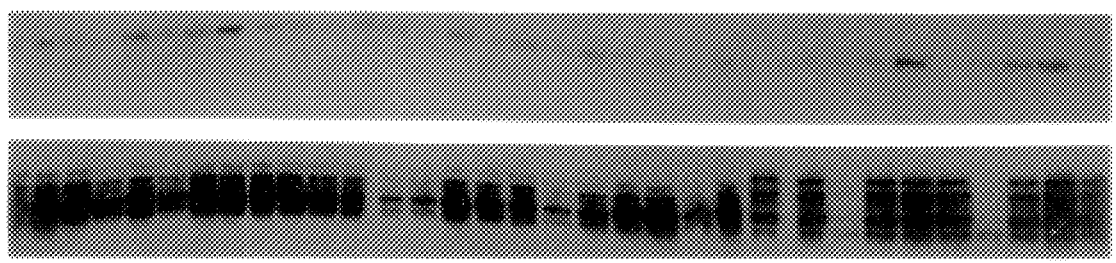
Figure 3D:
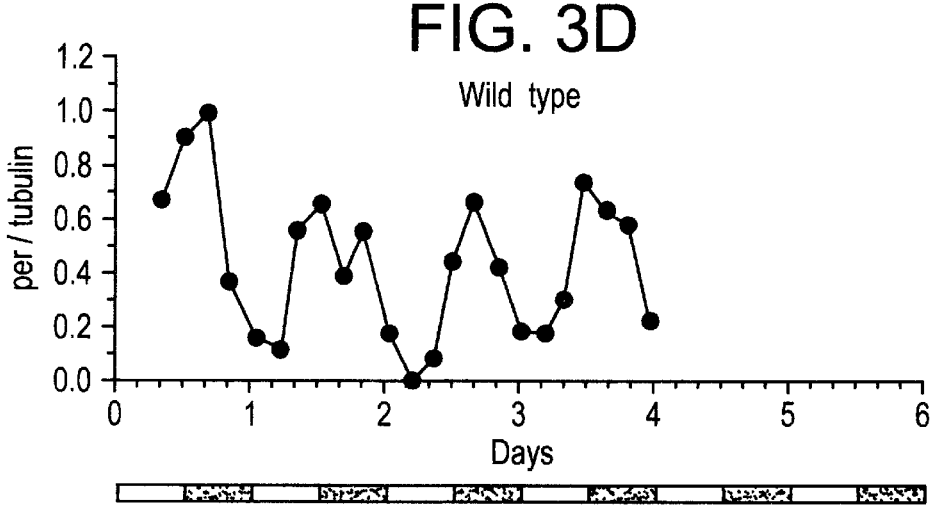
Figure 3E:
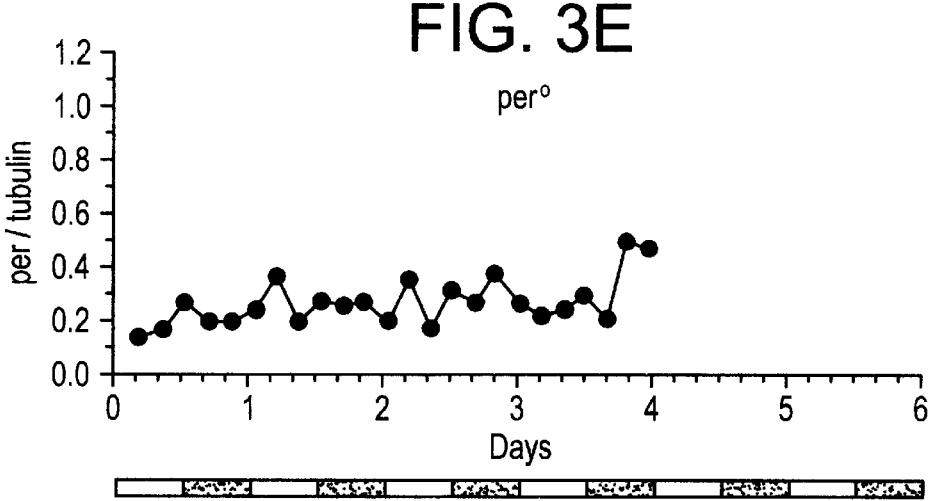
Figure 3F:
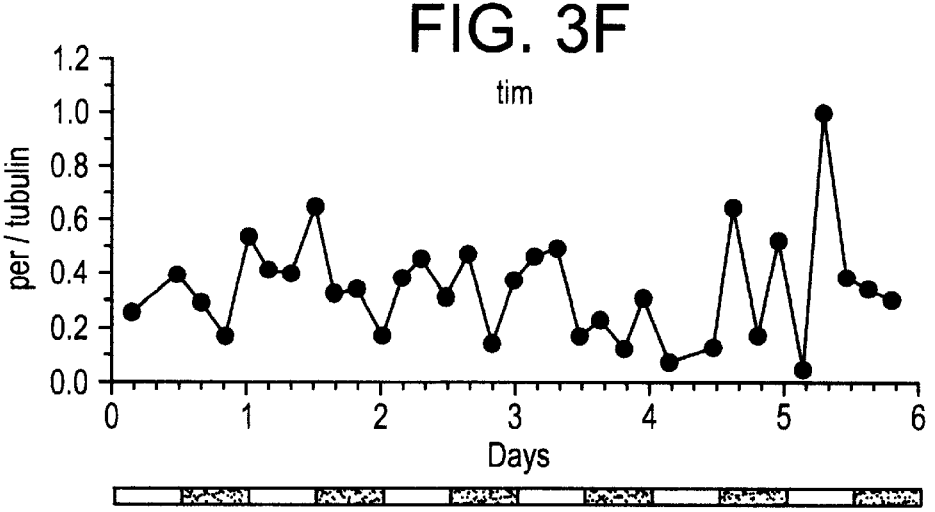

Both per mRNA and protein are expressed with a circadian rhythm in adults (Siwicki et al (1988); Zerr (1990); Edery et al (1994); Hardin et al (1990); Hardin et al (1992)). These oscillations are detectable in total RNA extracted from adult heads and have an altered phase in $per^S$ and $per^L$ flies. The oscillations are abolished in $per^O$ flies. The cycling RNA and protein, therefore, are useful molecular markers for circadian rhythmicity and may be molecular components of a central circadian pacemaker that drives downstream behavioral rhythms. Because tim mutants are arrhythmic for both eclosion and locomotor activity, per MRNA cycling was assessed in tim flies (as described above). In agreement with Hardin et al (1992), wild-type flies showed peaks of per RNA accumulation each evening, at about Zeitgeber time 14 (ZT14; ZT0=lights on, ZT12=lights off). The smallest amount of accumulation occurred around ZT2. This cycling can be seen in the autoradiographs of protected per mRNA (FIG. 3A) and in the graph of per mRNA abundance (FIG. 3B), in which data from FIG. 3A were quantitated with a phosphorimager and graphically plotted. As previously shown Hardin et al (1992), FIG. 3 also indicates that $per^O$ flies, when monitored over a 4-day interval in LD 12:12, did not exhibit circadian oscillations of per RNA.

The pattern of per mRNA accumulation in tim flies also differed from the wild-type pattern. Although fluctuations of per RNA were observed in the tim mutant over six LD 12:12 cycles (FIGS. 3, A and B), these fluctuations were usually of much lower magnitude than in the wild type and showed no evidence of circadian or noncircadian rhythmicity. Similar results were obtained in each of four independent experiments (including that depicted in FIG. 3) with RNA collections representing 16 LD 12:12 cycles. In no case did per mRNA levels appear to be rhythmic in a tim background.

The effect of tim on per RNA oscillation suggests an interaction between these two loci. More evidence for this interaction has been obtained by studying the expression of PER protein in tim flies (Vosshall et al Science 263:1606 (1994)), where the tim mutation was found to block nuclear localization of the PER protein. Because PER protein has been proposed to transcriptionally regulate expression of its own RNA Hardin et al (1992), perhaps its exclusion from the nucleus in tim flies accounts for the lack of per RNA oscillation. These data establish a functional interaction between tim and per that appears to be central to the control of circadian rhythms in Drosophila.

EXAMPLE 4

PER protein expression in wild-type, $per^O$ mutant, and tim mutant flies by staining head sections with PER antibody were compared. Because the amounts of PER protein staining in eye and brain nuclei fluctuate daily (Siwicki et al (1988); Saez and Young (1988); Zerr et al (1990)), sections were prepared in wild-type time points. Nuclear staining in wild-type photoreceptor cells was most prominent at Zeitgeber times 2 and 20 (ZT2 and 30) (Zeitgeber time (ZT) is an arbitrary standard for measuring time; ZT0 is defined as lights on or dawn, and ZT12 is defined as lights off or dusk), intermediate at ZT7, and absent at ZT13 (FIG. 4A).

Because the $per^O$ mutation introduces a stop codon in the PER reading frame (Baylies et al (1993); Rosbash and Hall (1989)), PER antibody specificity was demonstrated by the absence of staining in sections from this null mutant at each time point (FIG. 4C). In tim mutants, nuclear staining was not seen at any time point (FIG. 4B).

EXAMPLE 5

Figure 6A:
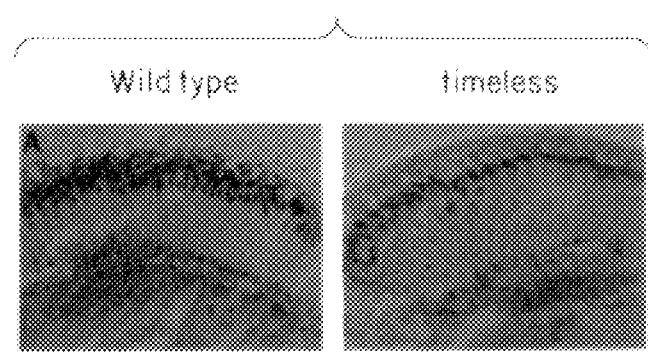
Figure 6B:
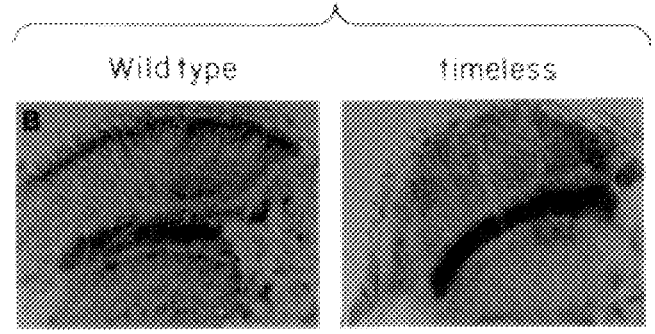

PER-β-galactosidase (PER-β-gal) fusion proteins have been used extensively to study patterns of per locus expression (Liu et al (1988); Liu et al (1991); Liu et al (1992); Ewer (1992); Huang et al Nature 364:259 (1993); Zwiebel et al Proc. Natl. Acad. Sci. U.S.A. 88:3882 (1991)). Such fusion proteins have also allowed the functional dissection of the gene and the encoded protein (Liu et al (1988); Liu et al (1991); Liu et al (1992); Ewer (1992); Huang et al Nature 364:259 (1993); Zwiebel et al Proc. Natl. Acad. Sci. U.S.A. 88:3882 (1991)). To explore the effect of tim on PER protein expression and to map elements of the per locus responding to tim, patterns of expression of a PER-β-gal fusion protein (PER-SG) (Liu et al (1988); Liu et al (1991); Liu et al (1992); Ewer (1992)) in transgenic flies were compared with a wild-type or tim mutant genetic background. PER-SG contains the $NH_2$-terminal half of PER (amino acids 1 to 636) (Baylies et al (1993)) fused to β-gal. The expression of PER-SG in transgenic flies in vivo (Liu et al (1988); Liu et al (1991); Liu et al (1992); Ewer et al (1992)) closely matches that of the endogenous protein (Siwicki et al (1988); Saez and Young (1988); Zerr et al (1990)). Whereas PER-SG localized to nuclei in wild-type flies, it was found that nuclear localization was blocked in tim mutants. Although no nuclear staining was observed in tim mutants, PER-SG accumulated in the same tissues in both tim and wild-type flies (FIGS. 5, A and D, and FIG. 6B). Specificity of the β-gal antibody used in these studies was indicated by the complete absence of staining in sections derived from wild-type or tim flies lacking the transgene that encodes PER-SG (L. B. Vosshall, thesis, Rockefeller University (1993)).

EXAMPLE 6

To determine whether a single mutation causes both aberrant intracellular localization of PER and the arrhythmic behavior of tim flies, recombinants were generated between the second chromosome bearing the PER-SG construct and the tim mutant chromosome. Head sections prepared from each of 36 homozygous tim+or tim recombinant lines (17 $tim^+$ and 19 tim) were stained with β-gal antibody. The PER-SG fusion protein was unclear in all 17 $tim^+$, PER-SG recombinant lines. Nuclear localization was not observed in any of the 19 tim, PER-SG recombinants (L. B. Vosshall, thesis, Rockefeller University (1993); L. B. Vosshall, J. Price, M. W. Young, unpublished observations). Therefore, mutant behavioral and localization phenotypes are likely to be the result of the same mutation. Representative sections from three independent $tim^+$, PER-SG recombinant (with nuclear labeling in the photoreceptor, cone, and pigment cells in the eye and in the lamina, medulla, and central brain) are shown in FIG. 5, A through C. Representative sections from tim, PER-SG recombinant show that nuclear localization of the PER-SG protein was not observed in any of these cells (FIG. 5, D through F).

EXAMPLE 7

The intracellular localization of the PER-SG fusion protein in $tim/tim^+$ heterozygotes was examined to learn whether the aberrant localization phenotype is a dominant or a recessive trait. PER-SG fusion proteins localize to nuclei in the heterozygotes (L. B. Vosshall, J. Price, M. W. Young, unpublished observations). Therefore, like the behavioral defect (Sehgal et al *Science* 263:1603 (1994)), the nuclear localization defect of tim is recessive. The nuclear localization of PER-SG in tim$^+$ flies also is not dependent on the presence of endogenous PER protein because its localization was nuclear in a per$^O$ genetic background (Vosshall et al, unpublished observations). Thus, neither functional PER protein nor behavioral rhythmicity is required to generate correct nuclear localization of the PER-SG fusion protein in tim$^+$ flies. As well, the tim mutant localization phenotype was independent of endogenous PER, because PER-SG fusion protein did not localize to nuclei in per$^O$; tim double mutants (Vosshall et al, unpublished observations).

To search for possible differences in the rate of synthesis, stability, or structure of PER-SG proteins isolated from wild-type and tim mutant flies, protein immunoblots were prepared from tim$^+$, PER-SG and tim, PER-SG head extracts. PER-β-gal fusion proteins of the same apparent size and abundance were detected in the two genetic backgrounds (FIG. 5G). Thus, effects on nuclear localization observed immunocytochemically in tim flies are not the result of reduced expression or increased proteolysis of the fusion protein.

EXAMPLE 8

To explore the specificity of the block in nuclear localization in tim mutants, the expression in tim mutants of two β-gal maker proteins (containing no PER sequences) that had been modified by the addition of heterologous nuclear localization signals and are expressed in the nuclei of the eye and brain was examined. The addition of such nuclear localization signals is required for nuclear localization of β-gal in wild-type flies (L. B. Vosshall, thesis, Rockefeller University (1993); L. B. Vosshall, J. Price, M. W. Young, unpublished observations; Smith et al *Science* 254:1478 (1991)). Nuclear localization of these marker proteins was unaffected by tim (FIG. 6, D and E). The tim mutation affected neither the morphology nor the number of nuclei visualized by these markers.

The localization of four additional PER-β-gal fusion proteins in tim mutants and wild-type flies was examined. Fusion proteins contained the first 23 amino acids of PER (PER1-23β-gal), PER amino acids 1 to 95 and 530 to 636 (PER-SGΔ96-529), the first 95 amino acids of PER (PER1-95β-gal), or the NH$_2$-terminal half of PER without a putative nuclear localization signal (PER1-636ΔNLS[66–79]β-gal) (Baylies et al (1993)).

Figure 6C:
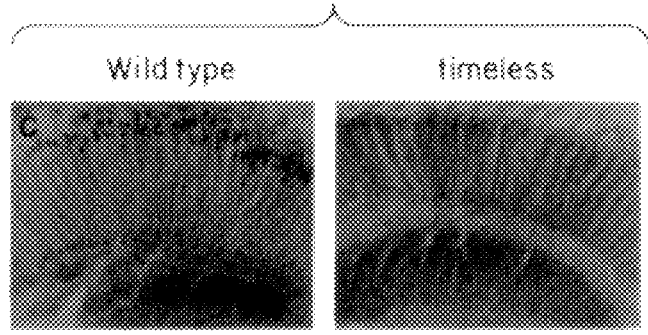
Figure 6D:
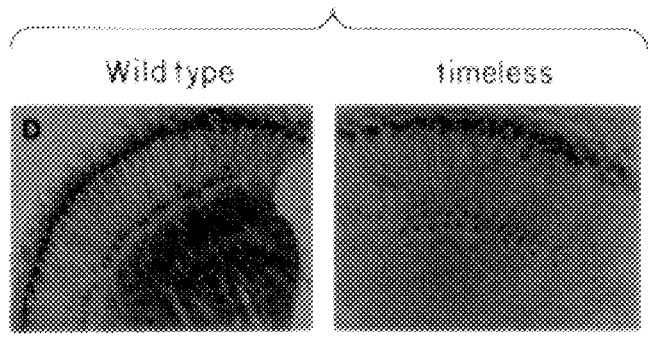
Figure 6E:
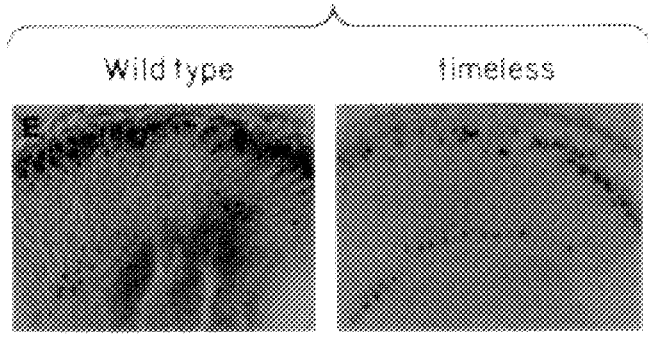

The pattern of PER1-23β-gal expression in wild-type and tim genetic backgrounds was identical to that of PER-SG in tim mutants (L. B. Vosshall, thesis, Rockefeller University (1993); L. B. Vosshall, J. Price, M. W. Young, unpublished observations). Because no sequences resembling a nuclear localization signal are found in this segment of the PER protein, cytoplasmic accumulation of this fusion protein was predicted for both genetic backgrounds (L. B. Vosshall, thesis, Rockefeller University (1993); L. B. Vosshall, J. Price, M. W. Young, unpublished observations; Smith et al *Science* 254:1478 (1991)). PER-SGΔ96-529 was nuclear in wild-type and tim flies (Vosshall et al, unpublished observations). The localization of PER1-95β-gal also was nuclear in wild-type (FIG. 6A, left) and tim backgrounds (FIG. 6A, right), which indicates that sequences in this NH$_2$-terminal region of PER would promote nuclear localization of a full-length PER protein but are unable to do so in tim mutant flies unless another, more centrally located region of PER is deleted. PER1-636ΔNLS[66–79]β-gal localized to nuclei in wild-type tissue (FIG. 6C, left), which indicates that PER contains additional nuclear localization signals. PER1-636ΔNLS[66–79]β-gal failed to enter nuclei in a tim background (FIG. 6C, right). Together, these results suggest that wild-type tim activity is required for nuclear localization of proteins that contain a specific region of PER. Because both PER1-95β-gal and PER-SGΔ96-539 are nuclear in tim files, the tim-sensitive region of PER must be located between amino acids 96 and 529. This interval includes the site of the per$^L$ mutation and the PAS domain (Baylies et al (1993), Rosbash and Hall (1989)), but would not include the pe$^S$ domain, a region in which mutations predominantly confer short-period phenotypes (Baylies et al *Neuron* 8:575 (1992)).

Four principal conclusions were drawn from this work. (i) The tim gene is required for nuclear localization of PER. (ii) Aberrant behavioral and localization phenotypes appear to be a result of the same mutation. (iii) Regulation of nuclear localization by tim may be specific for PER. (iv) PER contains sequences that somehow inhibit PER nuclear localization in the absence of tim. A protein encoded by tim might interact with PER to facilitate nuclear entry, or tim may regulate factors responsible for cytoplasmic retention of PER protein. The arrhythmic behavior and lack of per RNA rhythms observed in tim mutants (Sehgal et al *Science* 263:1603 (1994)) are likely to be a direct consequence of the failure of PER to enter the nucleus. Thus, PER must be present in the nucleus at some time of day for expression of circadian rhythms. Detection of large amounts of cytoplasmic PER-β-gal fusion protein, but not full-length cytoplasmic PER protein, in tim mutants may also indicate that PER is unstable in the cytoplasm and stabilized by transport to the nucleus. Thus, the observed cycling of PER protein abundance (Edery et al *Proc. Natl. Acad. Sci. U.S.A* 91:2260 (1994)) might reflect cycling of PER nuclear localization.

The region implicated in tim control of nuclear localization of PER includes the PAS domain, nonconserved sequences upstream of PAS (amino acids 96 to 232) (Colot et al *EMBO J.* 7:3929 (1988)), and 33 amino acids downstream of PAS (amino acids 497 to 529) (Crews et al *Cell* 52:143 (1988); Nambu et al *Cell* 67:1157 (1991); Huang et al *Nature* 364:259 (1993)). Regulation of nuclear localization has been observed for two other proteins containing the PAS domain. The dioxin receptor is a ligand-activated transcription factor (Denison et al *Proc. Natl. Acad. Sci. U.S.A.* 85:2528 (1988); Hapgood et al *Proc. Natl. Acad. Sci. USA* 86:60 (1989)) that accumulates in the cytoplasm until dioxin ligand interacts with the PAS domain of the AHR subunit (Burbach et al *Proc. Natl. Acad. Sci. U.S.A.* 89:8185 (1992)). This induces the formation of a complex with the ARNT subunit and promotes nuclear localization of the receptor complex (Fujisawa-Sehara et al *Proc. Natl. Acad. Sci. USA* 85:5859 (1988); Okey et al *J. Biol. Chem.* 255:11415 (1980)). In the absence of either ligand or ARNT, the receptor fails to enter nuclei and has no transcriptional activity (Reyes et al *Science* 256:1193 (1992); Hoffman et al *Neuron* 252:954 (1991)). No ligands or binding partners analogous to ARNT have been identified for PER. However, it has recently been shown that the PAS domain of the PER protein can function as a protein interaction domain (Huang et al *Nature* 364:259 (1993)). Further mapping of the tim-sensitive region of PER should determine whether PAS is centrally involved in the control of PER nuclear localization.

Peak amounts of per RNA expression (Hardin et al *Nature* 343:536 (1990); *Proc. Natl. Acad. Sci. U.S.A.* 89:11711 (1992); Sehgal et al *Science* 263:1603 (1994)) precede the greatest amount of PER protein straining in nuclei of the photoreceptors and brain (Siwicki et al (1988); Saez and Young (1988); Zerr et al (1990)) by about eight hours. Thus, nuclear immunoreactivity of PER occurs when the amount of per RNA is small. As suggested above, the entry of PER protein into the nucleus may be under temporal control, so that some of the previously observed oscillation in PER protein amounts and nuclear straining (Siwicki et al (1988); Saez and Young (1988); Zerr et al (1990)) may reflect rhythmic movement between the cytoplasm and the nucleus, with a phase that is distinct from the of per RNA synthesis. In light of these observations and work with tim, formation of an intracellular circadian clock may require nuclear localization of PER to be limited to a particular time of day.

In such a model, constitutively cytoplasmic (as in tim mutants) or constitutively nuclear PER would fail to generate circadian rhythms, and tim$^+$ activity might play a role in temporal regulation of the access of PER to the nucleus. It was proposed that PER may directly or indirectly regulate its own transcription, because the cycling of per transcription is blocked in per$^O$ mutants (Hardin et al (1990); Hardin et al (1992)). Because the tim mutation also abolishes these RNA rhythms (Sehgal et al *Science* 263:1603 (1994)), a form of feedback regulation may exist in which cycling nuclear localization of PER might produce rhythmic signals influencing per transcription. tim was recovered in a screen for clock mutations that was not biased to afford recovery of new mutations interacting with per (Sehgal et al (1994)). Thus, the discovery of functional interaction between tim and per indicates that a single intracellular mechanism is probably central to the generation of circadian rhythms in Drosophila. The effects of tim on per RNA oscillation and PER nuclear localization would presumably be components of this mechanism.

EXAMPLE 9

Positional cloning and sequence analysis of the Drosophila clock gene, timeless. The Drosophila genes timeless and period interact, and both are required for production of circadian rhythms. The positional cloning and sequencing of tim was undertaken. The tim gene encodes a previously uncharacterized protein of 1389 amino acids (SEQ ID NO:5), and possibly an alternate protein of 1122 amino acids (SEQ ID NO:3). The arrhythmic mutation tim$^{01}$ is a 64 bp deletion that truncates TIM to 749 amino acids. Absence of sequence similarity to the PER dimerization motif (PAS) indicates that direct interaction between PER and TIM would require a novel, heterotypic protein association.

The chromosome 2-linked timeless (tim) mutation produces phenotypes analogous to those of the mutation per$^O$: rhythmic eclusion, locomotor activity, and rhythmic expression of per mRNA are abolished (Sehgal et al supra). The latter observation indicates that the per and tim genes interact at some level. Additional evidence for such an interaction shows that tim+ activity is necessary for nuclear localization of a PER-βgal fusion protein expressed in transgenic flies (Vosshall et al *Science* 263:1606 (1994)). PER-βgal fusion proteins were readily detected in the cytoplasm of tim flies, but endogenous PER was not, which suggests that PER may be stabilized by transport to the nucleus in wild type flies (Vosshall et al supra). The PAS domain may control PER subcellular localization, because a PER fusion protein without a PAS-containing region was constitutively nuclear, even in tim flies (Vosshall et al supra). Western blot analyses of extracts from tim flies show that PER levels are very low and do not oscillate (Price et al (1995) *EMBO J*. 14:4044). As a result of these effects of the tim mutation on per MRNA and protein, it was proposed that a central aspect of the Drosophila clock might entail time-dependent nuclear localization of PER regulated by the product of tim (Vosshall et al supra).

The tim mutation was mapped to an interval between dpp and dp, that corresponds to approximately 2–3 MbP of DNA (Sehgal et al *Science* 263:1603 (1994)). Further recombination mapping localized tim to a region bounded by male-sex lethal 2 (msl-2) and odd-skipped (odd) (FIG. 12). A chromosome deficiency with breakpoints in polytene bands 23D and 23F [Df(2L)DTD62 $2^{P}3^{D}$; H7 $3^{P}2^{D}$ (Sekelsky et al (1995) *Genetics* 139:1347) genetically complemented the tim mutation and placed tim proximal to the deficiency breakpoint in 23F (FIG. 12A). This deficiency did not complement msl-2 (FIG. 12A), which made its breakpoint in 23F the nearest marker on the distal side of tim. A new deficiency chromosome was characterized that fails to complement the tim mutation, and it has been designated Df(2L)tim$^{02}$ (FIG. 12A) (Rothenfluh-Hilfiker and Young, unpublished data). Accordingly, the original tim mutation has been renamed tim$^{01}$. Cytological analysis of polytene chromosomes from Df(2L)tim$^{02}$ revealed loss of a portion of 23F (23F3-6) and possibly diminution of 24A1 (Rothenfluh-Hilfiker and Young, unpublished observations). Df(2L)DTD62 $2^{P}3^{D}$; H7 $3^{P}2^{D}$ and $^{Df}$(2L)tim$^{02}$ are each homozygous lethal, and genetic crosses between them failed to yield viable transheterozygotes, indicting that they overlap and disrupt at least one common essential gene. A set of three homozygous lethal deficiencies that remove Abnormal leg pattern (Df(2L) Alp77, Df(2L) Alp101, and Df(2L) Alp101 (S. Cohen, personal communication) complement tim$^{011}$ and Df(2L)tim$^{02}$, further reducing the interval containing tim since Alp is distal to odd (FIG. 12A).

To correlate the genetic and cytological maps with a physical map consisting of cloned DNA, P1-based genomic DNA clones and P-element insertion stocks were obtained which mapped to the region 23F-24A (J. Luchesi; W. Gelbart; Berkely Drosophila Genome Project). Additional clones from a chromosomal walk covering msl-2 were generously supplied by J. Lucchesi (Shubo et al (1995) *EMBO J*. 14:2884). End-specific DNA probes from the P1 and cosmid inserts were obtained by PCR (Wesley et al (1994) *Nucleic Acids Res*. 22:538), and DNA flanking each P element insertion was cloned by plasmid rescue (Pirrotta, in *Drosophila: A Practical Approach*, D. B. Roberts, Ed. IRL Press, Oxford, 1986), pp. 83–110). These probes were used in Southern blot analyses to produce a restriction map of the region and subclone an overlapping set of Eag I, Eco RI, and Bam HI fragments from the P1 clone 117, yielding a 60 kb contig (FIGS. 12B and C).

The proximal breakpoint in Df(2L)DTD62 $2^{P}3^{D}$; H7 $3^{P}$2D was mapped to the Eco RI fragment Ra6 by Southern blot analysis (M. P. Myers, unpublished observations), thereby providing a physical anchor for the distal border of the interval containing timeless (FIG. 12C). Southern blot analysis also revealed that DNA from the entire 60 kb contig is absent in Df(2L)tim$^{02}$, consistent with the genetic complementation tests. A DNA clone (B8) from a chromosomal walk covering Alp (Cohen, personal communication) overlaps with this contig (FIG. 12C), indicating that the proximal breakpoint in Df(2L)tim$^{02}$ must lie very near to the end of the contig yet leaves the Alp gene intact.

Because tim$^{01}$ was produced by a hybrid dysgenesis screen (Sehgal et al supra) rather than by chemical mutagenesis, it was reasoned that the causative lesion might involve a deletion or insertion of DNA that could be detected as a restriction fragment length polymorphism (RFLP).

Indeed, a Southern blot comparison of DNA from tim$^{01}$ and its wild type parental line (R702. 1TP) with the subclone Ec1 as probe detected RFLPs for the enzymes Eco RI and Hinf I. One of four Eco RI fragments detected by Ec1, a 2.2 kb fragment in the parental line, was reduced in size in DNA from tim$^{01}$ flies (FIG. 13A). The remaining Eco RI fragments displayed no change in size, signifying the presence of a small deletion within the 2.2 kb fragment in tim$^{01}$ flies. Two additional tim$^{01}$ sublines, established and separately maintained from the time of the mutant's initial recovery (Sehgal et al *Science* 263:1603), also showed evidence of this deletion upon Southern blot analysis (Myers, unpublished data). This indicated that the deletion arose in conjunction with the mutant phenotype. The Ec1 probe also detected a reduction in the size of one of several Hinf I fragments derived from tim$^{01}$ DNA. The change was estimated to be a deletion of about 70 bp (FIG. 13B). None of the other subclones in the contig detected RFLPs between DNA from tim$^{01}$ and R702. 1TP for the enzymes Eco RI, Bam HI, Hind III, Hinf I, Alu I, Fok I, Hae III, Rsa I, or Taq I (Myers, unpublished data). The location of the novel deletion in tim$^{01}$ flies also agrees well with the position of the mutation predicted from genetic recombination studies. tim$^{01}$ was located ~0.16 map units (2 recombinants/1248 tested chromosomes) proximal to msl-2, which should correspond to a physical distance of ~40–50 kb (Kidd et al (1983) Cell 34:421; Kelley et al *Cell* 51:539). Together these results strongly indicated that the identified deletion produces the tim mutant phenotype. Further evidence has been derived from sequencing the mutant DNA, and from the discovery that this gene is expressed with a circadian rhythm that is altered in per and tim mutants (Sehgal et al *Science* Nov. 3, 1995), and produces a protein that directly and specifically binds PER (Gekakis et al *Science* Nov. 3, 1995).

EC1 was used to screen a head-specific cDNA library (Hamilton et al (1991) *Nucleic Acids Res*. 19:1951). Several positive recombinant phage were purified, converted to plasmid clones, and the inserts restriction mapped. Clone 35c (Myers, unpublished data) extended the farthest in the 5' direction. The remaining cDNAs, 35a, d, e, g and 22g (Myers, unpublished data), although incomplete at their 5' ends, have identical 3' ends and contain a consensus polyadenylation signal. Combining the partial cDNAs at their sites of overlap yields a complete cDNA of 5,192 (SEQ ID NO:1). Sequencing all of 35c and significant portions of the other clones revealed an open reading frame coding for 1,122 amino acids (SEQ ID NO: 2 FIG. 11). To guard against possible artifacts in the cDNA library, genomic DNA (clones Ec1 and Ea1) was also sequenced to confirm the exon content (Myers, unpublished data). One of the cDNA clones, 22g, showed a deletion of 237 bp relative to the other cDNAs. The sequence missing from 22g corresponds to an intron retained in the other clones, with consensus 5' and 3' splice signals (FIG. 11). Its removal in 22g extends the open reading frame to 1,389 amino acids (SEQ ID NO:4 FIG. 11), yielding a protein with a predicted molecular mass of 156 kD. cDNAs encoding the longer form of TIM protein (i.e., lacking the 237 bp intron) were also obtained from an independently constructed head cDNA library as described in Gekakis et al (*Science* Nov. 3, 1995). Therefore, due to a retained intron in certain transcripts, there may be two forms of the TIM protein; each would share residues 1 to 1104 but possess different COOH-termini. Retained introns with varying degrees of coding potential have been observed for several genes (Breitbart et al (1987), in *Ann. Rev. Biochem.*, C. C. Richardson, Ed., Vol. 56, pp. 467–495). Given the likelihood that each from of TIM protein would have distinct activities, experiments to confirm the presence of the intron-bearing timeless transcripts are in progress. At a minimum, the 1,389 residue form of TIM is expected to be expressed and function in the adult fly head.

In order to characterize the deletion detected in tim$^{01}$, PCR was used to amplify and sequence DNA corresponding to the 2.2 kb Eco RI fragment from the parental line (R702. 1TP) and tim$^{01}$. A 64 bp deletion was discovered in the tim$^{01}$ DNA, very close to the size estimated from the Hinf I RFLP. The deletion causes a frame shift in the sequence encoding TIM, and the predicted translation product contains amino acids 1 to 714, with an additional 35 residues from the new reading frame (FIG. 11). The 64 bp deletion was confirmed to be the sole change in tim$^{01}$ that affects the translated product by sequencing all exons 5' of the deletion (data not shown). Thus, if stably expressed, the TIM protein in tim$^{01}$ flies is only about half its normal length and probably lacks activity. Moreover, since the phenotypes of tim$^{01}$/tim$^{01}$ and tim$^{01}$/Df(2L)tim$^{02}$ flies are indistinguishable, tim$^{01}$ is regarded as a null mutation.

TIM is a novel protein: database comparisons with either form yielded no significant homologies. Some general statements about the protein can be made from analysis of the amino acid sequence. First, there is no evidence of a signal sequence in the amino terminus, thus TIM is not likely to be a secreted protein or a cell surface receptor.

The TIM sequence contains a basic region (KKELRRKK) (SEQ ID NO:6) that could potential function as a nuclear localization signal (NLS). TIM also contains an extensive acid region (DDGDYEDQRHRQLNEHGEEDEDEDEVEEEE) (SEQ ID NO:7), a characteristic feature of the activation domain in some transcription factors. TIM is quite acidic overall, with a calculated isoelectric point of 5.14.

It was surprising to find an absence of sequence homology between PER and TIM, because, as shown below, there is a physical interaction between these two proteins that is mediated by PER's PAS domain (Gekakis et al *Science* Nov. 3, 1995). Earlier studies indicated that PAS containing proteins, including PER, can dimerize or associate with each other through homotypic interactions of their PAS domains (Huang et al, 1993 supra; Sogawa et al (1995) *Proc. Natl. Acad. Sci. USA* 92:1936). Nevertheless, careful inspection of the predicted TIM sequence in this study failed to indicate a region of homology to PAS. A heterotypic intra-molecular interaction of PAS with a distinct region of PER (the C-domain, residues 524–685) has been reported (Huang et al *Science* 267:1169 (1995)), but TIM shares no sequence similarity to this region either. Thus, with at least three different protein targets, the PAS domain in PER exhibits great flexibility in mediating protein-protein interactions. This may have implications regarding the number of potential interacting targets for other PAS-containing proteins.

As mentioned earlier, molecular cloning of tim has also allowed the discovery of circadian cycles in tim RNA expression (Sehgal et al *Science* Nov. 3, 1995). The combined molecular studies reveal a tight interplay between PER and TIM, and suggest a rudimentary intracellular biochemical mechanism regulating circadian rhythms in Drosophila. Further analysis of tim and its interactions with per is certain to shed new light on this central clock mechanism, and may eventually provide clues about how the clock is linked to output paths that yield observable rhythmic behaviors.

EXAMPLE 10

Isolation of timeless by per protein interaction:Defective interaction between timeless protein and long-period mutant PER$^L$. The period (per) gene likely encodes a component of the Drosophila circadian clock. Circadian oscillations in the abundance of per mRNA and per protein (PER) are thought to arise from negative feedback control of per gene transcription by PER. The recently-identified second clock locus, timeless (tim), apparently regulates entry of PER into the nucleus. Following the positional cloning of the tim gene (Example 9), the cloning of tim cDNA in a two-hybrid screen for PER-interacting proteins was performed and the physical interaction between the tim protein (TIM) and PER was demonstrated in vitro. A restricted segment of TIM binds directly to a part of the PER PAS dimerization domain. PER$^L$, a mutation that causes a temperature-sensitive lengthening of circadian period and a temperature-sensitive delay in PER nuclear entry, exhibits a temperature-sensitive defect in binding to TIM. These results suggest that the interaction between TIM and PER determines the timing of PER nuclear entry and therefore the duration of part of the circadian cycle.

PER oscillations almost certainly constitute a core element of the Drosophila circadian clock. These oscillations likely depend on the interaction of PER with other proteins, such as those predicted to regulate its subcellular localization or to constitute partners, effectors, or terminators of its transcriptional autoregulatory action. As a means of identifying novel components of the circadian clock, a yeast two-hybrid genetic screen (Fields et al (1989) *Nature* 340:245) was performed using a PER bait hybrid to isolate Drosophila head DNA library clones encoding PER-interacting proteins. The DNA-binding bait hybrid was LexA$_{1-202}$-PER$_{233-685}$ (Huang et al *Nature* 364:259 (1993)), corresponding to a segment of PER that is highly conserved among Drosophila species [H. V. Colot, J. C. Hall, M. Rosbash *EMBO J*. 7:39929 (1988)]; it contains the PAS domain and all of the sites of single amino acid substitutions that lead to long-period or short-period phenotypes (Dunlap *Annu. Rev. Physiol*. 55:683 (1993)). Drosophila head cDNA library clones were expressed as VP16 transactivator hybrids, and the host strain carried unlinked His 3 and Lac Z β-galactosidase) reporter genes downstream of LexA binding sites, as described [A. B. Vojtek, S. M. Hollenberg, J. Cooper, *Cell* 74:205 (1993)]. Because the PER fragment used as bait has been shown to homodimerize (Huang et al (1993)), a corresponding VP16-PER hybrid served as a positive control. For cDNA library construction, flies entrained to 12:12 light:dark cycles were collected at Zwitzeber times 2, 8,14, and 20, and total RNA was prepared from heads (Sehgal et al *Science* 263:1603 (1994)). An aliquot of 45 μg of total RNA was taken from each time-specific sample, the aliquots were pooled, and poly-A$^+$ RNA was prepared by aligo-dT chromatography (Oligotex-dT, Qiagen). Pooling of time-specific RNA samples was performed to maximize the likelihood that any transcripts exhibiting a circadian oscillation in abundance would be represented in the cDNA library. Random hexamer-primed, double-stranded cDNA was prepared from 2 μg of poly-A$^+$ RNA (Superscript Plasmid System, Gibco BRL) as suggested by the manufacturer, except that Not I-linkered and -digested cDNA's were size-selected by agarose gel electrophoresis. Fragments of size ≧1.5 kb were ligated to Not I-digested, dephosphorylated pVP16 [A. B. Vojtek, S. M. Hollenberg, J. Cooper, *Cell* 74:205 (1993)], the resulting ligation products were electroporated into *E. coli* strain DH-1OB (Gibco BRL), 2×10$^6$ transformants were plated at 10$^5$ colonies per 15-cm dish, and plasmid DNA was prepared from the bacterial colonies (Qiagen Plasmid Maxi Kit). Analysis of an arbitrarily-chosen population of plasmids indicated that ≧98% were recombinant and inserts ranged from 1.5 to 4kb. The library was introduced into the yeast reporter strain expressing the LexA-PER bait, and 2×10$^7$ resulting library transformants were screened for activation of the His 3 and Lac Z (β-galactosidase) reporter genes. The L40 reporter strain expressing the LexA-PER bait hybrid was transformed with the Drosophila head cDNA library (at efficiencies ≧10$^4$ per μg plasmid DNA) as described [D. Gietz, A. St. Hean, R. A. Woods, R. H. Shiestl *Nucleic Acids Res*. 20:1425 (1992); J. Hill, K. A. Ian, G. Donald, D. E. Griffiths *Nucleic Acids Res*. 19:5791 (1991)]. For solid-phase amplification of the library ≈10$^7$ transformants were plated at 10$^5$ colonies per 15-cm plate on TULL, a synthetic medium lacking tryptophan and leucine (to select for the bait and library plasmids, respectively) and uracil and lysine (to maintain the genomic loci at which the reporter genes were integrated). After 60 hrs. of growth at 30° C., colonies were removed from plates with a sterile scraper, resuspended in 600 ml of sterile water, pelleted at 4000 g for 10 min, and resuspended in 50 ml of sterile water. After thorough mixing, 20 μl was diluted into 2 ml of liquid TULL medium, the transformants were grown at 30° C. to one doubling (final A$_{600}$=0.8), pelleted, washed with sterile water, and a total of 2×10$^7$ transformants were spread onto 20 plates containing synthetic medium as above, but lacking histidine (THULL; to select additionally for activation of the His 3 reporter gene). This ten-fold over-screen of the CDNA library was performed to maximize the chance of detecting very rare clones. Plates were incubated at 30° C., and 360 His$^+$ colonies were patched to fresh THULL plates after 48–72 hrs. of growth for re-testing of the His$^+$ phenotype and for β-galactosidase assays, which were performed by a filter-lift method [L. Breeden and K. Nasmyth, *Cold Spring Harbor Symp. Quant. Biol*. 50:643 (1985)]. By 72 hours, 360 His$^+$ colonies had formed, and these were re-tested for histidine prototropy and assayed for β-galactosidase activity by a filter-lift method. FIG. 14A shows 20 representative His$^+$ colonies from the screen, all of which were confirmed as His$^+$ on re-testing (FIG. 14A, –His plate). Of these His$^+$ colonies, three exhibited β-galactosidase activity, two having somewhat greater activity than the PER homodimerization positive control and one having less activity (compare βgal-20 min. and βgal-120 min. panels). Altogether, a total of 67 His$^+$ colonies had β-galactosidase activity, with 23 having greater activity than the positive control, 11 having roughly the same activity, and 33 having less activity than the positive control, 11 having roughly the same activity, and 33 having less activity. Library plasmids were purified from 59 of the His$^+$, β-Gal$^+$ colonies. Inocula from His$^+$, β-gal$^+$ yeast colonies were grown in 2 ml of liquid THULL medium for 24–48 hours at 30° C., and plasmid DNA was recovered after glass-bead lysis of cells [C. S. Hoffman and F. Winston *Gene* 57:267 (1987)]. Plasmid DNA was electroporated into *E. coli* strain MC1066 [M. I. Chiu, H. Katz, V. Berlin, *Proc. Natl. Acad. Sci. USA* 91:12574 (1994)], which is auxotrophic for Trp and Leu, deficiencies that are complemented by the *S. cerevisiae* Trp 1 and Leu 2 markers, respectively. For selective recovery of VP16-cDNA library plasmids (Leu 2 marker) rather than LexA-PER bait plasmid (Trp 1 marker), bacterial transformants were plated onto minimal medium plates (+carbenicillin, tryptophan, uracil) lacing leucine. Transformants were then checked for the absence of bait plasmid by demonstrating failure to grow on minimal medium plates (+carbenicillin, leucine, uracil) lacing tryptophan. Across different experiments, from 1–5% of Leu$^+$ transformants were found to carry both plasmids; demonstration of a Trp$^-$ phenotype prior to plasmid purification is thus important for the reliability of subsequent specificity tests, which could be confounded by the presence of the original bait plasmid. 48 library plasmids produced PER-dependent His⁺, β-Gal⁺ interaction signals (see FIG. 14C for examples). The other 11 failed to produce interaction signals, most likely because, in these cases, an irrelevant, contaminating library plasmid was purified from the His⁺ colony.

Because of the possibility that the functional interaction between the tim and per genes is mediated by direct interaction of a predicted tim protein (TIM) with PER, Southern blots of the clones isolated in the two-hybrid screen were probed with a 4.5-kb cDNA derived from the tim locus. Altogether, inserts from 16 of the 48 plasmids producing PER-dependent interaction signals strongly hybridized to the probe at high stringency (FIG. 14B). The 16 hybridizing inserts ranged from 1.5 to 2.5 kb, and DNA sequences of the ends indicated that the set consisted of six different clones, with two clones represented four times, two represented three times, and two represented once.

To test reproducibility and specificity, each of the six library plasmids that hybridized to the tim cDNA was introduced back into yeast expressing the original LexA-PER bait or a negative control LexA-Lamin bait (Bartel et al (1993) *Biotechniques* 14:920). (FIG. 14C shows that the LexA-Lamin strain exhibits no detectable histidine prototropy or β-galactosidase activity after transformation with each of the six library plasmids. In contrast, the LexA-PER strain shows robust histidine prototropy after transformation with each of the six library plasmids, and it exhibits strong β-galactosidase activity relative to the PER homodimerization positive control when transformed with clones 2 or 4 and weaker β-galactosidase activity when transformed with clones 1, 3, 5, or 6 (FIG. 14C; compare βgal-20 min. and βgal-120 min. panels). The consistent differences in PER-dependent β-galactosidase activity produced by the six clones could result from differences in the affinity of their respective protein products for PER, but these differences could just as well result from other factors, such as differential VP16 hybrid proteins. In addition, when expressed as LexA bait hybrids, clones 1 and 2 showed PER-dependent interaction signals with VP16-cDNA library plasmids, none of the resulting ≈1000 colonies showed detectable β-galactosidase activity after a two-hour incubation in substrate, whereas colonies resulting from a parallel transformation with the VP16-PER plasmid exhibited marked β-galactosidase activity after 5–10 min. (Chua et al, unpublished observations). These experiments indicate that the interaction signals produced by these clones in the two hybrid system are highly specific for PER.

Sequences obtained from tim cDNA and genomic clones revealed an open reading frame encoding a novel protein of 1389 amino acids (Myers et al *Science* Nov. 3, 1995). Sequences from both ends of each of the six hybridizing two-hybrid clones, constituting a total of 3 kb, were compared to the tim sequence, and all were found to match internal segments at intervals in accordance with the size of each insert (FIG. 15). In addition, the double-stranded 1.5 kb sequence of clone 6 matched a 1.5 kb stretch of internal open reading frame. As determined by the VP16-insert fusion junctions, the reading frames of all six clones as translated in yeast agreed with the predicted open reading frame of the tim cDNA. All six clones overlap in the central portion of the open reading frame, indicating that a region sufficient for PER-dependent interaction signals lies within amino acids 505–906. This region does not include a PAS dimerization domain or any other sequence motif from which a function might be inferred, and it shows no significant similarity to any protein in the database (not shown; see also Myers et al, supra). These experiments demonstrate that six independent, overlapping clones isolated a total of 16 times in a two-hybrid screen for PER-interacting proteins are identical to a tim cDNA isolated by positional cloning (Myers et al, supra). It is concluded that these cDNAs are derived from the tim gene and propose that the functional interaction between the per and tim genes is mediated by a heterotypic interaction between the per and tim genes is mediated by a heterotypic interaction between their respective protein products.

FIG. 16A shows experiments in which the polarity of the elements in the two-hybrid system has been reversed. Several VP16-PER hybrids were tested for interactions with two LexA-TIM hybrids, TIM1 (designated clone 1 in FIGS. 14C and 15; modest β-galactosidase activity) and TIM2 (designated clone 2 in FIGS. 14C and 15; strong β-galactosidase activity). The lexA-TIM1 strain exhibits histidine prototropy and modes β-galactosidase activity after transformation with VP16-PER$_{233-685}$ (corresponding to the original bait) and after transformation with VP16-PER$_{233-390}$, a PER fragment corresponding to the N-terminal 158 amino acids of the 258-amino acid PAS domain and representing roughly one-eight of the PER sequence. No histidine prototropy or β-galactosidase activity is detectable after transformation of the LexA-TIM1 strain with VP16-PER$_{238-490}$, a fragment corresponding to a minimal PAS domain deleted of its five N-terminal residues. The LexA-TIM2 strain exhibits histidine prototropy and strong β-galactosidase activity after transformation with either VP16-PER$_{233-685}$ or VP16-PER$_{223-390}$ and weaker histidine prototropy and β-galactosidase activity after transformation with VP16-PER$_{238-490}$. Like the experiment shown in FIG. 14B, the LexA-Lamin strain produced no sign of histidine prototropy or β-galactosidase activity after transformation with any of these VP16-PER plasmids (not shown). These experiments indicate that a region sufficient to generate TIM-dependent interaction signals lies within PER$_{223-390}$. Because PER 233-685 and PER$_{223-390}$ produce indistinguishable TIM-dependent interaction signals, it can be inferred from the weak signal produced by PER$_{238-490}$ that amino acids 233–237 contribute to but are not required for the interaction.

Direct associated of TIM and PER polypeptide fragments was also tested in vitro. ³⁵S-Methionine-labelled TIM fragments were synthesized in vitro using coupled transcription-translation (TNT Lysate System, Promega). GST or GST-PER fusion proteins were produced in *E. coli* using the pGEX vector (Pharmacia) and purified on glutathione-agarose beads. For in vitro binding reactions, glutathion-eagarose beads with coupled GST or the indicated GST-PER fusion protein (50 µl, hydrated bead volume) were incubated at room temperature for 30 min. with labelled TIM (1.5×10⁵ cpm, Cerenkov) in binding buffer (200 µl, final, of 20 mM Hepes, pH 7.4; 100 mM KCl; 5 mM EDTA; 5 mM EGTA; 10% [v/v] glycerol; 5% [w/v] BSA; 0.4% NP40; 1 mM DTT). The beads were then washed at room temperature twice in binding buffer and twice in binding buffer lacking BSA (1 ml per wash). Beads were resuspended in an equal volume of 2×Laemmli buffer, incubated at 100° C. fir 5 min., and the entire sample was analyzed on 6% (FIG. 16B) or 7% (FIG. 16C) SDS-PAGE. (FIG. 16B). The indicated GST-PER fusion proteins or GST alone were expressed in bacteria (FIG. 16B, left), purified on glutathione-agarose beads, and incubated with the indicated in vitro-translated, ³⁵S-labelled TIM fragment. SDS-PAGE analysis shows that TIM$_{1-1003}$ binds to GST-PER$_{1-640}$ and GST-PER$_{1-914}$ binds to GST-PER$_{1-640}$, but not detectably to GST-PER$_{530-640}$ or GST alone (FIG. 16B, middle). In addition, TIM$_{1-914}$ binds to GST-PER$_{1-640}$, whereas TIM$_{1-446}$ shows no detectable binding to GST-PER$_{1-640}$ (FIG. 16B, right). These experiments demonstrate that TIM and PER polypeptides directly associate in vitro. The differential in vitro binding of different PER and TIM fragments is consistent with the two-hybrid interaction results. Those fragments which bind in vitro include all or nearly all of the segments inferred to be sufficient for interaction in two-hybrid assays (FIGS. 14C, 15, and 16A), whereas those which fail to bind in vitro map entirely outside the segments sufficient for interaction in two-hybrid assays. These results support the hypothesis that TIM regulates PER nuclear translocation through a direct protein-protein interaction.

Because PER$^L$ exhibits a temperature-sensitive delay in nuclear entry, a process apparently regulated by the tim gene, it was next examined whether PER$^L$ (V243D) (Baylies et al (1987) Nature 326:390) exhibits a temperature-sensitive phenotype in its interaction with TIM in two-hybrid assays. FIG. 17A shows β-galactosidase activity produced by patches of yeast that were grown at different temperatures on X-gal medium (Yeast transformants were patched to plates containing TULL medium supplemented with X-Gal (Sigma) to a final concentration of 100 μg/ml (added to TULL medium as a 1000X stock in N,N-dimethyl formamide). Transformants shown in FIG. 17A were grown as follows: TIM1: 22° C. for 6 days, 37° C. for 5 days; TIM2 and TIM4: 22° C. for 1.5 days, 37° C. for 1 day (see FIG. 17A legend)) after transformation with the indicated LexA-TIM and VP16-PER$^L_{233-685}$ and VP16-PER$^L_{233-290}$ are stronger than (TIM1) or equal to (TIM2 and TIM4) those produced by the corresponding wild-type PER fragments. In sharp contrast, at 37° C. the TIM-interaction signals produced by VP16-PER$^L_{233-685}$ and VP16-PER$^L_{233-290}$ are markedly weaker than those produced by the corresponding wild-type PER fragments in all three of the LexA-TIM strains. VP16-PER$^L_{233-685}$ or VP16-PER$^L_{233-685}$ after growth at the indicated temperatures. For each experiment, single TIM1,PER (wild-type) and TIM1,PER$^L$ transformants were processed in parallel. Each transformant yeast colony was resuspended in 6 ml cultures, which were then grown at 2, 28, or 35° C., respectively, for 24 hours. Cultures were diluted 100-fold with fresh TULL medium, and 2 ml of the diluted culture was grown (at the same temperature as the initial incubation) to a final A$_{600}$ of 0.8–1.2. Extraction of β-galactosidase from yeast and assays of β-galactosidase activity were performed as described [F. M. Ausubel, et al Current Protocols in Molecular Biology (John Wiley & Sons, New York, 1988)]. Specific β-galactosidase activity was calculated as Δ A$_{420}$/hr/mg protein. Within each independent experiment, specific β-galactosidase activities were normalized to that of the TIM1,PER (wild-type) control culture grown at 22° C. At 22° C. the TIM interaction signal generated by the PER$^L$ fragment is 3.4-fold higher than that of the wild type PER fragment (P<0.05), at 28° C. it is only marginally higher than that of wild type PER (1.8-fold, not significant), and at 35° C. it is 4.8-fold lower than that of wild type PER (P<0.001). Immunoblots, using antibodies directed against PER or against VP16, showed no detectable difference in the abundance of VP16-PER and VP16-PER$^L$ in extracts of the cultures grown at 35° C. (not shown), consistent with the normal abundance of PER$^L$ in vivo in Drosophila at elevated temperature (Huang et al (1995) Science 26:1169. These results indicate that the interaction between TIM and PER$^L$ for TIM could account for the temperature-sensitive delay of PER nuclear entry and the temperature-sensitive lengthening of circadian period in per$^L$ flies. These findings exclude a recent proposal (Huang et al supra), at least with regard to the PER-TIM interaction, that the PER$^L$ mutation disrupts the association of PER with other routines by means of a temperature-dependent, enhanced intramolecular association between PAS and the C-domain (PER$_{524-685}$) because PER$^L_{233-390}$, entirely lacking the C-domain, shows the same temperature-sensitive abnormality of interaction with TIM as does PER$^L_{233-685}$ in all three LexA-TIM strains (FIG. 17A).

Oscillations of the per transcript and PER protein likely depend on negative feedback regulation of per gene transcription by PER (Liu et al supra; Zweibel et al supra; Edery et al supra; Zeng et al supra; Hardin et al supra; Siwicki et al supra; For any such self-sustaining oscillator, theory predicts that some mechanism must operate during each cycle to delay the onset of this negative feedback, or else the oscillations would damp out (Friesen et al Annu. Rev. Physiol. 55:661 (1993)). The finding that PER accumulates exclusively in the cytoplasm and shifts to the nucleus only at a later time (Curtin et al Neuron 14:365 (1995)) suggests that cytoplasmic retention of PER contributes to this delay, since nuclear entry of PER is presumably required for its role in transcriptional autorepression. Given that nuclear translocation of PER requires a functional tim gene (Vosshall et al supra), it is proposed that the duration of this delay, and therefore the duration of the part of the circadian cycle in which per transcription is high, is determined by the protein-protein interaction between TIM and PER. This hypothesis is strongly supported by the finding of a temperature-sensitive defect in the interaction between TIM and PER$^L$, the protein product of a per allele characterized by temperature-sensitive long-period behavioral rhythms (Konopka et al (1989) J. Neurogenetics 6:1) and an associated temperature-sensitive delay in PER$^L$ translocation to the nucleus (Curtin et al supra). It is also supported by the recent identification of two long-period alleles of tim (Rothenfluh-Hilfiker et al, unpublished observations).

It is not known in what way the interaction between PER and TIM, likely required for PER nuclear translocation, is dependent on the phase of the circadian clock, as it must be if this interaction itself contributes to the timing mechanism. The finding that the tim transcript exhibits a circadian oscillation with the same phase as that of the per transcript (Sehgal et al Science Nov. 3, 1995) suggests that TIM also undergoes a circadian oscillation in abundance. If so, one possibility is that the clock-dependent accumulation of both PER and TIM sets a fairly sharp point in the cycle when the interaction becomes favored, thereby setting the point at which PER nuclear translocation occurs. Another possibility is that clock-dependent post-translational modification of PER (Edery et al (1994) Proc. Natl. Acad. Sci. USA 91:2260) or TIM could make one or both available for interaction or make the PER-TIM complex competent for PER nuclear translocation, but the demonstration of binding between PER synthesized in bacteria and TIM translated in vitro makes it unlikely that nay post-translational modification is required for the interaction itself.

A circadian clock is a self-sustaining, endogenous oscillator that drives daily rhythms in physiology and behavior (Moore-Ede, The Clocks That Time Us, Cambridge: Harvard University Press, 1982). Circadian clocks are remarkably widespread, having been documented in cyanobacteria, fungi, plants, invertebrates, and vertebrates (Edmunds Cellular and Molecular Bases of Biological Clocks, New York, Springer-Verlag (1988); Kondo et al Proc. Natl. Acad. Sci.

USA 90:5672 (1993)). All such clocks share certain fundamental properties. Most important are an intrinsic period close to 24 hours, resetting of the clock in response to light-dark transitions, and temperature-compensation of the period (Edmunds, 1993). Circadian clocks presumably evolved because an internal timing system of this sort makes possible the anticipation of daily environmental fluctuations, a capability that likely conferred a profound selective advantage (Hoffman *Proceedings, Dahlem Workshop* 20:63–75 (1976)).

Disturbances of circadian clock function can be inherited as monogenic traits (Dunlap, *Ann. Rev. Physiol.* 55:683 (1993)), and screens for mutants exhibiting aberrant circadian periods have been successfully carried out in a variety of organisms. These include the cyanobacterium Synechecoccus [T. Kondo et al *Science* 266:1233 (1994)]; the freshwater alga Chlamydomonas [V. G. Bruce *Genetics* 70:537 (1972)]; the fungus *Neurospora crassa* [J. F. Feldman and M. Hoyle *Genetics* 75:605 (1973)];Drosphila [R. J. Konopka and S. Benzer, *Proc. Natl. Acad. Sci. USA* 68:2112 (1971); Sehgal et al *Science* 263:1603 (1994)]; Arabidopsis [A. J. Millar, I. A. Carre, C. A. Strayer, N-H. Chua, S. A. Kay *Science* 267:1161 (1995)]; and the mouse [M. H. Vitaterna et al *Science* 264:719 (1994)]. Previously, the only circadian clock genes to have been cloned are the period (per) gene from Drosophila (Zehring et al Cell 39:369 (1984); Bargiello et al. *Nature* 312:752 (1984)) and the frequency (frg) gene from the fungus *Neurospora crassa* (McClung et al *Nature* 339:558 (1989)). Despite recent advances in understanding the roles played by the per (Liu et al *Neuron* 6:753 (1991); Zweibel et al *Proc. Natl. Acad. Sci. USA* 88:3882 (1991); Edery et al *Science* 263:237 (1994); Zeng et al *EMBO J.* 13:3590 (1994)) and frg (Aronson et al *Science* 263:1578 (1994)) genes in the fly and fungal circadian clocks, respectively, the molecular mechanism of circadian oscillations remains obscure.

The per gene almost certainly encodes a component of the Drosophila circadian clock. Both the per transcript (Hardin et al Nature 343:536 (1990)) and the per (Siwicki et al *Neuron* 1:121 (1988)) exhibit a circadian oscillation in abundance, and together genetic and biochemical studies (Liu et al (1991); Zweibel et al (1991); Edery et al (1994); Zeng et al (1994)) indicate that PER participates in negative feedback control of per gene expression. Despite this inferred role, PER has no known DNA-binding activity or recognizable DNA-binding motif. A suggestion that PER might act in association with a heterodimeric partner has come from the observation that PER contains a dimerization interface, termed PAS, that is conserved in several fly and mammalian transcription factors (Huang et al *Nature* 364:259 (1993)).

Regulated timing of PER nuclear translocation might be a critical determinant of clock period (Curtin et al supra; Vosshall et al supra). At the time corresponding to the peak of PER abundance, PER immunoreactivity in lateral neurons, the probable circadian pacemaker cells (Konopka et al *Mol. Gen. Genet.* 190:284 (1983); Ewer et al *J. Neurosci.* 12:3321 (1992); Frisch et al *Neuron* 12:555 (1994); Vosshall and Young *Neuron* 15:345 (1995)), shifts from exclusively cytoplasmic to predominantly nuclear (Curtin et al supra). It then remains nuclear for approximately 11 hours, after which time it disappears and the cycle recurs. In long-period mutant $per^L$ flies, this shift of PER immunoreactivity from cytoplasm to nucleus is delayed compared to that in wild-type flies, and this delay is exacerbated by elevated temperature, as is the long-period behavioral phenotype (Curtin et al supra).

The nuclear translocation of PER is likely regulated by a recently-identified second Drosophila circadian clock locus, timeless (tim) (Sehgal et al (1994)). In tim-mutant flies (now referred to as $tim^{01}$, a presumptive tim null allele, loss of behavioral circadian rhythms is accompanied by loss of circadian oscillations of per MRNA (Sehgal et al *Science* 263:1603 (1994)) and a failure of PER to undergo nuclear translocation (Vosshall et al *Science* 263:1601 (1994)). Examination of the subcellular localization of different report PER fusion proteins in $tim^{01}$ flies suggested that a signal for cytoplasmic retention is contained within the PER PAS region and that a functional tim gene is required to overcome this cytoplasmic retention (Vosshall et al *Science* 263:1601 (1994)). These observations imply that the tim gene regulates the timing of the PER negative feedback loop.

EXAMPLE 11

Rhythirc expression of timeless: A basis for promoting circadian cycles in period gene autoregulation. The clock gene timeless (tim) is required for circadian rhythmicity in Drosophila, tim RNA accumulates with a circadian rhythm. Phase and period of the tim RNA rhythm are indistinguishable from those reported for per. tim RNA oscillations are dependent on presence of PER and TIM proteins, which demonstrates feedback control of tim by a mechanism previously shown to regulate per expression. Because cyclic tim expression appears to dictate timing of PER protein accumulation and nuclear localization, it is proposed that tim promotes circadian rhythms of per and tim transcription by restricting per RNA and PER protein accumulation to separate times of day.

The tim gene has been cloned (Example 9). As previously described, tim is essential for the production of circadian rhythms in Drosophila (Sehgal et al (1994) *Science* 263:1603; Vosshall et al (1994) *Science* 263:1606). Because molecular data indicate that tim may be required at a specific time of day to allow accumulation and nuclear localization of the PER protein (Sehgal et al (1994) *Science* 263:1603; Vosshall et al (1994) *Science* 263:1606; Price et al (1995) *EMBO J.* 14:4044), it was determined if expression of the tim gene showed temporal regulation. This study focused on the expression in adult heads for the following reasons: (i) The clock is known to be located in the head (Konopka et al (1983) *J. Neurosci.* 12:3321); B. Frisch et al (1994) *Neuron* 12:555; Vosshall et al (1995) ibid. 15:345). (ii) Oscillation of per RNA was first demonstrated in adult heads, although subsequently it was shown to occur in most body tissues also (Hardin et al (1990) *Nature* 343:536; Hardin et al (1992) *EMBO J.* 11:1; Hardin et al (1992) *Proc. Natl. Acad. Sci. USA* 89:11711; Hardin et al (1994) *Mol. Cell. Biol.* 14:7211); and (iii) All effects of tim on per RNA and protein have been studied in adult heads (Sehgal et al (1994) *Science* 263:1603; Vosshall et al (1994) *Science* 263:1606; Price et al (1995) *EMBO J.* 14:4044).

Levels of tim mRNA were first determined in heads of adult flies that were maintained in the presence of 12 hour light/12 hour dark cycles (LD 12:12). Measurements made of tim RNA at four-hour intervals over a four-day period are shown in FIG. 18A. It was found that tim RNA levels oscillate over the course of LD 12:12, with peak levels corresponding to the end of the day and lowest levels to dawn. per RNA oscillations have he same phase (Sehgal et al (1994) *Science* 263:1603; Hardin et al (1990) *Nature* 343:536; Hardin et al (1992) *EMBO J.* 11:1; Hardin et al (1992) *Proc. Natl. Acad. Sci. USA* 89:11711; Hardin et al (1994) *Mol. Cell. Biol.* 14:7211). The amplitude of the variation in tim RNA levels appeared similar to that reported for per (Sehgal et al (1994) *Science* 263:1603; Hardin et al (1990) *Nature* 343:536; Hardin et al (1992) *EMBO J.* 11:1; Hardin et al (1992) *Proc. Natl. Acad. Sci. USA* 89:11711). On some days there was as much as a 15-fold difference between peak and trough levels (FIG. 18A, day 1).

Oscillations of per RNA persist in constant darkness and are therefore considered a circadian rhythm (Hardin et al (1990) *Nature* 343:536; Hardin et al (1992) *EMBO J.* 11:1; Hardin et al (1992) *Proc. Natl. Acad. Sci. USA* 89:11711). Oscillations of the RNA encoded by the frequency (frq) clock gene in Neurospora also persist in the absence of environmental signals (Aronson et al (1994) *Science* 263:1578; Crosthwaite et al (1995) *Cell* 81:1003). The expression of tim RNA was studied in wild type and $per^s$ flies under free-running conditions (FIG. 18B).

The same samples were also analyzed for expression of per RNA to better evaluate the correspondence of tim and per RNA cycling. per and tim RNA oscillations persist in constant darkness with indistinguishable periods, phases and amplitudes (FIG. 18B). The plot of tim RNA oscillations is essentially superimposed on the curve displaying per RNA cycling. Whereas both RNAs cycle with an approximately 23-hour periodicity in wild type, they cycle in $per^s$ with a 17- to 18-hour period (FIG. 18B). The amplitude of the oscillations in wild type $per^s$ flies is, however, reduced in freerunning conditions relative to the cycling observed in the presence of LD 12:12 (FIG. 18A). The above effects of constant darkness on amplitude of the tim RNA rhythm are comparable to those on per under these conditions (FIG. 18B, 6).

The effects of the $per^s$ mutation indicated that PER protein functions in the cyclic expression of tim MRNA. This was confirmed by analyzing the effect of the $per^{O1}$ mutation on the cycling of tim MRNA. The $per^{O1}$ gene contains a nonsense mutation at amino acid position 464 (full length PER is ~1200 amino acids) and is considered a null mutation because it does not express any functional gene product (Baylies et al (1993) in *Molecular Genetics of Biological Rhythms*, M. W. Young, ed. (Marcel-Dekker Inc., NY) 123–153. Like per RNA oscillations, tim RNA oscillations were abolished in $per^{O1}$ flies maintained in LD 12:12 (Sehgal, unpublished data). Thus, PER protein is required to sustain oscillating levels of tim mRNA as well as its own RNA.

The original tim mutation ($tim^{O1}$, 1) eliminates per RNA oscillations and is a null. $tim^{O1}$ contains a deletion that removes coding sequences and produces a frame shift leading to a truncated protein of about ½ the size of full-length TIM. To determine whether TIM protein is required for the cyclic expression of its own MRNA, tim RNA levels were measured at different times of day in $tim^{O1}$ flies maintained in LD 12:12. Although tim RNA fluctuations occurred, they did not display regularity suggesting a circadian or non-circadian rhythm (FIG. 18C). Thus, regular oscillations of tim RNA depend on the presence of TIM protein which indicates that products of the tim gene function in an autoregulatory feedback loop.

The tim and per genes appear to form a partnership that defmes central elements of the Drosophila pacemaker. Because autoregulation of tim requires PER protein, and vice versa, it is likely that PER and TIM are components of, and regulated by, the same feedback loop. That is, tim and per are both subject to autoregulation, and they regulate each other reciprocally. This interdependence is likely to be mediated by a direct physical association of the TIM and PER proteins. Additional evidence for action of tim as a component of the pacemaker comes from the recent discovery of multiple alleles of tim that display phenotypes ranging from long periodicity to arrhythmia (Rothenfluh-Hilfiker et al, unpublished data). Aspects of tim function and expression fulfill several criteria proposed for a "state variable" of the circadian pacemaker (reviewed in Aronson et al (1994) *Science* 263:1578; Crosthwaite et al (1995) *Cell* 81:1003; Zatz (1992) *Discoveries Neurosci.* 8:67). The only other genes known to satisfy these criteria are per, and the Neurospora clock locus frq.

The accumulation of PER protein lags behind the synthesis of its mRNA by ~6 hours. PER accumulates in perinuclear regions about an hour prior to its transport to the nucleus (Curtin et al (1995) *Neuron* 14:365). Because nuclear PER proteins may negatively regulate per transcription (Hardin et al (1990) *Nature* 343:536; Hardin et al (1992) *EMBO J.* 11:1; Hardin et al (1992) *Proc. Natl. Acad. Sci. USA* 89:11711; Zeng et al (1994) *EMBO J* 13:3590), such delays in the appearance and possibly nuclear activity of PER could be essential to any mechanism producing sustained oscillations in per RNA synthesis (Vosshall et al (1994) *Science* 263:1606; Hardin et al (1990) *Nature* 343:536; Hardin et al (1992) *EMBO J.* 11:1; Hardin et al (1992) *Proc. Natl. Acad. Sci. USA* 89:11711; Curtin (1995) *Neuron* 14:365; Zeng et al (1994) *EMBO J* 13:3590). The molecular events that are responsible for these delays are unknown, but are likely to involve tim. Accumulation of PER proteins is strongly and constitutively suppressed in $tim^0$ mutants (Vosshall et al (1994) *Science* 263:1606; Price et al (1995) *EMBO J.* 14:4044), and nuclear localization of PER reporter proteins is blocked in the mutant (Vosshall (1994) *Science* 263:1606). Thus, the finding that tim RNA is expressed with a circadian rhythm suggests that PER accumulation and nuclear localization are under temporal control that is dictated by the expression pattern of both per and tim.

The present invention has shown that the PER and TIM proteins physically interact with each other in vitro. Therefore, the dependence on tim function for PER accumulation and nuclear localization probably reflects a necessary interaction between the TIM and PER proteins in vivo. Because the present invention illustrates that the phase of tim RNA expression is similar to that of per RNA expression, the observed delays in PER accumulation and nuclear localization could reflect a concentration dependent association of the TIM and PER proteins. Particularly as PER accumulation is suppressed in $tim^{O1}$ mutants (Vosshall et al (1994) *Science* 263:1606; Price et al (1995) *EMBO J.* 14:4044). PER proteins might fail to accumulate in step with per RNA in wild type flies due to insufficient levels of TIM protein at early times of RNA synthesis. In this model (FIG. 19), higher levels of both RNAs would permit heterodimerization and stabilization of PER, but with a lag in relation to RNA synthesis. In addition, as suggested previously (Vosshall et al (1994) *Science* 263:1606), TIM might stabilize PER by promoting nuclear as opposed to cytoplasmic location.

Earlier work has shown that lowering per gene dosage or per RNA amounts lengthens the period (Baylies et al (1993)) Studies of the $per^L$ mutant are also consistent with this model. $PER^L$ proteins, which confer long period circadian behavioral rhythms (Konopka et al (1971) *Proc. Natl. Acad. Sci. USA* 68:2112) show delayed nuclear accumulation in vivo (Curtin (1995) *Neuron* 14:365), and altered binding to TIM in a yeast two-hybrid assay. In the model proposed in FIG. 19, the time of PER accumulation and nuclear entry depend on (1) the concentrations of per and tim RNAs and (2) the affinity of TIM for PER. It is also possible that other mechanisms and other, as yet unidentified, proteins influence the interaction between PER and TIM and affect the timing of PER accumulation and nuclear entry. Phosphorylation of PER, which has been shown to occur in a temporal manner, is one such mechanism (Edery et al *Proc. Natl. Acad. Sci. USA* 91:2260 (1994)).

EXAMPLE 12

Light-induced degradation of TIM protein and entrainment of the Drosophila circadian clock. To directly characterize the gene product of the timeless gene, TIM, from Drosophila heads, antibodies are raised against several recombinant TIM proteins expressed in bacteria (FIG. 20). Equivalent amounts of total protein from fly heads isolated at various times are separated by SDS-PAGE, blotted to nitrocellulose, and probed with anti-TIM antibodies as shown in FIG. 20. Fly head extracts are prepared as described (Edery et al (1994); Zeng et al (1994). TIM-specific antibodies are raised in rats against affinity purified glutathione-S-transferase fusion proteins expressing either residues 222–577 (Ab 307) or 1133–1389 (Ab 310) of TIM. The western blots shown in this example use Ab 307. The antibodies are prepared by HRP, Inc., Denver, Pa. All westerns in this example are visualized by chemiluminescence (ECL, Amersham, Arlington Heights, Ill.).

Levels of TIM protein at 4 hour intervals in a LD cycle (12 hours light: 12 hours dark) are shown in FIG. 20A (TIM, filled arrowhead; non-specific band, open arrowhead). The two lanes marked (D) (dark) and (L) (light) are extracts from $tim^0$ fly heads isolated from flies at ZT19 and ZT7, respectively.

Levels of TIM protein in $per^O$ fly heads under dark and light conditions are shown in FIG. 20B. The $per^O$ dark sample is prepared from dark-reared flies, and the light sample from ZT7 of a LD cycle.

Levels of TIM protein in extracts from control and light treated $per^O$ flies previously reared in constant darkness are shown in FIG. 20C. The $per^O$ flies are maintained in constant darkness for 4 days. At time "0", a set of flies is pulsed with light (~8000 lux) for a period of 1 hour, then returned to constant darkness. Control flies and light pulsed flies are harvested 0, 1, 2, 3, 5, 7, and 9 hours from the start of pulse. One group of flies are harvested immediately after 15 minutes of light. Head extracts and western blots are performed as in FIG. 20A. Lane numbering corresponds to time (in hours) from the start of a 1 hour light pulse; (*), light treated.

All TIM bands shown in FIG. 20C are quantified by densitometry with reference to a constitutively produced, non-specific protein that cross-reacts with the TIM antibody [see FIGS. 20A and B)]. Dashed profile is light pulsed data.

TIM, like PER, accumulates rhythmically in LD 12:12 (cycles of 12 hours light/12 hours dark) (FIG. 20A). The time of peak TIM accumulation in wild type heads occurred at about ZT 18 (ZT=zeitgeber time; ZT0=lights on, ZT12= lights off), and thus corresponds to the time of peak PER accumulation (Price et al., supra; Edery et al., supra). These rhythms were also observed in constant darkness. Although TIM has an apparent molecular weight of ~180–190 KD, there was an increasingly upward shift in TIM mobility late at night (compare ZT14 to ZT22). In fact, on shorter exposures, the TIM signal at ZT22 was resolved into at least two closely migrating bands. This behavior is reminiscent of PER (Price et al (1995); Edery et al (1994)). The antisera detects bona fide TIM protein: Extracts prepared from $tim^0$ fly heads lacked the TIM band (FIG. 20A), and antisera raised against a different region of TIM protein detected the same band seen in FIG. 20.

Although PER protein levels are reduced in a $tim^0$ genetic background (Sehgal et al., 1994, *Science*, 263:1603; Vosshall et al., 1994, *Science*, 263:1606; Price et al., 1995, *EMBO J*., 14:4044), TIM was expressed at fairly high levels in $per^O$ flies reared in constant darkness (FIG. 20B). Exposure to light reduced the amount of TIM because a sample from $per^O$ flies maintained in LD 12:12 and harvested at ZT7 showed much less TIM than a sample from dark-reared flies (FIG. 20B).

The $per^O$ flies, previously in constant darkness for 4 days, were exposed to a 1 hour pulse of light, followed by a recovery period in constant darkness. The amount of TIM dropped rapidly after the light treatment, and began to rise within the first hour after return to darkness (FIGS. 20C and D). A return to the pre-light exposure level occurred by ~5 hours (FIGS. 20C and D). The rapidity of this response was further indicated by measuring TIM protein amounts immediately following a 15 minute pulse of light. As shown in FIGS. 20C and D, (0.25*), a substantial loss of TIM was again observed. Taken together, these data indicate that, unlike PER in a $tim^0$ background, TIM protein is stable in $per^O$ flies. Moreover, light-induces loss of TIM protein without requiring PER protein, and is clock-independent.

Exposure of wild type flies to constant light produces a tim phenocopy, including behavioral arrhythmia, suppression of PER accumulation, and reduced PER phosphorylation (Price et al., supra; Zeng et al., supra). Constant light treatment of $tim^0$ flies produced no further change in the PER protein.

The data point to a mechanism for these effects of constant light, and indicate a role for TIM in light-dependent entrainment of the Drosophila clock. The influence of light delivered at different times of day on the phase of circadian behavioral rhythms is quantitatively expressed by a phase response curve (PRC) (FIG. 21A).

Figure 21A:
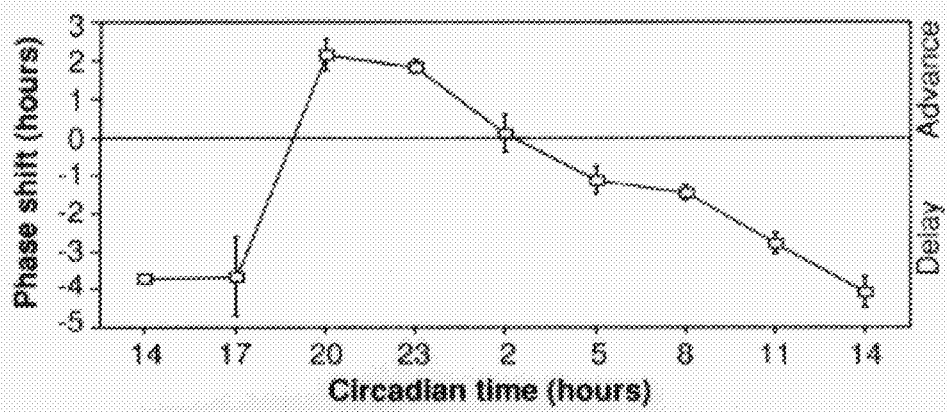

PRC of wild type flies is shown in FIG. 21A. The cn bw flies are entrained to a LD cycle for at least 3 days and then transferred to constant darkness. Ten minute pulses of light (~8000 lux) are administered at the indicated times. For each time point, the average phase of the locomotor activity rhythms of 16 pulsed flies is compared to that of 16 untreated control flies. Activity rhythms are assessed as described (Sehgal et al., 1994). Standard errors of the mean were derived from at least three independent experiments for each time point. The graph depicts the phase change of the locomotor activity rhythm following a 10-minute light pulse as a function of circadian time. Subjective day is indicated by the stippled bar.

Figure 21B:

FIG. 21B depicts the response of TIM protein levels to a light pulse administered at ZT16 followed by transfer to constant darkness, (*), light pulsed flies.

Figure 21C:

The response of TIM protein levels to a light pulse administered at ZT23 is shown in FIG. 21C. The experiment is performed as in FIG. 21B, except that light exposure occurs at ZT23 instead of ZT16. Except as noted, the experimental methods for light pulsed $per^O$ flies are as described for FIG. 20C.

Figure 21D:
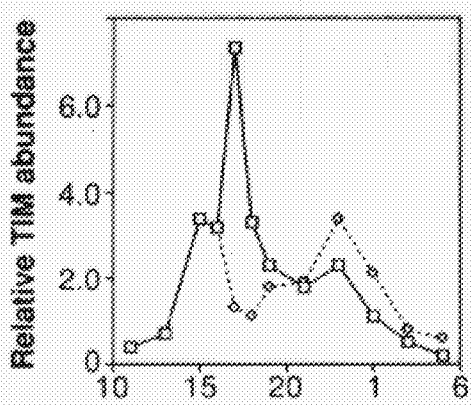
Figure 21E:
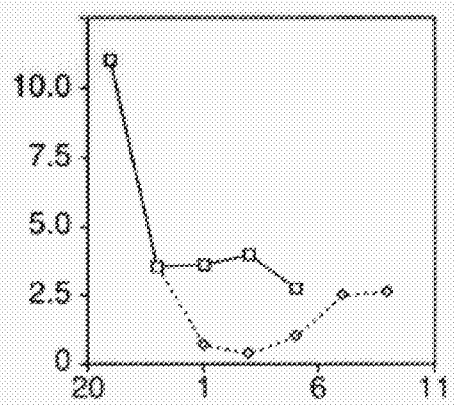

TIM bands shown in FIG. 21B are quantified by densitometry with reference to hsp70 in FIG. 21D. As shown in FIG. 21E, as hsp70 migrated past the region blotted, quantitation of TIM in FIG. 21C is performed against a non-specific, cross reacting protein as described in FIG. 20. Dashed profiles are light pulsed data.

Maximum phase delays of 4 to 5 hours are produced by light pulses delivered between CT14-16, whereas maximum phase advances, ~1 to 2 hours, are produced when light pulses of the same duration and intensity are provided between CT20–23 (FIG. 21A) (Dushay et al., 1990, Genetics, 125:557; Matsumoto et al., 1994, J. Neurogenet., 9:141; Levine et al., 1994, Neuron, 13:967). If adjustment of TIM levels by premature light exposure (relative to the phase of the existing rhythm) mediates light-resetting of the clock, TIM levels that respond, in a manner predicted by the Drosophila PRC would be expected. Therefore, wild type flies were exposed to 1-hour light pulses beginning at either ZT16 or ZT23, and then returned to constant darkness, and fly heads were collected at various times for western blot analysis.

Consistent with the phase delay in behavioral rhythms, we found that light exposure at ZT16 produced a reduction in TIM levels, followed by a rapid re-accumulation of TIM (FIGS. 21B and D). The level of TIM was substantially reduced by the end of the one hour light treatment (compare CT17 to CT17*, FIGS. 21B and D), and began to rise again within 2 hours following the transfer to darkness (compare CT19* to CT18*, FIGS. 21B and D). As the TIM level in control flies progressively decreased from a high point at CT17, the TIM level in light pulsed flies entered a re-accumulation phase with a new peak at CT23. Starting at CT23*, the level of TIM in the light pulsed samples was always higher than that of control flies sampled at the same circadian time (FIGS. 21B and D). The amount of TIM at CT23* was most similar to the amount accumulated in control flies at CT18, while CT1* most resembled CT19 to 23 (FIGS. 21B and D). The results demonstrate that the light pulse delays the molecular rhythm of TIM by 2 to 6 hours. This corresponds well with the 4 hour delay in the behavioral rhythm calculated from the PRC (FIG. 21A) (Dushay et al., supra).

FIGS. 21C and E show that a light pulse administered at ZT23, which produces 1 to 2 hour phase advances by PRC analysis (FIG. 21A) (Dushay et al., supra), reduced TIM like the ZT16 pulse, but the reduction was not followed by an interval of rapid re-accumulation. After the return to constant darkness, TIM levels remained barely detectable for 5 hours (CT1*, 3*, and 5*, FIGS. 21C and E), showing signs of re-accumulation only after 7 hours, which is shortly before the expected rise in TIM accumulation on the following subjective day (compare CT9* in FIG. 21C with the control accumulation at CT11, FIG. 21B). Thus, while a light pulse at ZT16, ultimately produced a delayed phase of TIM diminution, a light pulse at ZT23, caused a premature, monotonic decline in TIM that is well correlated with the behavioral advance obtained in the PRC (FIG. 21A) (Dushay et al., supra).

Immunocytochemical studies show highest PER accumulation in nuclei of the eyes and certain cell clusters, Lateral Neurons (LNs), of the central brain (Siwicki et al., 1988, Neuron, 1:141; Zerr et al., 1990, J. Neurosci., 10:2749; Ewer et al., 1992, J. Neurosci., 12:3321; Frisch et al., 994, Neuron, 12:555; Vosshall et al., 1995, Neuron, 15:345). Cycles of TIM immunostaining observed in LD 12:12 are shown FIGS. 22 A–D. Frontal sections of wild type heads show high levels of eye and brain staining at night (ZT22 and ZT20.5) as shown in FIGS. 22A, and 22D, respectively) and low levels during the day (ZT1 and ZT7) as shown in FIGS. 22B and C respectively. FIG. 22E shows TIM staining at CT6 whereas, FIG. 22F shows the pattern of staining in control, $tim^0$ head sections reared in DD. FIG. 22G shows TIM staining in cytoplasm, but not nuclei of eyes in $per^O$ flies reared in DD. Higher magnification showing cytoplasmic and nuclear TIM staining in putative Lateral Neurons in wild type (ZT17) is shown in FIG. 22H. Circular structure is esophagus. Arrows in FIGS. 22A and D indicate labeling of photoreceptor nuclei. Filled arrowheads in FIGS. 22A, D, and H show staining of putative LNs. Open arrowhead in FIG. 22G; cytoplasmic staining of $per^O$ photoreceptors. For "Dark" time points, flies are collected and frozen under a safelight (15 W bulb with Kodak GBX-2 filter). Sectioning, and immunostaining of heads performed as described (Vosshall et al., 1995, Neuron, 15:345). Except as noted, light pulses were administered as follows: The cn bw flies were entrained to an LD cycle for at least 3 days and then transferred to constant darkness. Ten minute pulses of light (~8000 lux) were administered at the indicated times.

TIM also accumulates in the nuclei of eyes, and in nuclei and cytoplasm of presumptive LNs (FIGS. 223A, D and H). Lower levels of TIM are found in cells dispersed throughout the optic lobes (FIGS. 22A and D). In agreement with western blot analysis, a rhythm of TIM staining was observed inmunocytochemically in wild type flies (FIGS. 22A–E).

TIM is produced at high levels in heads from $per^O$ flies at night (FIG. 21B). Immunocytochemistry revealed that high amounts of TIM accumulate in $per^O$ photoreceptor cells, but the protein is not associated with nuclei. Rather, TIM accumulates in the cytoplasm (compare FIGS. 22F and G). TIM is required for both accumulation and nuclear localization of PER (Sehgal et al., 1994; Price et al., supra). TIM nuclear localization depends on PER, but TIM accumulation does not.

Figures 23A, 23B, 23C, 23D, 23E, 23F:
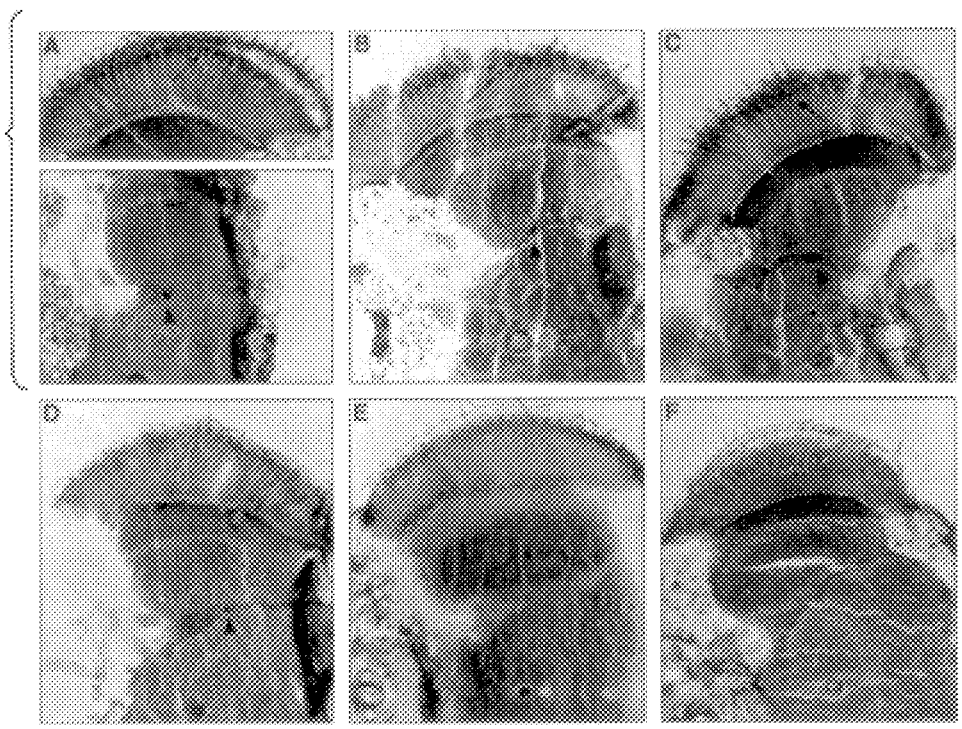

Blotting of proteins from light treated flies indicated rapid loss of TIM (FIGS. 20B, C and D; FIGS. 21B, C, D and E), but did not reveal the affected cell types. The effects of light was followed over an extended time course in wild type flies. Flies entrained to LD12:12 and exposed to a 10 min light pulse, as described for FIG. 22, delivered at ZT16 are collected at ZT17 (FIG. 23D), ZT18 (FIG. 23E), and ZT21 (FIG. 23F). Control flies (not light pulsed) are collected at ZT17 (FIG. 23A), ZT19 (FIG. 23B), and ZT21 (FIG. 23C). Examples of TIM staining in photoreceptor nuclei (arrows) and putative LNs (arrowheads) are indicated in FIGS. 23A, B, C and D.

As shown in FIGS. 23D, E and F, a 10 minute light pulse given at ZT 16 reduced the TIM staining in photoreceptors within 1 hour (ZT17, FIG. 23D). Staining in putative LNs was also clearly reduced, but only after a delay of 2 hours (FIGS. 23D, E and F). The observed delay in light-dependent diminution of TIM in LNs may be related to the abundance of the protein in these pacemaker cells, as their staining was often stronger than that of individual photoreceptor nuclei (cf. FIGS. 23A, B and C). An alternative is that the delay may reflect some dependence of the LNs on the eyes for TIM turnover.

The data indicate that TIM couples intracellular circadian cycles to light stimulation. Progression through the molecular cycle can be reset by light-induced elimination of TIM. If a light pulse is given at a time of night when a behavioral phase delay is induced (for example, ZT16) (FIGS. 21B and D), TIM diminution is immediately followed by re-accumulation. The molecular cycle of TIM levels is now reset to an earlier time point and the magnitude of the resulting molecular phase delay corresponds well with that of the behavioral phase delay. When a light pulse is given at a time of night that is associated with a small advance in the phase of the behavioral rhythm (ZT23, FIGS. 21C and E), TIM is prematurely lost, and recovery is not seen until the following day's cycle of accumulation.

As shown in a schematic depiction, FIG. 24, TIM protein appears to be an essential component of the Drosophila clock (Sehgal et al. (1995)). Tim is rapidly degraded by light, the phase of molecular and behavioral rhythms should be altered by light at times of day when TIM proteins are present. The tim RNA is most abundant in the early evening, at which time light pulses only transiently eliminate TIM proteins as they can be re-synthesized from existing RNA pools. If TIM suppresses accumulation of tim and per RNA (Sehgal et al. (1995)), the extended interval of TIM accumulation should delay subsequent rounds of RNA synthesis. Lowest amounts of tim RNA are observed near dawn (Sehgal et al., 1995). Light pulses at that time prematurely eliminate TIM, which cannot be replaced until new tim RNA synthesis ensues with the following day' cycle. Premature elimination of TIM by light should lead to advanced synthesis of tim and per RNA.

As indicated in FIG. 24, the different responses should be influenced by the different amounts of tim MRNA available for new protein synthesis at different times of night: Highest levels of tim mRNA occur in the early evening, and lowest levels occur near dawn (Sehgal et al., 1995). These conclusions are also supported by the kinetics of recovery of TIM following light pulses of $per^O$ flies. As $per^O$ flies have no measurable circadian pacemaker and produce tim RNA at high, constitutive levels (Sehgal et al., 1995), the amount of RNA is probably the only factor influencing the rate of TIM re-accumulation in the mutant.

In a natural environment, the light/dark cycle must make a contribution to the delay observed between per and tim RNA synthesis on the one hand, and nuclear accumulation of their encoded proteins on the other: Although per and tim RNAs begin to rise at mid-day, TIM's light sensitivity evidently precludes substantial accumulation of TIM protein until nightfall. Circadian pacemakers usually show species-specific, intrinsic periodicities that differ from 24 hours, while behavioral rhythms uniformly occur with a 24 hour period in the presence of a solar day. TIM's light sensitivity indicates a mechanism for adjusting to the period of the environmental cycle.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. A protein encode by a Drosophila timeless gene.

2. A method for detecting the presence or activity of the protein of claim 1 comprising:
 A. contacting a biological sample from an organism in which the presence or activity of said protein is suspected with a binding partner of said protein under conditions that allow binding of said protein to said binding partner to occur; and
 B. detecting whether binding has occurred between said protein in said sample and the binding partner;
 wherein the detection of binding indicates that the presence or activity of said protein in said sample.

3. A test kit for the demonstration of a nuclear translocation protein in a cellular sample, comprising:
 A. a predetermined amount of a detectably labeled specific binding partner of the protein of claim 1; and
 B. directions for use of said kit.

4. An active fragment of the protein of claim 1.

5. The protein of claim 1 labeled with a detectable label.

6. The protein of claim 5 wherein the label is selected from the group consisting of an enzyme, a chemical which fluoresces and a radioactive element.

7. An antibody to the protein of claim 1.

8. The antibody of claim 7 which is a polyclonal antibody.

9. The antibody of claim 7 which is a monoclonal antibody.

10. An immortal cell line that produces a monoclonal antibody according to claim 9.

11. The antibody of claim 7 labeled with a detectable label.

12. The antibody of claim 11 wherein the label is selected from the group consisting of an enzyme, a chemical which fluoresces and a radioactive element.

13. The protein of claim 1 having the amino acid sequence of SEQ ID NO:3.

14. An active fragment of the protein of claim 13.

15. An antibody to the protein of claim 13.

16. The protein of claim 1 having the amino acid sequence of SEQ ID NO:5.

17. An active fragment of the protein of claim 16.

18. An antibody to the protein of claim 16.

19. A DNA sequence or degenerate variant thereof, which encodes a nuclear translocation protein, or a fragment thereof, selected from the group consisting of:
 (A) the DNA sequence of SEQ ID NOS:1, 2 or 4;

(B) DNA sequences that hybridize to SEQ ID NOS:1, 2 or 4 under standard hybridization conditions; and (C) DNA sequences that code on expression for an amino acid sequence encoded by SEQ ID NOS:3 or 5.

20. A nucleic acid probe prepared from the DNA sequence of claim 19.

21. A recombinant DNA molecule comprising a DNA sequence or degenerate variant thereof, which encodes a nuclear translocation protein, or a fragment thereof, selected from the group consisting of:

(A) the DNA sequence of SEQ ID NOS:1, 2 or 4;

(B) DNA sequences that hybridize to SEQ ID NOS: 1, 2 or 4 under standard hybridization conditions; and (C) DNA sequences that code on expression for an amino acid sequence encoded by SEQ ID NOS:3 or 5.

22. The DNA molecule of either of claims, 19 or 21, wherein said DNA sequence is operatively linked to an expression control sequence.

23. A unicellular host transformed with a recombinant DNA molecule comprising a DNA sequence or degenerate variant thereof, which encodes a nuclear translocation protein, or a fragment thereof, selected from the group consisting of:

(A) the DNA sequence of SEQ ID NOS: 1, 2 or 4;

(B) DNA sequences that hybridize to SEQ ID NOS: 1, 2 or 4 under standard hybridization conditions; and (C) DNA sequences that code on expression for an amino acid sequence encoded by SEQ ID NOS:3 or 5, wherein said DNA sequence is operatively linked to an expression control sequence.

24. A recombinant DNA molecule having a DNA sequence which, on transcription, produces an antisense ribonucleic acid to an mRNA encoding a protein of claim 1, said antisense ribonucleic acid comprising a nucleic acid sequence capable of hybridizing to said mRNA.

25. A nuclear translocation factor-producing cell line transfected with the recombinant DNA molecule of claim 24.

\* \* \* \* \*